United States Patent [19]
Ullrich et al.

[11] Patent Number: 5,955,592
[45] Date of Patent: Sep. 21, 1999

[54] NUCLEIC ACID ENCODING NOVEL PROTEIN PHOSPHOTYROSINE PHOSPHATASE PTP-D1

[75] Inventors: Axel Ullrich, München, Germany; Niels Peter Hundahl Møller; Karin Bach Møller, both of Copenhagen, Denmark

[73] Assignee: Max Planck Gesellschaft zur Forderung der Wissenschaften e.V., Germany

[21] Appl. No.: 08/234,440

[22] Filed: Apr. 27, 1994

Related U.S. Application Data

[63] Continuation-in-part of application No. 07/923,740, Aug. 5, 1992, abandoned.
[51] Int. Cl.$^6$ .............................. C12N 15/55; C12N 9/16
[52] U.S. Cl. ..................... 536/23.2; 536/23.5; 435/69.1; 435/196; 435/252.3; 435/254.11; 435/325
[58] Field of Search ................................ 536/23.5, 23.2; 435/69.1, 240.1, 320.1, 252.3, 254.11, 194, 196, 325

[56] References Cited

FOREIGN PATENT DOCUMENTS

WO91/13173  9/1991  WIPO.
WO91/13989  9/1991  WIPO.
WO92/01050  1/1992  WIPO.

OTHER PUBLICATIONS

Daum et al., 1991, Characterization of a human recombinant receptor–linked protein tyrosine phosphatase, J. Biol. Chem., 266: 12211–12215.
Gebbink et al., 1991, Cloning, expression and chromosomal localization of a new putative receptor–like protein tyrosine phosphatase, FEBS Lett. 290: 123–130 (1991).
Tsai et al., 1991, Isolation and characterization of temperature–sensitive and thermostable mutants of the human receptor–like protein tyrosine phosphatase LAR, J. Biol. Chem. 266(16): 10534–10543.
George and Parker, 1990, Preliminary characterization of phosphotyrosine phosphatase activites in human peripheral blood lymphocytes: Identification of CD45 as a phosphotyrosine phosphatase, J. Cell Biochem. 42: 71–81.
Jirik et al., 1990, Cloning of a novel receptor–linked protein tyrosine phosphatase from a human hepatoblastoma cell line, FASEB J. 4A: 2082 (Abstr. 2253) (1990).
Jirik et al., 1990, Cloning and chromosomal assignment of a widely expressed human receptor–like protein tyrosine phosphatase, FEBS Lett. 273: 239–242 (1990).
Kaplan et al., 1990, Cloning of three human tyrosine phosphatases reveals a multigene family of receptor linked protein–tyrosine–phosphatases expressed in brain, Proc. Natl. Acad. Sci. USA 87: 7000–7004.
Krueger et al., 1990, Structural diversity and evolution of human receptor–like protein tyrosine phosphatases, EMBO J. 9: 3241–3252.

Matthews et al., 1990,Identification of an additional member of the protein–tyrosine–phosphatase family: Evidence for alternative splicing in the tryosine phosphatase domain, Proc. Natl. Acad. Sci. USA 87: 444–4448.
Ohagi et al., 1990, Sequence of a cDNA encoding human LRP (leukocyte common antigen–related peptide), Nucl. Acids Res. 18: 7159.
Sap et al., 1990, Cloning and expression of a widely expressed receptor tyrosine phosphatase, Proc. Natl. Acad. Sci. USA 87: 6112–6116.
Streuli et al., 1990, Distinct functional roles of the two intracellular phosphatase like domains of the receptor–linked protein tyrosine phosphatases LCA and LAR, EMBO Journal 9: 2399–2407.
Tonks et al., 1990, CD45, an integral membrane protein tyrosine phosphatase, J. Biol. Chem. 265: 10674–10680.
Butler et al., 1989, Characterization of a membrane–associated phosphotyrosyl protein phosphatase from the A431 human epidermoid carcinoma cell line, Eur. J. Biochem. 185: 475–483.
Kiener and Mittler, 1989, CD45–protein tyrosine phosphatase cross–linking inhibits T–cell receptor CD3 mediated activation in human T–cells, J. Immunol. 143: 23–28.
Mustelin et al., 1989, Rapid activation of the T–cell tyrosine protein kinase pp56lck by the CD45 phosphotyrosine phosphatase, Proc. Natl. Acad. Sci. USA 86: 6302–6306.
Ostergaard et al., 1989, Expression of CD45 alters phosphorylation of the lck–encoded tyrosine protein kinase in murine lymphoma T–cell lines, Proc. Natl. Acad. Sci. USA 86: 8959–8963 (1989).
Pingel and Thomas, Evidence that the leukocyte–common antigen is required for antigen–induced T, lymphocyte proliferation, Cell 58: 1055–1065 (1989).
Hall et al., 1989, Complete exon–intron organization of the human leukocyte common antigen (CD45) gene, J. Immunol. 141: 2781–2787.
Streuli et al., 1988, A new member of the immunoglobulin superfamily that has a cytoplasmic region homologous to the leukocyte common antigen, J. Exp. Med. 168: 1523–1530.
Charbonneau et al., 1988, The leukocyte common antigen (CD45): A putative receptor–linked protein tyrosine phosphatase, Proc. Natl. Acad. Sci. US 85: 7182–7186.
Ralph et al., 1987, Structural variants of human T200 glycoprotein (leukocyte–common antigen), EMBO J. 6: 1251–1257.

(List continued on next page.)

*Primary Examiner*—Sally P. Teng
*Attorney, Agent, or Firm*—Pennie & Edmonds LLP

[57] ABSTRACT

The present invention relates to PTP-D1, a member of the novel PTP-D subfamily of protein tyrosine phosphatases. The present invention is directed to isolated PTP-D1 protein, nucleic acid constructs encoding for PTP-D1, cells containing the nucleic acid constructs, and methods for production and identification of PTP-D1. Antibodies to PTP-D1 protein and methods for screening molecules which can bind to PTP-D1 protein or inhibit or stimulate the protein-tyrosine phosphatase enzymatic activity of PTP-D1, are also provided.

7 Claims, 21 Drawing Sheets

OTHER PUBLICATIONS

Tonks et al., 1987, Demonstration that the leukocyte common antigen CD45 is a protein tyrosine phosphatase, Biochemistry 27: 8695–8701.

Streuli et al., 1988, Differential usage of three exons generates at least five different mRNAs encoding human leukocyte common antigens, J. Exp. Med. 166: 1548–1566.

Hariharan et al., 1991, Cloning and characterization of a receptor–class phosphotyrosine phosphatase gene expressed on central nervous system axons in Drosophila melanogaster, Proc. Natl. Acad. Sci. USA 88:11266–11270.

Streuli et al., 1989, A family of receptor–linked protein tyrosine phosphatases in humans and Drosophila, Proc. Natl. Acad. Sci. USA 86: 8698–8702.

Matthews et al., 1992, Characterization of hematopoietic intracelluar protein tyrosine phosphatases: Description of a phosphatase containing an SH2 Domain and another enriched in proline–, glutamic acid–, serine–, and threonine–rich sequences, Molec. and Cell. Biol. 12: 2396–2405.

Plutzky et al., 1992, Isolation of a src homology 2–containing tyrosine phosphatase, Proc. Natl. Acad. Sci. USA 89: 1123–1127.

Yi et al., 1992, Protein tyrosine phosphatase containing SH2 domains: characterization, preferential expression in hematopoietc cells, and localization to human chromosome 12p12–p13, Mol. and Cell. Biol. 12: 836–846.

Gu et al., 1991, Identification, cloning, and expression of a cytosolic megakaryocyte protein–tyrosine phosphatase with sequence homology to cytoskeletal protein 4.1, Proc. Natl. Acad. Sci. USA 88: 5867–5871.

Lombroso et al., 1991, Molecular characterization of a protein–tyrosine–phosphatase enriched in striatum, Proc. Natl. Acad. Sci. USA 88: 7242–7246.

Shen et al., 1991, A protein–tyrosine phosphatase with sequence similarity to the SH2 domain of the protein–tyrosine kinases, Nature 352: 736–739.

Yang and Tonks, 1991, Isolation of a cDNA clone encoding a human protein–tyrosine phosphatase with homology to the cytoskeletal–associated proteins band 4.1, ezrin, and talin, Proc. Natl. Acad. Sci. USA 88: 5949–5953.

Chernoff et al., 1990, Cloning of a cDNA for a major human protein–tyrosine–phosphatase, Proc. Natl. Acad. Sci. USA, 87: 2735–2739.

Cool et al., 1990, Overexpression of a T–cell protein tyrosine phosphatase (PTPase) in BHK Cells, FASEB J. 4: A2078 (abstr. 2230).

Guan et al., 1990, Cloning and expression of a protein–tyrosine–phosphatase, Proc. Natl. Acad. Sci. USA87: 1501–1505.

Thomas, et al., 1990, ABA, A novel member of the tyrosine phosphatase family, FASEB J. 4: A2078 (Abstr. 3140).

Charbonneau et al., 1989, Human placenta protein–tyrosin–phosphatase: Amino acid sequence and relationship to a family of receptor–like proteins, Proc. Natl. Acad. Sci. USA 86: 5252–5256.

Cool et al., 1990, cDNA isolated from a human T–cell library encodes a member of the protein–tyrosine phosphatase family, Proc. Natl. Acad. Sci. USA 86: 5257–5261.

Pallen et al., 1988, Purification of a phosphotyrosine phosphatase that dephosphorylates the epidermal growth factor receptor autophosphorylation sites, Ann. N.Y. Acad. Sci. 551: 299–308.

Tonks et al., 1988, Purification of the major protein–tyrosine–phosphatases of human placenta, J. Biol. Chem. 263: 6722–6730.

Klarlund, 1985, Transformation of cells by an inhibitor of phosphatases acting on phosphotyrosine in proteins, Cell 41: 707–717.

Fischer et al., 1991, Protein tyrosine phosphatases: A diverse family of intracellular and transmembrane enzymes, Science 253: 401–406.

Hunter, 1989, Protein–tyrosine phosphatases: The other side of the coin, Cell 58: 1013–1016.

Jones et al., 1989, Phosphotyrosyl–protein phosphatases, J. Biol. Chem. 264: 7747–7753.

Tonks and Charbonneau, 1989, Protein tyrosine dephosphorylation and signal transduction, Trends in Biochem. Sci. 14: 497–500.

Matthews et al., 1991, Protein tyrosine phosphatase domains from protochordate Styela Plicata. Immunogenetics 33:33–41.

Guan et al., 1991, A Tyr/Ser protein phosphatase encoded by vaccinia virus. Nature 350:359–362.

Tonks et al., 1988, Characterization of the major protein–tyrosine–phosphatases of human placenta, J. Biol. Chem. 263:6731–6737.

Vogel et al., 1993, Activation of a phosphotyrosine phosphatase by tyrosine phosphorylation Science 259:1611–1614.

EMBL database entry SPPTPAO. Accession No. M38000, May 1, 1991.

Yang et al., 1993, Cloning and Expression of PTP–PEST, J. Biol. Chem. 268(9):6622–6628.

Yang et al., 1993, Cloning and Expression of PTP–PEST (Additions and Corrections), J. Biol. Chem. 268(23):17650.

Zhang and Goldstein, 1991, Identification of Skeletal Muscle Protein–Tyrosine Phosphatases by Amplification of Conserved cDNA Sequences, Biochem. Biophysic. Res. Comm. 178(3):1291–1297.

Co et al., 1992, Evidence for a Novel Protein Tyrosine Phosphatase in Human Skeletal Muscle, Biophys. J. 6(Part 2):A337 Abstract 1940.

Freeman et al., 1992, Identification of a Human src Homology 2–Containing Protein–Tyrosine–Phosphatase: A Putative Homolog of Drosophila Corkscrew, PNAS 89:11239–11243.

Gu et al., 1992, Cloning and Expression of a Cytosolic Megakaryocyte Protein–Tyrosine–Phosphatase with Sequence Homology to Retinaldehyde–Binding Protein and Yeast SEC14p., PNAS 89:2980–2984.

Matthews et al., 1992, Characterization of Hematopoietic Intracellular Protein Tyrosine Phosphatases: Description of a Phosphatase Containing an SH2 Domain and Another Enriched in Proline–, Glutamic Acid–, Serine– and Threonine–Rich Sequences, Molecular and Cellular Biology, 12(5):2396–2405.

Songyang et al., 1993, SH2 Domains Recognized Specific Phosphopeptide Sequences, Cell 72:767–778.

Koch et al., 1991, SH2 and SH3 Domains: Elements That Control Interactions of Cytoplasmic Signalling Proteins, Science 252:668–674.

```
          10                30                50
ttttggcagatggtatgggaacagggaattgcaattatagcaatggtgacagcagaagag
 F  W  Q  M  V  W  E  Q  G  I  A  I  I  A  M  V  T  A  E  E 70                90               110
gagggtxgaxxggagaagagctttaggtactggccacgacttggttccaggcacaacact
 E  G  X  X  E  K  S  F  R  Y  W  P  R  L  G  S  R  H  N  T 130               150               170
gtcacctatggaaggtttaagatcacgacccggttccgcacagactctggctgctatgcc
 V  T  Y  G  R  F  K  I  T  T  R  F  R  T  D  S  C  Y  A 190               210               230
accacaggcctgaagatgaagcacctccttaccgggcaagagagggaccgtctggcxxctc
 T  T  G  L  K  M  K  H  L  L  T  G  Q  E  R  T  V  W  X  L 250
caatacacagactggcctgaa
 Q  Y  T  D  W  P  E                    FIG.1
```

```
          10                30                50
ttctggcggatgatctgggagcagggagtgaatgtgattgccatggtcactgcagaggag
 F  W  R  M  I  W  E  Q  G  V  N  V  I  A  M  V  T  A  E  E 70                90               110
gagggtggacgaaccaaaagccaccgatactggcccaaactaggttcaaagcacagctca
 E  G  G  R  T  K  S  H  R  Y  W  P  K  L  G  S  K  H  S  S 130               150               170
gccacctatggcaagttcaaggtcaccacgaagtttcgaacggattctgtttgctatgca
 A  T  Y  G  K  F  K  V  T  T  K  F  R  T  D  S  V  C  Y  A 190               210               230
accacgggcttgaaggtcaagcaccttttgtctgggxaagaaaggacggtgtggcattta
 T  T  G  L  K  V  K  H  L  L  S  G  X  E  R  T  V  W  H  L 250               270
caatatactgactggcctgacttcggcgcc
 Q  Y  T  D  W  P  D  F  G  A

FIG.2
```

```
PIB    MVWEQKSRGVVMLNRVMEKGSLKCAQYWPQKEEKEMIFEDTNLKLTLISEDIKSYYTVRQ
PD1-   MVWEQGIAIIAMVTAEEEGXXEKSFRYWPRLGSRHNTVTYGRFKITTRFRTDSGCYATTG
PD2-   MIWEQGVNVIAMVTAEEEGGRTKSHRYWPKLGSKHSSATYGKFKVTTKFRTDSVCYATTG
       *.***    .*.     *     *  .***.    ..      .*.*           *.

PIB    LELENLTTQETREILHFHYTTWPDFGVPESPASFLNFLFKVRESGSLSPEHGPVVVHCSA
PD1-   LKMKHLLTGQERTVWXLQYTDWPEHGCPE-------------------------------
PD2-   LKVKHLLSGXERTVWHLQYTDWPDFGA---------------------------------
       *..*.   *.   ...** **. *
```

FIG.3A

```
P-D1  201  gattttggcagatggtatgggaacagggaattgcaattatagcaatggt  250
           || |||| |||| | ||||| ||||||| |    | || || |||||
           || |||| |||| | ||||| ||||||| |    | || || |||||
P-D2    1  ...ttctggcggatgatctgggagcagggagtgaatgtgattgccatggt   47

251  gacagcagaagaggagggtxgaxxggagaagagcttaggtactggccac  300
           || |||||| ||||||||| ||··   || |||    | |||||||||
           || |||||| ||||||||| ||··   || |||    | |||||||||
       48  cactgcagaggagggggtggacgaaccaaaagccaccgatactggccca   97

301  gacttggttccaggcacaacactgtcacctatggaaggtttaagatcacg  350
           ||| |||||| | ||||| | | | ||||||||| | ||| ||| ||||
           ||| |||||| | ||||| | | | ||||||||| | ||| ||| ||||
       98  aactaggttcaaagcacagctcagccacctatggcaagttcaaggtcacc  147

351  acccggttccgcacagactctggctgctatgccaccacaggcctgaagat  400
           ||   ||| || || || ||||  ||||||||| ||||| ||| ||||| |
           ||   ||| || || || ||||  ||||||||| ||||| ||| ||||| |
      148  acgaagtttcgaacggattctgtttgctatgcaaccacgggcttgaaggt  197

401  gaagcacctccttaccgggcaagagaggaccgtctggcxxctccaataca  450
           ||||||||  |  ||| ||||  || ||  |||| ·· | |||||  |
           ||||||||  |  ||| ||||  || ||  |||| ·· | |||||  |
      198  caagcaccttttgtctgggxaagaaaggacggtgtggcatttacaatata  247

451  cagactggcctgaacatggctgtccagaagacctcaagggatttttatca  500
           | ||||||||||    |||
           | ||||||||||    |||
      248  ctgactggcctgacttcggcgcc..................         270
```

FIG.3B

```
 51  EWDYIATQGPLQNTCQDFWQMVWEQGIAIIAMVTAEEEGXXEKSFRYWPR  100
     || |·||||· ·||||||||||   || ||||·
     ||·|·||||···||||||||||  ·|| ||||·
  1  ................FWRMIWEQGVNVIAMVTAEEEGGRTKSHRYWPK   33

101  LGSRHNTVTYGRFKITTRFRTDSGCYATTGLKMKHLLTGQERTVWXLQYT  150
     |||·|    |||·||·||·|||||·|||||||||·||||  | |||||  ||||
     |||·|···|||·||·||·|||||·|||||||||·||||·| |||||  ||||
 34  LGSKHSSATYGKFKVTTKFRTDSVCYATTGLKVKHLLSGXERTVWHLQYT   83

151  DWPEHGCPEDLKGFLSYLEEIQSVRRHTNSTSDPQSPNPPLLVHCSAGVG  200
     |||· |
     |||· |·
 84  DWPDFGA..........................................   90
```

FIG.3C

```
           10              30              50
gaattcttaagaaacggctagttgatggggagtgctcaacagcacgactccctgaaaatg
 I  L  K  K  R  L  V  D  G  E  C  S  T  A  R  L  P  E  N  A 70              90              110
cagaaagaaatcgattccaagatgTTCTTCCTTATGATGATGCCGAGAGTGGAGTTGGTCC
 E  R  N  R  F  Q  D  V  L  P  Y  D  D  A  R  V  E  L  V  P 130             150             170
CAACTAAAGAAAACAACACTGGTTACATCAACGCATCACATattlaaggtctctgtcagtg
 T  K  E  N  N  T  G  Y  I  N  A  S  H  I  K  V  S  V  S  G 190             210             230
gaatcgaatggggattatattgccacacagggaccattacagaatacctgtcaagatttt
 I  E  W  D  Y  I  A  T  Q  G  P  L  Q  N  T  C  Q  D  F  W 250             270             290
ggcagatggtatgggaacagggaattgcaattatagcaatggtgacagcagaagaggagg
 Q  M  V  W  E  Q  G  I  A  I  I  A  M  V  T  A  E  E  E  G 310             330             350
gtxgaxxggagaagagctttaggtactggccacgacttggttccaggcacaacactgtca
 X  X  E  K  S  F  R  Y  W  P  R  L  G  S  R  H  N  T  V  T 370             390             410
cctatggaaggttttaagatcacgacccggttccgcacagactctggctgctatgccacca
 Y  G  R  F  K  I  T  T  R  F  R  T  D  S  G  C  Y  A  T  T 430             450             470
caggcctgaagatgaagcacctccttaccgggcaagagaggaccgtctggcxxctccaat
 G  L  K  M  K  H  L  L  T  G  Q  E  R  T  V  W  X  L  Q  Y 490             510             530
acacagactggcctgaacatggctgtccagaagacctcaagggattttttatcatatcttg
 T  D  W  P  E  H  G  C  P  E  D  L  K  G  F  L  S  Y  L  E 550             570             590
aagagatccagtctgttcgacgccatacaaatagcacaagtgatccccaaagccccaacc
 E  I  Q  S  V  R  R  H  T  N  S  T  S  D  P  Q  S  P  N  P
```

FIG.4A

```
         610                 630                 650
ctccgttgttggtccactgcagtgctggggtaggaaggactggcgtggtgattttgtcgg
   P  L  L  V  H  C  S  A  G  V  G  R  T  G  V  V  I  L  S  E 670                 690                 710
agatcatgatcgcctgcctggaacacaatgaggtgctggacatcccgagagtgctggaca
   I  M  I  A  C  L  E  H  N  E  V  L  D  I  P  R  V  L  D  M 730                 750                 770
tgctgaggcaacagagaatgatgctggtgcagactctctgccagtacacatttgtgtaca
   L  R  Q  Q  R  M  M  L  V  Q  T  L  C  Q  Y  T  F  V  Y  R 790                 810                 830
gagtcctcatccagttcctgaaaagctccaggctcatctaagctcccacaatttcttacg
   V  L  I  Q  F  L  K  S  S  R  L  i  *

850                 870
gggccagtcatgtgaagcgtttacagcttaaaaaaaaa
```

FIG.4B

```
         10         20         30         40         50         60         70
          *          *          *          *          *          *          *
   GCCCATGAGC CGCGCCGCGGC CCGGGCTGGC GTGCGGGTGC GGCTGCGGCG GCCGCGCGGC GGGGCCCCGG
   CGGGTACTCG CGCGGCGCCG GGCCCGACCG CACGCCCACG CCGACGCCGC CGGCGCGCCG CCCCGGGGCC 80         90        100        110        120        130        140
          *          *          *          *          *          *          *
   GAGGCGGGTC GCTGAGCGGG GCGCGCGGCC CCGAGGATGC GGGAGCGGGA GCGGGAGCAG CGCTGGCGTC
   CTCCGCCCAG CGACTCGCCC CGCGCGCCGG GGCTCCTACG CCCTCGCCCT CGCCCTCGTC GCGACCGCAG 150        160        170        180        190        200        210
          *          *          *          *          *          *          *
   AATGCTCCCT TCCTCGGGCC ATTGGAGACT CCGTTGCTTT TTAATGGCGG CAGCGGCTGC TGGGTGAGCA
   TTACGAGGGA AGGAGCCCGG TAACCTCTGA GGCAACGAAA AATTACCGCC GTCGCCGACG ACCCACTCGT 220        230        240        250        260        270        280
          *          *          *          *          *          *          *
   GCTGGAGGCC GGACAGTGTT CGTCCCATCC GGAGAGGATC GCTTTCTCCT GGCGTCACCA GCGCTGGGTT
   CGACCTCCGG CCTGTCACAA GCAGGGTAGG CCTCTCCTAG CGAAAGAGGA CCGCAGTGGT CGCGACCCAA 290        300        310        320        330        340
          *          *          *          *          *          *
   GGTGGGGGTA GCTTTTCCCT CTTTGCTCCT CCATTCTTGA AGAAAGAAGA AG ATG CCA CTG CCA TTT
   CCACCCCCAT CGAAAAGGGA GAAACGAGGA GGTAAGAACT TCTTTCTTCT TC TAC GGT GAC GGT AAA
                                                            M   P   L   P   F>
  350        360        370        380        390        400
    *          *          *          *          *          *
   GGG TTG AAA CTG AAA CGC ACC CGG CGC TAC ACG GTG TCC AGC AAG AGT TGC CTG GTT
   CCC AAC TTT GAC TTT GCG TGG GCC GCG ATG TGC CAC AGG TCG TTC TCA ACG GAC CAA
    G   L   K   L   K   R   T   R   R   Y   T   V   S   S   K   S   C   L   V>

410        420        430        440        450        460
          *          *          *          *          *          *
   GCC CGG ATC CAA CTG CTT AAT AAC GAG TTT GTG GAG TTC ACC CTG TCC GTG GAG AGC
   CGG GCC TAG GTT GAC GAA TTA TTG CTC AAA CAC CTC AAG TGG GAC AGG CAC CTC TCG
    A   R   I   Q   L   L   N   N   E   F   V   E   F   T   L   S   V   E   S>

470        480        490        500        510
          *          *          *          *          *
   ACT GGC CAG GAA AGC CTC GAG GCC GTG GCC CAG AGG CTG GAG CTG CGG GAG GTC ACT
   TGA CCG GTC CTT TCG GAG CTC CGG CAC CGG GTC TCC GAC CTC GAC GCC CTC CAG TGA
    T   G   Q   E   S   L   E   A   V   A   Q   R   L   E   L   R   E   V   T>
```

FIG.5A

```
       520         530         540         550         560         570
        *           *           *           *           *           *
   TAC TTC AGC CTC TGG TAC TAC AAC AAG CAA AAT CAG CGC CGG TGG GTA GAT TTG GAA
   ATG AAG TCG GAG ACC ATG ATG TTG TTC GTT TTA GTC GCG GCC ACC CAT CTA AAC CTT
    Y   F   S   L   W   Y   Y   N   K   Q   N   Q   R   R   W   V   D   L   E>

580         590         600         610         620         630
            *           *           *           *           *           *
       AAA CCT TTG AAG AAG CAG CTG GAT AAA TAT GCA TTG GAA CCT ACC GTC TAT TTT GGA
       TTT GGA AAC TTC TTC GTC GAC CTA TTT ATA CGT AAC CTT GGA TGG CAG ATA AAA CCT
        K   P   L   K   K   Q   L   D   K   Y   A   L   E   P   T   V   Y   F   G>

640         650         660         670         680
                *           *           *           *           *
           GTG GTG TTT TAT GTG CCT TCA GTT TCT CAG CTG CAG CAG GAG ATT ACC AGG TAT CAG
           CAC CAC AAA ATA CAC GGA AGT CAA AGA GTC GAC GTC GTC CTC TAA TGG TCC ATA GTC
            V   V   F   Y   V   P   S   V   S   Q   L   Q   Q   E   I   T   R   Y   Q>

690         700         710         720         730         740
    *           *           *           *           *           *
   TAT TAT CTG CAA CTG AAG AAA GAT ATC TTG GAA GGA AGT ATT CCT TGT ACC TTA GAA
   ATA ATA GAC GTT GAC TTC TTT CTA TAG AAC CTT CCT TCA TAA GGA ACA TGG AAT CTT
    Y   Y   L   Q   L   K   K   D   I   L   E   G   S   I   P   C   T   L   E>

750         760         770         780         790         800
            *           *           *           *           *           *
       CAA GCA ATT CAG CTA GCA GGC TTA GCT GTT CAA GCG GAT TTT GGT GAC TTT GAT CAG
       GTT CGT TAA GTC GAT CGT CCG AAT CGA CAA GTT CGC CTA AAA CCA CTG AAA CTA GTC
        Q   A   I   Q   L   A   G   L   A   V   Q   A   D   F   G   D   F   D   Q>

810         820         830         840         850         860
                *           *           *           *           *           *
           TAT GAA TCC CAG GAC TTT CTT CAG AAA TTT GCC TTG TTT CCT GTG GGA TGG TTA CAA
           ATA CTT AGG GTC CTG AAA GAA GTC TTT AAA CGG AAC AAA GGA CAC CCT ACC AAT GTT
            Y   E   S   Q   D   F   L   Q   K   F   A   L   F   P   V   G   W   L   Q>

870         880         890         900         910
                        *           *           *           *           *
                   GAT GAA AAA GTA TTG GAA GAA GCA ACC CAA AAA GTG GCC TTA CTA CAT CAG AAA TAC
                   CTA CTT TTT CAT AAC CTT CTT CGT TGG GTT TTT CAC CGG AAT GAT GTA GTC TTT ATG
                    D   E   K   V   L   E   E   A   T   Q   K   V   A   L   L   H   Q   K   Y>
```

FIG. 5B

```
      920         930         940         950         960         970
       *           *           *           *           *           *
AGA GGG CTC ACA GCT CCT GAT GCT GAA ATG CTG TAC ATG CAG GAG GTA GAG AGA ATG
TCT CCC GAG TGT CGA GGA CTA CGA CTT TAC GAC ATG TAC GTC CTC CAT CTC TCT TAC
 R   G   L   T   A   P   D   A   E   M   L   Y   M   Q   E   V   E   R   M>

980         990        1000        1010        1020        1030
       *           *           *           *           *           *
GAT GGC TAT GGA GAA GAG AGC TAC CCT GCT AAG GAT AGC CAA GGA AGT GAC ATA TCC
CTA CCG ATA CCT CTT CTC TCG ATG GGA CGA TTC CTA TCG GTT CCT TCA CTG TAT AGG
 D   G   Y   G   E   E   S   Y   P   A   K   D   S   Q   G   S   D   I   S>

1040        1050        1060        1070        1080
            *           *           *           *           *
ATT GGA GCG TGT CTT GAA GGT ATC TTT GTG AAA CAC AAG AAT GGA AGG CAT CCT GTG
TAA CCT CGC ACA GAA CTT CCA TAG AAA CAC TTT GTG TTC TTA CCT TCC GTA GGA CAC
 I   G   A   C   L   E   G   I   F   V   K   H   K   N   G   R   H   P   V>

1090        1100        1110        1120        1130        1140
 *           *           *           *           *           *
GTA TTT AGG TGG CAT GAC ATT GCC AAC ATG TCC CAC AAC AAG TCC TTT TTT GCA TTA
CAT AAA TCC ACC GTA CTG TAA CGG TTG TAC AGG GTG TTG TTC AGG AAA AAA CGT AAT
 V   F   R   W   H   D   I   A   N   M   S   H   N   K   S   F   F   A   L>

1150        1160        1170        1180        1190        1200
       *           *           *           *           *           *
GAG CTG GCA AAT AAA GAG GAG ACC ATT CAA TTT CAA ACT GAA GAC ATG GAA ACA GCA
CTC GAC CGT TTA TTT CTC CTC TGG TAA GTT AAA GTT TGA CTT CTG TAC CTT TGT CGT
 E   L   A   N   K   E   E   T   I   Q   F   Q   T   E   D   M   E   T   A>

1210        1220        1230        1240        1250
            *           *           *           *           *
AAA TAC ATT TGG AGA CTC TGT GTT GCG CGA CAC AAG TTT TAC AGA CTA AAC CAG TGT
TTT ATG TAA ACC TCT GAG ACA CAA CGC GCT GTG TTC AAA ATG TCT GAT TTG GTC ACA
 K   Y   I   W   R   L   C   V   A   R   H   K   F   Y   R   L   N   Q   C>

1260        1270        1280        1290        1300        1310
 *           *           *           *           *           *
AAC CTG CAA ACT CAG ACT GTC ACA GTG AAC CCA ATC AGG AGG AGG TCT TCT TCA AGG
TTG GAC GTT TGA GTC TGA CAG TGT CAC TTG GGT TAG TCC TCC TCC AGA AGA AGT TCC
 N   L   Q   T   Q   T   V   T   V   N   P   I   R   R   R   S   S   S   R>
```

FIG.5C

```
      1320        1330        1340        1350        1360        1370
        *           *           *           *           *           *
ATG TCT CTG CCT AAA CCC CAG CCC TAC GTG ATG CCT CCC CCA CCG CAG TTG CAC TAT
TAC AGA GAC GGA TTT GGG GTC GGG ATG CAC TAC GGA GGG GGT GGC GTC AAC GTG ATA
 M   S   L   P   K   P   Q   P   Y   V   M   P   P   P   P   Q   L   H   Y>

1380        1390        1400        1410        1420        1430
        *           *           *           *           *           *
AAT GGA CAT TAT ACA GAA CCA TAT GCT TCT TCC CAA GAT AAC CTC TTT GTG CCC AAC
TTA CCT GTA ATA TGT CTT GGT ATA CGA AGA AGG GTT CTA TTG GAG AAA CAC GGG TTG
 N   G   H   Y   T   E   P   Y   A   S   S   Q   D   N   L   F   V   P   N>

1440        1450        1460        1470        1480
        *           *           *           *           *
CAG AAC GGA TAC TAC TGT CAC TCT CAG ACA AGC TTG GAT AGA GCC CAG ATT GAC TTC
GTC TTG CCT ATG ATG ACA GTG AGA GTC TGT TCG AAC CTA TCT CGG GTC TAA CTG AAG
 Q   N   G   Y   Y   C   H   S   Q   T   S   L   D   R   A   Q   I   D   F>

1490        1500        1510        1520        1530        1540
  *           *           *           *           *           *
AAC GGT CGG ATC CGT AAT GGC AGT GTC TAC AGT GCA CAC AGC ACC AAC TCC TTA AAT
TTG CCA GCC TAG GCA TTA CCG TCA CAG ATG TCA CGT GTG TCG TGG TTG AGG AAT TTA
 N   G   R   I   R   N   G   S   V   Y   S   A   H   S   T   N   S   L   N>

1550        1560        1570        1580        1590        1600
        *           *           *           *           *           *
AAT CCT CAG CCC TAC TTG CAG CCC TCG CCG ATG TCG TCC AAC CCT AGC ATC ACC GGG
TTA GGA GTC GGG ATG AAC GTC GGG AGC GGC TAC AGC AGG TTG GGA TCG TAG TGG CCC
 N   P   Q   P   Y   L   Q   P   S   P   M   S   S   N   P   S   I   T   G>

1610        1620        1630        1640        1650
        *           *           *           *           *
AGT GAC GTC ATG AGG CCT GAC TAC CTC CCG TCC CAT CGG CAC AGC GCC GTG ATA CCC
TCA CTG CAG TAC TCC GGA CTG ATG GAG GGC AGG GTA GCC GTG TCG CGG CAC TAT GGG
 S   D   V   M   R   P   D   Y   L   P   S   H   R   H   S   A   V   I   P>

1660        1670        1680        1690        1700        1710
  *           *           *           *           *           *
CCG TCC TAC CGC CCC ACC CCA GAC TAT GAG ACT GTG ATG AAG CAG CTC AAC AGG GGC
GGC AGG ATG GCG GGG TGG GGT CTG ATA CTC TGA CAC TAC TTC GTC GAG TTG TCC CCG
 P   S   Y   R   P   T   P   D   Y   E   T   V   M   K   Q   L   N   R   G>
```

FIG.5D

```
      1720        1730        1740        1750        1760        1770
        *           *           *           *           *           *
CTG GTG CAT GCG GAA CGG CAG AGC CAC TCG CTG CGA AAC CTC AAC ATC GGC AGC TCG
GAC CAC GTA CGC CTT GCC GTC TCG GTG AGC GAC GCT TTG GAG TTG TAG CCG TCG AGC
 L   V   H   A   E   R   Q   S   H   S   L   R   N   L   N   I   G   S   S>

1780        1790        1800        1810        1820
             *           *           *           *           *
TAC GCC TAC AGC AGG CCC GCG GCG CTG GTC TAC AGC CAG CCC GAG ATC CGC GAG CAC
ATG CGG ATG TCG TCC GGG CGC CGC GAC CAG ATG TCG GTC GGG CTC TAG GCG CTC GTG
 Y   A   Y   S   R   P   A   A   L   V   Y   S   Q   P   E   I   R   E   H>

1830        1840        1850        1860        1870        1880
    *           *           *           *           *           *
GCA CAG CTC CCC TCG CCA GCG GCC GCA CAC TGC CCG TTC AGC CTG AGC TAC AGC TTC
CGT GTC GAG GGG AGC GGT CGC CGG CGT GTG ACG GGC AAG TCG GAC TCG ATG TCG AAG
 A   Q   L   P   S   P   A   A   A   H   C   P   F   S   L   S   Y   S   F>

1890        1900        1910        1920        1930        1940
        *           *           *           *           *           *
CAC AGC CCG TCT CCC TAC CCC TAC CCT GCC GAG CGG CGG CCC GTG GTG GGC GCG GTC
GTG TCG GGC AGA GGG ATG GGG ATG GGA CGG CTC GCC GCC GGG CAC CAC CCG CGC CAG
 H   S   P   S   P   Y   P   Y   P   A   E   R   R   P   V   V   G   A   V>

1950        1960        1970        1980        1990        2000
        *           *           *           *           *           *
AGC GTG CCG GAG CTG ACC AAT GCG CAG CTG CAG GCG CAG GAC TAC CCG TCT CCC AAC
TCG CAC GGC CTC GAC TGG TTA CGC GTC GAC GTC CGC GTC CTG ATG GGC AGA GGG TTG
 S   V   P   E   L   T   N   A   Q   L   Q   A   Q   D   Y   P   S   P   N>

2010        2020        2030        2040        2050
             *           *           *           *           *
ATC ATG CGG ACG CAG GTG TAC CGG CCA CCC CCA CCC TAC CCG CCC CCC AGG CCC GCC
TAG TAC GCC TGC GTC CAC ATG GCC GGT GGG GGT GGG ATG GGC GGG GGG TCC GGG CGG
 I   M   R   T   Q   V   Y   R   P   P   P   P   Y   P   P   P   R   P   A>

2060        2070        2080        2090        2100        2110
    *           *           *           *           *           *
AAC AGC ACG CCA GAC CTG TCC CGC CAC CTT TAC ATC AGC AGC AGC AAC CCC GAC CTC
TTG TCG TGC GGT CTG GAC AGG GCG GTG GAA ATG TAG TCG TCG TCG TTG GGG CTG GAG
 N   S   T   P   D   L   S   R   H   L   Y   I   S   S   S   N   P   D   L>
```

FIG.5E

```
           2120        2130        2140        2150        2160        2170
             *           *           *           *           *           *
         ATC ACG CGG CGC GTG CAC CAC TCG GTG CAA ACG TTC CAG GAG GAC AGC CTG CCC GTG
         TAG TGC GCC GCG CAC GTG GTG AGC CAC GTT TGC AAG GTC CTC CTG TCG GAC GGG CAC
          I   T   R   R   V   H   H   S   V   Q   T   F   Q   E   D   S   L   P   V>

2180        2190        2200        2210        2220
                   *           *           *           *           *
         GCG CAC TCG CTG CAG GAG GTC AGC GAG CCC CTC ACC GCC GCG CGC CAC GCG CAG CTG
         CGC GTG AGC GAC GTC CTC CAG TCG CTC GGG GAG TGG CGG CGC GCG GTG CGC GTC GAC
          A   H   S   L   Q   E   V   S   E   P   L   T   A   A   R   H   A   Q   L>

2230        2240        2250        2260        2270        2280
            *           *           *           *           *           *
         CAC AAA CGG AAC AGC ATC GAG GTG GCC GGG CTC AGC CAC GGC CTG GAG GGC CTG CGG
         GTG TTT GCC TTG TCG TAG CTC CAC CGG CCC GAG TCG GTG CCG GAC CTC CCG GAC GCC
          H   K   R   N   S   I   E   V   A   G   L   S   H   G   L   E   G   L   R>

2290        2300        2310        2320        2330        2340
                   *           *           *           *           *           *
         CTC AAG GAG CGC ACC CTA TCC GCG TCG GCG GCA GAG GTG GCG CCG CGA GCC GTC TCG
         GAG TTC CTC GCG TGG GAT AGG CGC AGC CGC CGT CTC CAC CGC GGC GCT CGG CAG AGC
          L   K   E   R   T   L   S   A   S   A   A   E   V   A   P   R   A   V   S>

2350        2360        2370        2380        2390
                        *           *           *           *           *
         GTG GGC TCC CAG CCC AGC GTT TTC ACC GAG AGG ACA CAG CGA GAA GGG CCG GAG GAG
         CAC CCG AGG GTC GGG TCG CAA AAG TGG CTC TCC TGT GTC GCT CTT CCC GGC CTC CTC
          V   G   S   Q   P   S   V   F   T   E   R   T   Q   R   E   G   P   E   E>

2400        2410        2420        2430        2440        2450
           *           *           *           *           *           *
         GCG GAG GGC TTG AGG TAC GGC CAT AAG AAG TCC CTG TCG GAC GCC ACC ATG CTA ATC
         CGC CTC CCG AAC TCC ATG CCG GTA TTC TTC AGG GAC AGC CTG CGG TGG TAC GAT TAG
          A   E   G   L   R   Y   G   H   K   K   S   L   S   D   A   T   M   L   I>

2460        2470        2480        2490        2500        2510
                   *           *           *           *           *           *
         CAC AGC AGC GAG GAG GAG GAG GAC GAG GAC TTC GAG GAG GAG AGC GGG GCC CGG GCG
         GTG TCG TCG CTC CTC CTC CTC CTG CTC CTG AAG CTC CTC CTC TCG CCC CGG GCC CGC
          H   S   S   E   E   E   E   D   E   D   F   E   E   E   S   G   A   R   A>
```

FIG. 5F

```
      2520        2530        2540        2550        2560        2570
        *           *           *           *           *           *
    CCC CCT GCA CGT GCG CGC GAG CCT CGG CCC GGC CTG GCC CAG GAC CCA CCT GGC TGC
    GGG GGA CGT GCA CGC GCG CTC GGA GCC GGG CCG GAC CGG GTC CTG GGT GGA CCG ACG
     P   P   A   R   A   R   E   P   R   P   G   L   A   Q   D   P   P   G   C>

2580        2590        2600        2610        2620
              *           *           *           *           *
    CCT CGC GTC CTG CTC GCC GGG CCC CTG CAC ATC CTG GAG CCC AAG GCC CAC GTC CCA
    GGA GCG CAG GAC GAG CGG CCC GGG GAC GTG TAG GAC CTC GGG TTC CGG GTG CAG GGT
     P   R   V   L   L   A   G   P   L   H   I   L   E   P   K   A   H   V   P>

2630        2640        2650        2660        2670        2680
   *           *           *           *           *           *
   GAC GCG GAG AAG AGG ATG ATG GAC AGC AGC CCC GTC CGC ACG ACC GCA GAG GCC CAG
   CTG CGC CTC TTC TCC TAC TAC CTG TCG TCG GGG CAG GCG TGC TGG CGT CTC CGG GTC
    D   A   E   K   R   M   M   D   S   S   P   V   R   T   T   A   E   A   Q>

2690        2700        2710        2720        2730        2740
              *           *           *           *           *           *
    CGG CCC TGG AGA GAC GGG CTG CTG ATG CCC TCC ATG TCG GAG TCC GAC CTC ACC ACG
    GCC GGG ACC TCT CTG CCC GAC GAC TAC GGG AGG TAC AGC CTC AGG CTG GAG TGG TGC
     R   P   W   R   D   G   L   L   M   P   S   M   S   E   S   D   L   T   T>

2750        2760        2770        2780        2790
              *           *           *           *           *
    TCA GGC CGC TAC CGA GCC CGG AGG GAC TCT CTG AAG AAA AGG CCG GTG TCG GAC CTT
    AGT CCG GCG ATG GCT CGG GCC TCC CTG AGA GAC TTC TTT TCC GGC CAC AGC CTG GAA
     S   G   R   Y   R   A   R   R   D   S   L   K   K   R   P   V   S   D   L>

2800        2810        2820        2830        2840        2850
   *           *           *           *           *           *
   CTC TCT GGG AAG AAG AAC ATC GTG GAA GGG CTC CCG CCT CTA GGG GGA ATG AAA AAG
   GAG AGA CCC TTC TTC TTG TAG CAC CTT CCC GAG GGC GGA GAT CCC CCT TAC TTT TTC
    L   S   G   K   K   N   I   V   E   G   L   P   P   L   G   G   M   K   K>

2860        2870        2880        2890        2900        2910
              *           *           *           *           *           *
    ACT CGA GTA GAT GCA AAA AAA ATT GGT CCT CTT AAA CTG GCT GCC CTA AAT GGA CTC
    TGA GCT CAT CTA CGT TTT TTT TAA CCA GGA GAA TTT GAC CGA CGG GAT TTA CCT GAG
     T   R   V   D   A   K   K   I   G   P   L   K   L   A   A   L   N   G   L>
```

FIG.5G

```
      2920        2930        2940         2950        2960
       *           *           *            *           *
TCC CTA TCT CGA GTG CCT CTG CCT GAT GAA GGA AAG GAA GTG GCT ACC AGA GCA ACG
AGG GAT AGA GCT CAC GGA GAC GGA CTA CTT CCT TTC CTT CAC CGA TGG TCT CGT TGC
 S   L   S   R   V   P   L   P   D   E   G   K   E   V   A   T   R   A   T>

2970        2980        2990         3000        3010        3020
 *           *           *            *           *           *
AAT GAT GAA AGG TGT AAA ATT CTG GAA CAA CGA TTA GAA CAA GGA ATG GTA TTC ACA
TTA CTA CTT TCC ACA TTT TAA GAC CTT GTT GCT AAT CTT GTT CCT TAC CAT AAG TGT
 N   D   E   R   C   K   I   L   E   Q   R   L   E   Q   G   M   V   F   T>

3030        3040        3050        3060        3070        3080
     *           *           *           *           *           *
GAA TAT GAA AGA ATT CTT AAG AAA CGG CTA GTT GAT GGG GAG TGC TCA ACA GCA CGA
CTT ATA CTT TCT TAA GAA TTC TTT GCC GAT CAA CTA CCC CTC ACG AGT TGT CGT GCT
 E   Y   E   R   I   L   K   K   R   L   V   D   G   E   C   S   T   A   R>

3090        3100        3110        3120        3130        3140
     *           *           *           *           *           *
CTC CCT GAA AAT GCA GAA AGA AAT CGA TTC CAA GAT GTT CTT CCT TAT GAT GAT GCG
GAG GGA CTT TTA CGT CTT TCT TTA GCT AAG GTT CTA CAA GAA GGA ATA CTA CTA CGC
 L   P   E   N   A   E   R   N   R   F   Q   D   V   L   P   Y   D   D   A>

3150        3160        3170        3180        3190
         *           *           *           *           *
AGA GTG GAG TTG GTC CCA ACT AAA GAA AAC AAC ACT GGT TAC ATC AAC GCA TCA CAT
TCT CAC CTC AAC CAG GGT TGA TTT CTT TTG TTG TGA CCA ATG TAG TTG CGT AGT GTA
 R   V   E   L   V   P   T   K   E   N   N   T   G   Y   I   N   A   S   H>

3200        3210        3220        3230        3240        3250
 *           *           *           *           *           *
ATT AAG GTC TCT GTC AGT GGA ATC GAA TGG GAT TAT ATT GCC ACA CAG GGA CCA TTA
TAA TTC CAG AGA CAG TCA CCT TAG CTT ACC CTA ATA TAA CGG TGT GTC CCT GGT AAT
 I   K   V   S   V   S   G   I   E   W   D   Y   I   A   T   Q   G   P   L>

3260        3270        3280        3290        3300        3310
     *           *           *           *           *           *
CAG AAT ACC TGT CAA GAT TTT TGG CAG ATG GTA TGG GAA CAG GGA ATT GCA ATT ATA
GTC TTA TGG ACA GTT CTA AAA ACC GTC TAC CAT ACC CTT GTC CCT TAA CGT TAA TAT
 Q   N   T   C   Q   D   F   W   Q   M   V   W   E   Q   G   I   A   I   I>
```

FIG.5H

```
            3320         3330         3340         3350         3360
              *            *            *            *            *
      GCA ATG GTG ACA GCA GAA GAG GAG GGT GGA AGG GAG AAG AGC TTT AGG TAC TGG CCA
      CGT TAC CAC TGT CGT CTT CTC CTC CCA CCT TCC CTC TTC TCG AAA TCC ATG ACC GGT
       A   M   V   T   A   E   E   E   G   G   R   E   K   S   F   R   Y   W   P>

3370         3380         3390         3400         3410         3420
    *            *            *            *            *            *
  CGA CTT GGT TCC AGG CAC AAC ACT GTC ACC TAT GGA AGG TTT AAG ATC ACG ACC CGG
  GCT GAA CCA AGG TCC GTG TTG TGA CAG TGG ATA CCT TCC AAA TTC TAG TGC TGG GCC
   R   L   G   S   R   H   N   T   V   T   Y   G   R   F   K   I   T   T   R>

3430         3440         3450         3460         3470         3480
            *            *            *            *            *            *
      TTC CGC ACA GAC TCT GGC TGC TAT GCC ACC ACA GGC CTG AAG ATG AAG CAC CTC CTT
      AAG GCG TGT CTG AGA CCG ACG ATA CGG TGG TGT CCG GAC TTC TAC TTC GTG GAG GAA
       F   R   T   D   S   G   C   Y   A   T   T   G   L   K   M   K   H   L   L>

3490         3500         3510         3520         3530
                *            *            *            *            *
          ACC GGG CAA GAG AGG ACC GTC TGG CAC CTC CAA TAC ACA GAC TGG CCT GAA CAT GGC
          TGG CCC GTT CTC TCC TGG CAG ACC GTG GAG GTT ATG TGT CTG ACC GGA CTT GTA CCG
           T   G   Q   E   R   T   V   W   H   L   Q   Y   T   D   W   P   E   H   G>

3540         3550         3560         3570         3580         3590
    *            *            *            *            *            *
  TGT CCA GAA GAC CTC AAG GGA TTT TTA TCA TAT CTT GAA GAG ATC CAG TCT GTT CGA
  ACA GGT CTT CTG GAG TTC CCT AAA AAT AGT ATA GAA CTT CTC TAG GTC AGA CAA GCT
   C   P   E   D   L   K   G   F   L   S   Y   L   E   E   I   Q   S   V   R>

3600         3610         3620         3630         3640         3650
            *            *            *            *            *            *
      CGC CAT ACA AAT AGC ACA AGT GAT CCC CAA AGC CCC AAC CCT CCG TTG TTG GTC CAC
      GCG GTA TGT TTA TCG TGT TCA CTA GGG GTT TCG GGG TTG GGA GGC AAC AAC CAG GTG
       R   H   T   N   S   T   S   D   P   Q   S   P   N   P   P   L   L   V   H>

3660         3670         3680         3690         3700         3710
            *            *            *            *            *            *
      TGC AGT GCT GGG GTA GGA AGG ACT GGC GTG GTG ATT TTG TCG GAG ATC ATG ATC GCC
      ACG TCA CGA CCC CAT CCT TCC TGA CCG CAC CAC TAA AAC AGC CTC TAG TAC TAG CGG
       C   S   A   G   V   G   R   T   G   V   V   I   L   S   E   I   M   I   A>
```

FIG. 51

```
         3720        3730        3740        3750        3760
           *           *           *           *           *
TGC CTG GAA CAC AAT GAG GTG CTG GAC ATC CCG AGA GTG CTG GAC ATG CTG AGG CAA
ACG GAC CTT GTG TTA CTC CAC GAC CTG TAG GGC TCT CAC GAC CTG TAC GAC TCC GTT
 C   L   E   H   N   E   V   L   D   I   P   R   V   L   D   M   L   R   Q>

3770        3780        3790        3800        3810        3820
    *           *           *           *           *           *
CAG AGA ATG ATG CTG GTG CAG ACT CTC TGC CAG TAC ACA TTT GTG TAC AGA GTC CTC
GTC TCT TAC TAC GAC CAC GTC TGA GAG ACG GTC ATG TGT AAA CAC ATG TCT CAG GAG
 Q   R   M   M   L   V   Q   T   L   C   Q   Y   T   F   V   Y   R   V   L>

3830        3840        3850        3860        3870        3880
         *           *           *           *           *           *
ATC CAG TTC CTG AAA AGC TCC AGG CTC ATC TAA GCT CCCACAATTT CTTACGGGGC
TAG GTC AAG GAC TTT TCG AGG TCC GAG TAG ATT CGA GGGTGTTAAA GAATGCCCCG
 I   Q   F   L   K   S   S   R   L   I   *>

3890       3900       3910       3920       3930       3940       3950
       *          *          *          *          *          *          *
CAGTCATGTG AAGCGTTTAC AGCTTAAAAA AAAAGCGCTT GCCTAACTCA TACTTTCCCG TTGACACTTG
GTCAGTACAC TTCGCAAATG TCGAATTTTT TTTTCGCGAA CGGATTGAGT ATGAAAGGGC AACTGTGAAC 3960       3970       3980       3990       4000       4010       4020
       *          *          *          *          *          *          *
ATCCACGCAG CGTGGCACTG GGACGTAAGT GGCGCAGTCT GAATGGCGGC ACGCTGAAGG AAACGTGCGA
TAGGTGCGTC GCACCGTGAC CCTGCATTCA CCGCGTCAGA CTTACCGCCG TGCGACTTCC TTTGCACGCT 4030       4040       4050       4060       4070       4080
       *          *          *          *          *          *
AGCACAGGCT GAAGAGGGGT TTCTAACCTG GGAAAGGTGC TCAAGGAGGA CTTGGTTTCA
TCGTGTCCGA CTTCTCCCCA AAGATTGGAC CCTTTCCACG AGTTCCTCCT GAACCAAAGT
```

FIG.5J

```
  1 MPLPFGLKLKRTRRYTVSSKSCLVARIQLLNNEFVEFTLSVESTGQESLE
 51 AVAQRLELREVTYFSLWYYNKQNQRRWVDLEKPLKKQLDKYALEPTVYFG
101 VVFYVPSVSQLQQEITRYQYYLQLKKDILEGSIPCTLEQAIQLAGLAVQA
151 DFGDFDQYESQDFLQKFALFPVGWLQDEKVLEEATQKVALLHQKYRGLTA
201 PDAEMLYMQEVERMDGYGEESYPAKDSQGSDISIGACLEGIFVKHKNGRH
251 PVVFRWHDIANMSHNKSFFALELANKEETIQFQTEDMETAKYIWRLCVAR
301 HKFYRLNQCNLQTQTVTVNPIRRRSSSRMSLPKPQPYVMPPPPQLHYNGH
351 YTEPYASSQDNLFVPNQNGYYCHSQTSLDRAQIDFNGRIRNGSVYSAHST
401 NSLNNPQPYLQPSPMSSNPSITGSDVMRPDYLPSHRHSAVIPPSYRPTPD
451 YETVMKQLNRGLVHAERQSHSLRNLNIGSSYAYSRPAALVYSQPEIREHA
501 QLPSPAAAHCPFSLSYSFHSPSPYPYPAERRPVVGAVSVPELTNAQLQAQ
551 DYPSPNIMRTQVYRPPPPYPPPRPANSTPDLSRHLYISSSNPDLITRRVH
601 HSVQTFQEDSLPVAHSLQEVSEPLTAARHAQLHKRNSIEVAGLSHGLEGL
651 RLKERTLSASAAEVAPRAVSVGSQPSVFTERTQREGPEEAEGLRYGHKKS
701 LSDATMLIHSSEEEEDEDFEEESGARAPPARAREPRPGLAQDPPGCPRVL
751 LAGPLHILEPKAHVPDAEKRMMDSSPVRTTAEAQRPWRDGLLMPSMSESD
801 LTTSGRYRARRDSLKKRPVSDLLSGKKNIVEGLPPLGGMKKTRVDAKKIG
851 PLKLAALNGLSLSRVPLPDEGKEVATRATNDERCKILEQRLEQGMVFTEY
901 ERILKKRLVDGECSTARLPENAERNRFQDVLPYDDARVELVPTKENNTGY
951 INASHIKVSVSGIEWDYIATQGPLQNTCQDFWQMVWEQGIAIIAMVTAEE
1001 EGGREKSFRYWPRLGSRHNTVTYGRFKITTRFRTDSGCYATTGLKMKHLL
1051 TGQERIVWHLQYTDWPEHGCPEDLKGFLSYLEEIQSVRRHTNSTSDPQSP
1101 NPPLLVHCSAGVGRTGVVILSEIMIACLEHNEVLDIPRVLDMLRQQRMML
1151 VQTLCQYTFVYRVLIQFLKSSRLI
```

FIG.6

```
PTPD1    921   NAERNRFQDVLPYDDARVELVPTKENNTGYINASHIKVSV--SGIEWDYIATQGPLQNTC
PTPH1    670   NLDKNRYKDVLPYDTTRVLL----QGNEDYINASYVNMEIPAANLVNKYIATQGPLPHTC
PTPMEG1  679   NISKNRYRDISPYDATRVIL----KGNEDYINANYINMEIPSSSINQYIACQGPLPHTC

PTPD1    979   QDFWQMVWEQGIAITAMVTAEEEGGREKSFRYWPRLGSRHNTVTYGRFKITTRFRTDSGC
PTPH1    726   AQFWQMVWDQKLSLIVMLTIVMLTILTERGRTKCHQYWP----DPPDVMNHGGFHIQCQSEDCTIA
PTPMEG1  735   TDFWQMTWEQGSSMVVMLITQVERGRVKCHQYWP----EPTGSSSYGCYQVTCHSEEGNTA

PTPD1    1039  YATTGLKMKHLLLTGQERTVWHLQYTDWPEHGCPEDLKGFLSYLEEIQSVRRHTNSTSDPQ
PTPH1    783   YVSREMLVTNTQTGEEHTVTHLQYVAWPDHGIPDDSSDFLEFVNYVRSLRVDSE------
PTPMEG1  792   YIFRKMTLFNQEKNESRPLTQIQYIAWPDHGVPDDSSDFLDFVCHVRNKRAGKEE------

PTPD1    1099  SPNPPLLVHCSAGVGRTGVVILSEIMIACLEHNEVLDIP-RVLDMLRQQRMMLVQTLCQY
PTPH1    837   ----PVLVHCSAGIGRTGVLVTMETAM-CLTERNLPIYPLDIVRKMRDQRAMMVQTSSQY
PTPMEG1  847   ----PVVVHCSAGIGRTGVLITMETAM-CLIECNQPVVPLDIVRTMRDQRAMMIQTPSQY

PTPD1    1158  TFVYRVLIQ
PTPH1    892   KFVCEAILR
PTPMEG1  902   RFVCEAILK
```

FIG.7B

```
PTPD1     1   MPLPFGLKLKRTRRYTVSS------KSCLVARIQLLNEFVEFTLSVESTGQESLEAV
PTPH1     1   MTSRL---RALGGRINNIRTSELPKEKTRSEVICSIHFLDGVIQTFKVTKQDTGQVLDMV
PTPMEG1   1   MTSRF---RLPAGRTYNVRASELARDRQHTEVVQNILLDNTVQAFKVNKHDQGQVLDVV

PTPD1     53  AQRLELREVTYFSLWYYNKQ-NQRRWDLEKPLKKQLDKYALEPTVYFGVFYMPSVSQL
PTPH1     59  HNHLGVTEKEYFGLQHDDDSVDSPRWLEASKPIRKQL-KGGFPCTLHFRVRFFIPDPNTL
PTPMEG1   59  FKHLDITEQDYFGLQLADDSTDNPRWLDPNKPIRKQL-KRGSPYSLNFRVKFFVSDPNKL

PTPD1     112 QQEITRYQYYLQLKKDILEGSIPCTLEQAIQLAGLAVQADFGDFDQYESQ-DFLQKFALF
PTPH1     118 QQEQTRHLYFLQLKMDICEGRLITCPLNSAVVLASYAVQSHFGDYNSSIHHPGYLSDSHFI
PTPMEG1   118 QEEYTRYQYFLQIKQDILTGRLPCPSNTAALLASFAVQSELGDYDQSENLSGYLSDYSFI

PTPD1     171 PVGWLQDEKVLEEATQKVALLHQKYRGLTAPDAEMLYMQEVERMDGYGEESYPAKDSQGS
PTPH1     178 P------DQNEDFLTKVESLHEQHSGLKQSEAESCYINIARTLDFYGVELHSGRDLHNL
PTPMEG1   178 P------NQPQDFEKETAKLHQQHIGLSPAEAEFNYLNTARTLELYGVEFHYARDQSNN

PTPD1     231 DISIGACLEGIFVKHKNGRHPVVFRWHDIANMSHN-KSFFALE----LANKEETIQFQTE
PTPH1     231 DLMIGIASAGVAV-YRKYICTSFYPWVNILKISFKRKKFFIHQRQKQAESREHIVAFML
PTPMEG1   231 EIMIGVMSGGILI-YKNRVRMNTFPMLKIVKISFCKKQFFIQLRKELHESRETLLGFNMV

PTPD1     286 DMETAKYIWRLCVARHKFYRLNQCNLQTQTVTVN----PIRRRSSSRMSLPKPQPYVM
PTPH1     290 NYRSCKNLWKSCVEHTFFQAKKLLPQEKNVLSQYWTMGSRN---TKKSVNN-Q-YCK
PTPMEG1   290 NYRACKNLWKACVEHTFFRLDRPLPPQKNFFAHYFTLGSKFRYCGRTEVQSVQ-YGK
```

FIG.7C

```
                        SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 6
        (D) OTHER INFORMATION: /note= "X = S or N"

(xi) SEQUENCE DESCRIPTION: SEQ ID NO:1:

Asp Tyr Ile Asn Ala Xaa
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:2:

Cys Xaa Xaa Tyr Trp Pro
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 1
        (D) OTHER INFORMATION: /note= "X = I or V"

(xi) SEQUENCE DESCRIPTION: SEQ ID NO:3:

Xaa Val Met Xaa Xaa Xaa Xaa Glu
```

```
1               5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 1
        (D) OTHER INFORMATION: /note= "X = D or N"

(ix) FEATURE:
        (A) NAME/KEY: Region
        (B) LOCATION: 6
        (D) OTHER INFORMATION: /note= "X = S or N"

(xi) SEQUENCE DESCRIPTION: SEQ ID NO:4:

Xaa Tyr Ile Asn Ala Xaa
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 6
        (D) OTHER INFORMATION: /note= "X = S or N"

(xi) SEQUENCE DESCRIPTION: SEQ ID NO:5:

Gly Tyr Ile Asn Ala Xaa
1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:6:

Ser Xaa Xaa Tyr Trp Pro
1               5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:7:

Ile Ala Met Val Xaa Xaa Xaa Xaa Glu
1               5
```

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 6
        (D) OTHER INFORMATION: /note= "X = S or N"

(xi) SEQUENCE DESCRIPTION: SEQ ID NO:8:

Asn Tyr Ile Asn Ala Xaa
1           5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 1
        (D) OTHER INFORMATION: /note= "X = I or V or L"

(ix) FEATURE:
        (A) NAME/KEY: Region
        (B) LOCATION: 3
        (D) OTHER INFORMATION: /note= "X = M or I or L"

(ix) FEATURE:
        (A) NAME/KEY: Region
        (B) LOCATION: 4
        (D) OTHER INFORMATION: /note= "X = V or L or I or M"

(xi) SEQUENCE DESCRIPTION: SEQ ID NO:9:

Xaa Val Xaa Xaa Xaa Xaa Xaa Xaa Glu
1           5

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AYTTYTGGVR RATGRTNTGG                                   20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CCNAYDCCHG CRCTRCAGTG                                                          20
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:12:

```
Phe Trp Xaa Met Xaa Trp
1               5
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Region
        (B) LOCATION: 6
        (D) OTHER INFORMATION: /note= "X = S or I or V"

(xi) SEQUENCE DESCRIPTION: SEQ ID NO:13:

```
His Cys Ser Ala Gly Xaa Gly
1               5
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ATAGCAATGG TGACAGCAGA A                                                        21
```

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:15:

```
Cys Tyr Ala Thr Thr Gly
1               5
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AGNCCNGTNG TNGCRTARCA                                                    20

(2) INFORMATION FOR SEQ ID NO:17:

(i) SEQUENCE CHARACTERISTICS:
            (A) LENGTH: 6 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:17:

Gln Glu Arg Thr Val Trp
1               5

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

GGTNACNGTN CKYTCYT                                                       17

(2) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

ATAGCAATGG TGACAGCAGA A                                                  21

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CGCCCRAYNC CNGCNCTRCA GTG                                                23

(2) INFORMATION FOR SEQ ID NO:21:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

```
GATCTCCGAA TTCCATGGAT CCAGGCCTCT AGAAGCTTAC                              40
```

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
AGGCTTAAGG TACCTAGGTC CGGAGATCTT CGAATGTTAA                              40
```

(2) INFORMATION FOR SEQ ID NO:23:

(i) SEQUENCE CHARACTERISTICS:
        (A) LENGTH: 261 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO:23:

```
TTTTGGCAGA TGGTATGGGA ACAGGGAATT GCAATTATAG CAATGGTGAC AGCAGAAGAG        60

GAGGGTNGAN NGGAGAAGAG CTTTAGGTAC TGGCCACGAC TTGGTTCCAG GCACAACACT        120

GTCACCTATG GAAGGTTTAA GATCACGACC CGGTTCCGCA CAGACTCTGG CTGCTATGCC        180

ACCACAGGCC TGAAGATGAA GCACCTCCTT ACCGGGCAAG AGAGGACCGT CTGGCNNCTC        240

CAATACACAG ACTGGCCTGA A                                                  261
```

(2) INFORMATION FOR SEQ ID NO:24:

(i) SEQUENCE CHARACTERISTICS:
        (A) LENGTH: 87 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:24:

```
Phe Trp Gln Met Val Trp Glu Gln Gly Ile Ala Ile Ile Ala Met Val
 1               5                  10                  15

Thr Ala Glu Glu Glu Gly Xaa Xaa Glu Lys Ser Phe Arg Tyr Trp Pro
                20                  25                  30

Arg Leu Gly Ser Arg His Asn Thr Val Thr Tyr Gly Arg Phe Lys Ile
            35                  40                  45

Thr Thr Arg Phe Arg Thr Asp Ser Gly Cys Tyr Ala Thr Thr Gly Leu
        50                  55                  60

Lys Met Lys His Leu Leu Thr Gly Gln Glu Arg Thr Val Trp Xaa Leu
65                  70                  75                  80

Gln Tyr Thr Asp Trp Pro Glu
                85
```

(2) INFORMATION FOR SEQ ID NO:25:

(i) SEQUENCE CHARACTERISTICS:
        (A) LENGTH: 270 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO:25:

TTCTGGCGGA TGATCTGGGA GCAGGGAGTG AATGTGATTG CCATGGTCAC TGCAGAGGAG      60

GAGGGTGGAC GAACCAAAAG CCACCGATAC TGGCCCAAAC TAGGTTCAAA GCACAGCTCA     120

GCCACCTATG GCAAGTTCAA GGTCACCACG AAGTTTCGAA CGGATTCTGT TTGCTATGCA     180

ACCACGGGCT TGAAGGTCAA GCACCTTTTG TCTGGGNAAG AAAGGACGGT GTGGCATTTA     240

CAATATACTG ACTGGCCTGA CTTCGGCGCC                                      270

(2) INFORMATION FOR SEQ ID NO:26:

(i) SEQUENCE CHARACTERISTICS:
            (A) LENGTH: 90 amino acids
            (B) TYPE: amino acid
            (C) STRANDEDNESS: single
            (D) TOPOLOGY: unknown (ii) MOLECULE TYPE: protein (xi) SEQUENCE DESCRIPTION: SEQ ID NO:26:

Phe Trp Arg Met Ile Trp Glu Gln Gly Val Asn Val Ile Ala Met Val
1               5                   10                  15

Thr Ala Glu Glu Glu Gly Gly Arg Thr Lys Ser His Arg Tyr Trp Pro
            20                  25                  30

Lys Leu Gly Ser Lys His Ser Ser Ala Thr Tyr Gly Lys Phe Lys Val
        35                  40                  45

Thr Thr Lys Phe Arg Thr Asp Ser Val Cys Tyr Ala Thr Thr Gly Leu
50                  55                  60

Lys Val Lys His Leu Leu Ser Gly Xaa Glu Arg Thr Val Trp His Leu
65                  70                  75                  80

Gln Tyr Thr Asp Trp Pro Asp Phe Gly Ala
                85                  90

(2) INFORMATION FOR SEQ ID NO:27:

(i) SEQUENCE CHARACTERISTICS:
            (A) LENGTH: 120 amino acids
            (B) TYPE: amino acid
            (C) STRANDEDNESS: single
            (D) TOPOLOGY: unknown (ii) MOLECULE TYPE: protein (xi) SEQUENCE DESCRIPTION: SEQ ID NO:27:

Met Val Trp Glu Gln Lys Ser Arg Gly Val Val Met Leu Asn Arg Val
1               5                   10                  15

Met Glu Lys Gly Ser Leu Lys Cys Ala Gln Tyr Trp Pro Gln Lys Glu
            20                  25                  30

Glu Lys Glu Met Ile Phe Glu Asp Thr Asn Leu Lys Leu Thr Leu Ile
        35                  40                  45

Ser Glu Asp Ile Lys Ser Tyr Tyr Thr Val Arg Gln Leu Glu Leu Glu
50                  55                  60

Asn Leu Thr Thr Gln Glu Thr Arg Glu Ile Leu His Phe His Tyr Thr
65                  70                  75                  80

Thr Trp Pro Asp Phe Gly Val Pro Glu Ser Pro Ala Ser Phe Leu Asn
            85                  90                  95

Phe Leu Phe Lys Val Arg Glu Ser Gly Ser Leu Ser Pro Glu His Gly
        100                 105                 110

Pro Val Val Val His Cys Ser Ala

```
              115                 120
```

(2) INFORMATION FOR SEQ ID NO:28:

(i) SEQUENCE CHARACTERISTICS:
        (A) LENGTH: 89 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:28:

```
Met Val Trp Glu Gln Gly Ile Ala Ile Ile Ala Met Val Thr Ala Glu
1               5                  10                  15

Glu Glu Gly Xaa Xaa Glu Lys Ser Phe Arg Tyr Trp Pro Arg Leu Gly
            20                  25                  30

Thr Arg His Asn Thr Val Thr Tyr Gly Arg Phe Lys Ile Thr Thr Arg
        35                  40                  45

Phe Arg Thr Asp Ser Gly Cys Tyr Ala Thr Thr Gly Leu Lys Met Lys
    50                  55                  60

His Leu Leu Thr Gly Gln Glu Arg Thr Val Trp Xaa Leu Gln Tyr Thr
65                  70                  75                  80

Asp Trp Pro Glu His Gly Cys Pro Glu
                85
```

(2) INFORMATION FOR SEQ ID NO:29:

(i) SEQUENCE CHARACTERISTICS:
        (A) LENGTH: 87 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:29:

```
Met Ile Trp Glu Gln Gly Val Asn Val Ile Ala Met Val Thr Ala Glu
1               5                  10                  15

Glu Glu Gly Gly Arg Thr Lys Ser His Arg Tyr Trp Pro Lys Leu Gly
            20                  25                  30

Ser Lys His Ser Ser Ala Thr Tyr Gly Lys Phe Lys Val Thr Thr Lys
        35                  40                  45

Phe Arg Thr Asp Ser Val Cys Tyr Ala Thr Thr Gly Leu Lys Val Lys
    50                  55                  60

His Leu Leu Ser Gly Xaa Glu Arg Thr Val Trp His Leu Gln Tyr Thr
65                  70                  75                  80

Asp Trp Pro Asp Phe Gly Ala
                85
```

(2) INFORMATION FOR SEQ ID NO:30:

(i) SEQUENCE CHARACTERISTICS:
        (A) LENGTH: 300 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO:30:

```
GATTTTTGGC AGATGGTATG GGAACAGGGA ATTGCAATTA TAGCAATGGT GACAGCAGAA        60

GAGGAGGGTN GANNGGAGAA GAGCTTTAGG TACTGGCCAC GACTTGGTTC CAGGCACAAC       120
```

```
ACTGTCACCT ATGGAAGGTT TAAGATCACG ACCCGGTTCC GCACAGACTC TGGCTGCTAT        180

GCCACCACAG GCCTGAAGAT GAAGCACCTC CTTACCGGGC AAGAGAGGAC CGTCTGGCNN        240

CTCCAATACA CAGACTGGCC TGAACATGGC TGTCCAGAAG ACCTCAAGGG ATTTTTATCA        300
```

(2) INFORMATION FOR SEQ ID NO:31:

(i) SEQUENCE CHARACTERISTICS:
        (A) LENGTH: 270 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO:31:

```
TTCTGGCGGA TGATCTGGGA GCAGGGAGTG AATGTGATTG CCATGGTCAC TGCAGAGGAG         60

GAGGGTGGAC GAACCAAAAG CCACCGATAC TGGCCCAAAC TAGGTTCAAA GCACAGCTCA        120

GCCACCTATG GCAAGTTCAA GGTCACCACG AAGTTTCGAA CGGATTCTGT TTGCTATGCA        180

ACCACGGGCT TGAAGGTCAA GCACCTTTTG TCTGGGNAAG AAAGGACGGT GTGGCATTTA        240

CAATATACTG ACTGGCCTGA CTTCGGCGCC                                         270
```

(2) INFORMATION FOR SEQ ID NO:32:

(i) SEQUENCE CHARACTERISTICS:
        (A) LENGTH: 150 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:32:

```
Glu Trp Asp Tyr Ile Ala Thr Gln Gly Pro Leu Gln Asn Thr Cys Gln
1               5                  10                  15

Asp Phe Trp Gln Met Val Trp Glu Gln Gly Ile Ala Ile Ala Met
            20                  25                  30

Val Thr Ala Glu Glu Gly Xaa Xaa Glu Lys Ser Phe Arg Tyr Trp
        35                  40                  45

Pro Arg Leu Gly Ser Arg His Asn Thr Val Thr Tyr Gly Arg Phe Lys
50                  55                  60

Ile Thr Thr Arg Phe Arg Thr Asp Ser Gly Cys Tyr Ala Thr Thr Gly
65                  70                  75                  80

Leu Lys Met Lys His Leu Leu Thr Gly Gln Glu Arg Thr Val Trp Xaa
                85                  90                  95

Leu Gln Tyr Thr Asp Trp Pro Glu His Gly Cys Pro Glu Asp Leu Lys
            100                 105                 110

Gly Phe Leu Ser Tyr Leu Glu Glu Ile Gln Ser Val Arg Arg His Thr
            115                 120                 125

Asn Ser Thr Ser Asp Pro Gln Ser Pro Asn Pro Leu Leu Val Xaa
        130                 135                 140

Cys Ser Ala Gly Val Gly
145                 150
```

(2) INFORMATION FOR SEQ ID NO:33:

(i) SEQUENCE CHARACTERISTICS:
        (A) LENGTH: 878 base pairs
        (B) TYPE: nucleic acid
        (C) STRANDEDNESS: both (D) TOPOLOGY: unknown (ii) MOLECULE TYPE: cDNA (xi) SEQUENCE DESCRIPTION: SEQ ID NO:33:

| | | | | | |
|---|---|---|---|---|---|
| GAATTCTTAA | GAAACGGCTA | GTTGATGGGG | AGTGCTCAAC | AGCACGACTC | CCTGAAAATG | 60 |
| CAGAAAGAAA | TCGATTCCAA | GATGTTCTTC | CTTATGATGA | TGCGAGAGTG | GAGTTGGTCC | 120 |
| CAACTAAAGA | AAACAACACT | GGTTACATCA | ACGCATCACA | TATTAAGGTC | TCTGTCAGTG | 180 |
| GAATCGAATG | GGATTATATT | GCCACACAGG | GACCATTACA | GAATACCTGT | CAAGATTTTT | 240 |
| GGCAGATGGT | ATGGGAACAG | GGAATTGCAA | TTATAGCAAT | GGTGACAGCA | GAAGAGGAGG | 300 |
| GTNGANNGGA | GAAGAGCTTT | AGGTACTGGC | CACGACTTGG | TTCCAGGCAC | AACACTGTCA | 360 |
| CCTATGGAAG | GTTTAAGATC | ACGACCCGGT | TCCGCACAGA | CTCTGGCTGC | TATGCCACCA | 420 |
| CAGGCCTGAA | GATGAAGCAC | CTCCTTACCG | GGCAAGAGAG | GACCGTCTGG | CNNCTCCAAT | 480 |
| ACACAGACTG | GCCTGAACAT | GGCTGTCCAG | AAGACCTCAA | GGGATTTTTA | TCATATCTTG | 540 |
| AAGAGATCCA | GTCTGTTCGA | CGCCATACAA | ATAGCACAAG | TGATCCCCAA | AGCCCCAACC | 600 |
| CTCCGTTGTT | GGTCCACTGC | AGTGCTGGGG | TAGGAAGGAC | TGGCGTGGTG | ATTTTGTCGG | 660 |
| AGATCATGAT | CGCCTGCCTG | GAACACAATG | AGGTGCTGGA | CATCCCGAGA | GTGCTGGACA | 720 |
| TGCTGAGGCA | ACAGAGAATG | ATGCTGGTGC | AGACTCTCTG | CCAGTACACA | TTTGTGTACA | 780 |
| GAGTCCTCAT | CCAGTTCCTG | AAAAGCTCCA | GGCTCATCTA | AGCTCCCACA | ATTTCTTACG | 840 |
| GGGCCAGTCA | TGTGAAGCGT | TTACAGCTTA | AAAAAAAA | | | 878 |

(2) INFORMATION FOR SEQ ID NO:34:

(i) SEQUENCE CHARACTERISTICS:
  (A) LENGTH: 272 amino acids
  (B) TYPE: amino acid
  (C) STRANDEDNESS: single
  (D) TOPOLOGY: unknown (ii) MOLECULE TYPE: protein (xi) SEQUENCE DESCRIPTION: SEQ ID NO:34:

Ile Leu Lys Lys Arg Leu Val Asp Gly Glu Cys Ser Thr Ala Arg Leu
 1               5                  10                  15

Pro Glu Asn Ala Glu Arg Asn Arg Phe Gln Asp Val Leu Pro Tyr Asp
                20                  25                  30

Asp Ala Arg Val Glu Leu Val Pro Thr Lys Glu Asn Asn Thr Gly Tyr
            35                  40                  45

Ile Asn Ala Ser His Ile Lys Val Ser Val Ser Gly Ile Glu Trp Asp
        50                  55                  60

Tyr Ile Ala Thr Gln Gly Pro Leu Gln Asn Thr Cys Gln Asp Phe Trp
65                  70                  75                  80

Gln Met Val Trp Glu Gln Gly Ile Ala Ile Ala Met Val Thr Ala
                85                  90                  95

Glu Glu Glu Gly Xaa Xaa Glu Lys Ser Phe Arg Tyr Trp Pro Arg Leu
            100                 105                 110

Gly Ser Arg His Asn Thr Val Thr Tyr Gly Arg Phe Lys Ile Thr Thr
        115                 120                 125

Arg Phe Arg Thr Asp Ser Gly Cys Tyr Ala Thr Thr Gly Leu Lys Met
    130                 135                 140

Lys His Leu Leu Thr Gly Gln Glu Arg Thr Val Trp Xaa Leu Gln Tyr
145                 150                 155                 160

Thr Asp Trp Pro Glu His Gly Cys Pro Glu Asp Leu Lys Gly Phe Leu

|  |  | 165 |  |  |  | 170 |  |  |  | 175 |  |
|---|---|---|---|---|---|---|---|---|---|---|---|

Ser Tyr Leu Glu Glu Ile Gln Ser Val Arg Arg His Thr Asn Ser Thr
            180                     185                 190

Ser Asp Pro Gln Ser Pro Asn Pro Pro Leu Leu Val His Cys Ser Ala
            195                 200                 205

Gly Val Gly Arg Thr Gly Val Val Ile Leu Ser Glu Ile Met Ile Ala
            210                 215                 220

Cys Leu Glu His Asn Glu Val Leu Asp Ile Pro Arg Val Leu Asp Met
225                 230                 235                 240

Leu Arg Gln Gln Arg Met Met Leu Val Gln Thr Leu Cys Gln Tyr Thr
                245                 250                 255

Phe Val Tyr Arg Val Leu Ile Gln Phe Leu Lys Ser Ser Arg Leu Ile
            260                 265                 270

(2) INFORMATION FOR SEQ ID NO:35:

(i) SEQUENCE CHARACTERISTICS:
        (A) LENGTH: 4080 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO:35:

```
GCCCATGAGC GCGCCGCGGC CCGGGCTGGC GTGCGGGTGC GGCTGCGGCG GCCGCGCGGC         60
GGGGCCCCGG GAGGCGGGTC GCTGAGCGGG GCGCGCGGCC CCGAGGATGC GGGAGCGGGA        120
GCGGGAGCAG CGCTGGCGTC AATGCTCCCT TCCTCGGGCC ATTGGAGACT CCGTTGCTTT        180
TTAATGGCGG CAGCGGCTGC TGGGTGAGCA GCTGGAGGCC GGACAGTGTT CGTCCCATCC        240
GGAGAGGATC GCTTTCTCCT GGCGTCACCA GCGCTGGGTT GGTGGGGGTA GCTTTTCCCT        300
CTTTGCTCCT CCATTCTTGA AGAAAGAAGA AGATGCCACT GCCATTTGGG TTGAAACTGA        360
AACGCACCCG GCGCTACACG GTGTCCAGCA AGAGTTGCCT GGTTGCCCGG ATCCAACTGC        420
TTAATAACGA GTTTGTGGAG TTCACCCTGT CCGTGGAGAG CACTGGCCAG GAAAGCCTCG        480
AGGCCGTGGC CCAGAGGCTG GAGCTGCGGG AGGTCACTTA CTTCAGCCTC TGGTACTACA        540
ACAAGCAAAA TCAGCGCCGG TGGGTAGATT TGGAAAAACC TTTGAAGAAG CAGCTGGATA        600
AATATGCATT GGAACCTACC GTCTATTTTG GAGTGGTGTT TTATGTGCCT TCAGTTTCTC        660
AGCTGCAGCA GGAGATTACC AGGTATCAGT ATTATCTGCA ACTGAAGAAA GATATCTTGG        720
AAGGAAGTAT TCCTTGTACC TTAGAACAAG CAATTCAGCT AGCAGGCTTA GCTGTTCAAG        780
CGGATTTTGG TGACTTTGAT CAGTATGAAT CCCAGGACTT TCTTCAGAAA TTTGCCTTGT        840
TTCCTGTGGG ATGGTTACAA GATGAAAAAG TATTGGAAGA AGCAACCCAA AAAGTGGCCT        900
TACTACATCA GAAATACAGA GGGCTCACAG CTCCTGATGC TGAAATGCTG TACATGCAGG        960
AGGTAGAGAG AATGGATGGC TATGGAGAAG AGAGCTACCC TGCTAAGGAT AGCCAAGGAA       1020
GTGACATATC CATTGGAGCG TGTCTTGAAG GTATCTTTGT GAAACACAAG AATGGAAGGC       1080
ATCCTGTGGT ATTTAGGTGG CATGACATTG CCAACATGTC CCACAACAAG TCCTTTTTTG       1140
CATTAGAGCT GGCAAATAAA GAGGAGACCA TTCAATTTCA AACTGAAGAC ATGGAAACAG       1200
CAAAATACAT TTGGAGACTC TGTGTTGCGC GACACAAGTT TTACAGACTA AACCAGTGTA       1260
ACCTGCAAAC TCAGACTGTC ACAGTGAACC CAATCAGGAG GAGGTCTTCT TCAAGGATGT       1320
CTCTGCCTAA ACCCCAGCCC TACGTGATGC CTCCCCCACC GCAGTTGCAC TATAATGGAC       1380
ATTATACAGA ACCATATGCT TCTTCCCAAG ATAACCTCTT TGTGCCCAAC CAGAACGGAT       1440
```

```
ACTACTGTCA CTCTCAGACA AGCTTGGATA GAGCCCAGAT TGACTTCAAC GGTCGGATCC      1500

GTAATGGCAG TGTCTACAGT GCACACAGCA CCAACTCCTT AAATAATCCT CAGCCCTACT      1560

TGCAGCCCTC GCCGATGTCG TCCAACCCTA GCATCACCGG GAGTGACGTC ATGAGGCCTG      1620

ACTACCTCCC GTCCCATCGG CACAGCGCCG TGATACCCCC GTCCTACCGC CCCACCCCAG      1680

ACTATGAGAC TGTGATGAAG CAGCTCAACA GGGGCCTGGT GCATGCGGAA CGGCAGAGCC      1740

ACTCGCTGCG AAACCTCAAC ATCGGCAGCT CGTACGCCTA CAGCAGGCCC GCGGCGCTGG      1800

TCTACAGCCA GCCCGAGATC CGCGAGCACG CACAGCTCCC CTCGCCAGCG GCCGCACACT      1860

GCCCGTTCAG CCTGAGCTAC AGCTTCCACA GCCCGTCTCC CTACCCCTAC CCTGCCGAGC      1920

GGCGGCCCGT GGTGGGCGCG GTCAGCGTGC CGGAGCTGAC CAATGCGCAG CTGCAGGCGC      1980

AGGACTACCC GTCTCCCAAC ATCATGCGGA CGCAGGTGTA CCGGCCACCC CCACCCTACC      2040

CGCCCCCCAG GCCCGCCAAC AGCACGCCAG ACCTGTCCCG CCACCTTTAC ATCAGCAGCA      2100

GCAACCCCGA CCTCATCACG CGGCGCGTGC ACCACTCGGT GCAAACGTTC AGGAGGACA       2160

GCCTGCCCGT GGCGCACTCG CTGCAGGAGG TCAGCGAGCC CCTCACCGCC GCGCGCCACG      2220

CGCAGCTGCA CAAACGGAAC AGCATCGAGG TGGCCGGGCT CAGCCACGGC CTGGAGGGCC      2280

TGCGGCTCAA GGAGCGCACC CTATCCGCGT CGGCGGCAGA GGTGGCGCCG CGAGCCGTCT      2340

CGGTGGGCTC CCAGCCCAGC GTTTTCACCG AGAGGACACA GCGAGAAGGG CCGGAGGAGG      2400

CGGAGGGCTT GAGGTACGGC CATAAGAAGT CCCTGTCGGA CGCCACCATG CTAATCCACA      2460

GCAGCGAGGA GGAGGAGGAC GAGGACTTCG AGGAGGAGAG CGGGGCCCGG GCGCCCCCTG      2520

CACGTGCGCG CGAGCCTCGG CCCGGCCTGG CCCAGGACCC ACCTGGCTGC CCTCGCGTCC      2580

TGCTCGCCGG GCCCCTGCAC ATCCTGGAGC CCAAGGCCCA CGTCCCAGAC GCGGAGAAGA      2640

GGATGATGGA CAGCAGCCCC GTCCGCACGA CCGCAGAGGC CCAGCGGCCC TGGAGAGACG      2700

GGCTGCTGAT GCCCTCCATG TCGGAGTCCG ACCTCACCAC GTCAGGCCGC TACCGAGCCC      2760

GGAGGGACTC TCTGAAGAAA AGGCCGGTGT CGGACCTTCT CTCTGGGAAG AAGAACATCG      2820

TGGAAGGGCT CCCGCCTCTA GGGGGAATGA AAAAGACTCG AGTAGATGCA AAAAAAATTG      2880

GTCCTCTTAA ACTGGCTGCC CTAAATGGAC TCTCCCTATC TCGAGTGCCT CTGCCTGATG      2940

AAGGAAAGGA AGTGGCTACC AGAGCAACGA ATGATGAAAG GTGTAAAATT CTGGAACAAC      3000

GATTAGAACA AGGAATGGTA TTCACAGAAT ATGAAAGAAT TCTTAAGAAA CGGCTAGTTG      3060

ATGGGGAGTG CTCAACAGCA CGACTCCCTG AAAATGCAGA AAGAAATCGA TTCCAAGATG      3120

TTCTTCCTTA TGATGATGCG AGAGTGGAGT TGGTCCCAAC TAAAGAAAAC AACACTGGTT      3180

ACATCAACGC ATCACATATT AAGGTCTCTG TCAGTGGAAT CGAATGGGAT TATATTGCCA      3240

CACAGGGACC ATTACAGAAT ACCTGTCAAG ATTTTTGGCA GATGGTATGG GAACAGGGAA      3300

TTGCAATTAT AGCAATGGTG ACAGCAGAAG AGGAGGGTGG AAGGGAGAAG AGCTTTAGGT      3360

ACTGGCCACG ACTTGGTTCC AGGCACAACA CTGTCACCTA TGGAAGGTTT AAGATCACGA      3420

CCCGGTTCCG CACAGACTCT GGCTGCTATG CCACCACAGG CCTGAAGATG AAGCACCTCC      3480

TTACCGGGCA AGAGAGGACC GTCTGGCACC TCCAATACAC AGACTGGCCT GAACATGGCT      3540

GTCCAGAAGA CCTCAAGGGA TTTTTATCAT ATCTTGAAGA GATCCAGTCT GTTCGACGCC      3600

ATACAAATAG CACAAGTGAT CCCCAAAGCC CCAACCCTCC GTTGTTGGTC CACTGCAGTG      3660

CTGGGGTAGG AAGGACTGGC GTGGTGATTT TGTCGGAGAT CATGATCGCC TGCCTGGAAC      3720

ACAATGAGGT GCTGGACATC CCGAGAGTGC TGGACATGCT GAGGCAACAG AGAATGATGC      3780

TGGTGCAGAC TCTCTGCCAG TACACATTTG TGTACAGAGT CCTCATCCAG TTCCTGAAAA      3840
```

```
GCTCCAGGCT CATCTAAGCT CCCACAATTT CTTACGGGGC CAGTCATGTG AAGCGTTTAC    3900

AGCTTAAAAA AAAAGCGCTT GCCTAACTCA TACTTTCCCG TTGACACTTG ATCCACGCAG    3960

CGTGGCACTG GGACGTAAGT GGCGCAGTCT GAATGGCGGA ACGCTGAAGG AAACGTGCGA    4020

AGCACAGGCT GAAGAGGGGT TTCTAACCTG GGAAAGGTGC TCAAGGAGGA CTTGGTTTCA    4080
```

(2) INFORMATION FOR SEQ ID NO:36:

(i) SEQUENCE CHARACTERISTICS:
        (A) LENGTH: 1174 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:36:

```
Met Pro Leu Pro Phe Gly Leu Lys Leu Lys Arg Thr Arg Arg Tyr Thr
1               5                   10                  15

Val Ser Ser Lys Ser Cys Leu Val Ala Arg Ile Gln Leu Leu Asn Asn
            20                  25                  30

Glu Phe Val Glu Phe Thr Leu Ser Val Glu Ser Thr Gly Gln Glu Ser
        35                  40                  45

Leu Glu Ala Val Ala Gln Arg Leu Glu Leu Arg Glu Val Thr Tyr Phe
50                  55                  60

Ser Leu Trp Tyr Tyr Asn Lys Gln Asn Gln Arg Arg Trp Val Asp Leu
65                  70                  75                  80

Glu Lys Pro Leu Lys Lys Gln Leu Asp Lys Tyr Ala Leu Glu Pro Thr
            85                  90                  95

Val Tyr Phe Gly Val Val Phe Tyr Val Pro Ser Val Ser Gln Leu Gln
            100                 105                 110

Gln Glu Ile Thr Arg Tyr Gln Tyr Tyr Leu Gln Leu Lys Lys Asp Ile
            115                 120                 125

Leu Glu Gly Ser Ile Pro Cys Thr Leu Glu Gln Ala Ile Gln Leu Ala
            130                 135                 140

Gly Leu Ala Val Gln Ala Asp Phe Gly Asp Phe Asp Gln Tyr Glu Ser
145                 150                 155                 160

Gln Asp Phe Leu Gln Lys Phe Ala Leu Phe Pro Val Gly Trp Leu Gln
            165                 170                 175

Asp Glu Lys Val Leu Glu Ala Thr Gln Lys Val Ala Leu Leu His
            180                 185                 190

Gln Lys Tyr Arg Gly Leu Thr Ala Pro Asp Ala Glu Met Leu Tyr Met
            195                 200                 205

Gln Glu Val Glu Arg Met Asp Gly Tyr Gly Glu Ser Tyr Pro Ala
            210                 215                 220

Lys Asp Ser Gln Gly Ser Asp Ile Ser Ile Gly Ala Cys Leu Glu Gly
225                 230                 235                 240

Ile Phe Val Lys His Lys Asn Gly Arg His Pro Val Val Phe Arg Trp
            245                 250                 255

His Asp Ile Ala Asn Met Ser His Asn Lys Ser Phe Phe Ala Leu Glu
            260                 265                 270

Leu Ala Asn Lys Glu Glu Thr Ile Gln Phe Gln Thr Glu Asp Met Glu
            275                 280                 285

Thr Ala Lys Tyr Ile Trp Arg Leu Cys Val Ala Arg His Lys Phe Tyr
            290                 295                 300

Arg Leu Asn Gln Cys Asn Leu Gln Thr Gln Thr Val Thr Val Asn Pro
```

```
              305                 310                 315                 320
Ile Arg Arg Arg Ser Ser Arg Met Ser Leu Pro Lys Pro Gln Pro
                325                 330                 335

Tyr Val Met Pro Pro Pro Gln Leu His Tyr Asn Gly His Tyr Thr
            340                 345                 350

Glu Pro Tyr Ala Ser Ser Gln Asp Asn Leu Phe Val Pro Asn Gln Asn
                355                 360                 365

Gly Tyr Tyr Cys His Ser Gln Thr Ser Leu Asp Arg Ala Gln Ile Asp
    370                 375                 380

Phe Asn Gly Arg Ile Arg Asn Gly Ser Val Tyr Ser Ala His Ser Thr
385                 390                 395                 400

Asn Ser Leu Asn Asn Pro Gln Pro Tyr Leu Gln Pro Ser Pro Met Ser
                405                 410                 415

Ser Asn Pro Ser Ile Thr Gly Ser Asp Val Met Arg Pro Asp Tyr Leu
                420                 425                 430

Pro Ser His Arg His Ser Ala Val Ile Pro Pro Ser Tyr Arg Pro Thr
            435                 440                 445

Pro Asp Tyr Glu Thr Val Met Lys Gln Leu Asn Arg Gly Leu Val His
    450                 455                 460

Ala Glu Arg Gln Ser His Ser Leu Arg Asn Leu Asn Ile Gly Ser Ser
465                 470                 475                 480

Tyr Ala Tyr Ser Arg Pro Ala Ala Leu Val Tyr Ser Gln Pro Glu Ile
                485                 490                 495

Arg Glu His Ala Gln Leu Pro Ser Pro Ala Ala His Cys Pro Phe
                500                 505                 510

Ser Leu Ser Tyr Ser Phe His Ser Pro Ser Pro Tyr Pro Tyr Pro Ala
            515                 520                 525

Glu Arg Arg Pro Val Val Gly Ala Val Ser Val Pro Glu Leu Thr Asn
    530                 535                 540

Ala Gln Leu Gln Ala Gln Asp Tyr Pro Ser Pro Asn Ile Met Arg Thr
545                 550                 555                 560

Gln Val Tyr Arg Pro Pro Pro Tyr Pro Pro Arg Pro Ala Asn
                565                 570                 575

Ser Thr Pro Asp Leu Ser Arg His Leu Tyr Ile Ser Ser Asn Pro
            580                 585                 590

Asp Leu Ile Thr Arg Arg Val His His Ser Val Gln Thr Phe Gln Glu
            595                 600                 605

Asp Ser Leu Pro Val Ala His Ser Leu Gln Glu Val Ser Glu Pro Leu
    610                 615                 620

Thr Ala Ala Arg His Ala Gln Leu His Lys Arg Asn Ser Ile Glu Val
625                 630                 635                 640

Ala Gly Leu Ser His Gly Leu Glu Gly Leu Arg Leu Lys Glu Arg Thr
            645                 650                 655

Leu Ser Ala Ser Ala Ala Glu Val Ala Pro Arg Ala Val Ser Val Gly
            660                 665                 670

Ser Gln Pro Ser Val Phe Thr Glu Arg Thr Gln Arg Glu Gly Pro Glu
            675                 680                 685

Glu Ala Glu Gly Leu Arg Tyr Gly His Lys Lys Ser Leu Ser Asp Ala
    690                 695                 700

Thr Met Leu Ile His Ser Ser Glu Glu Glu Asp Glu Asp Phe Glu
705                 710                 715                 720

Glu Glu Ser Gly Ala Arg Ala Pro Pro Ala Arg Ala Arg Glu Pro Arg
                725                 730                 735
```

```
Pro Gly Leu Ala Gln Asp Pro Pro Gly Cys Pro Arg Val Leu Leu Ala
        740                 745                 750

Gly Pro Leu His Ile Leu Glu Pro Lys Ala His Val Pro Asp Ala Glu
        755                 760                 765

Lys Arg Met Met Asp Ser Ser Pro Val Arg Thr Thr Ala Glu Ala Gln
770                 775                 780

Arg Pro Trp Arg Asp Gly Leu Leu Met Pro Ser Met Ser Glu Ser Asp
785                 790                 795                 800

Leu Thr Thr Ser Gly Arg Tyr Arg Ala Arg Arg Asp Ser Leu Lys Lys
                805                 810                 815

Arg Pro Val Ser Asp Leu Leu Ser Gly Lys Lys Asn Ile Val Glu Gly
                820                 825                 830

Leu Pro Pro Leu Gly Gly Met Lys Lys Thr Arg Val Asp Ala Lys Lys
                835                 840                 845

Ile Gly Pro Leu Lys Leu Ala Ala Leu Asn Gly Leu Ser Leu Ser Arg
850                 855                 860

Val Pro Leu Pro Asp Glu Gly Lys Glu Val Ala Thr Arg Ala Thr Asn
865                 870                 875                 880

Asp Glu Arg Cys Lys Ile Leu Glu Gln Arg Leu Glu Gln Gly Met Val
                885                 890                 895

Phe Thr Glu Tyr Glu Arg Ile Leu Lys Lys Arg Leu Val Asp Gly Glu
                900                 905                 910

Cys Ser Thr Ala Arg Leu Pro Glu Asn Ala Glu Arg Asn Arg Phe Gln
                915                 920                 925

Asp Val Leu Pro Tyr Asp Asp Ala Arg Val Glu Leu Val Pro Thr Lys
                930                 935                 940

Glu Asn Asn Thr Gly Tyr Ile Asn Ala Ser His Ile Lys Val Ser Val
945                 950                 955                 960

Ser Gly Ile Glu Trp Asp Tyr Ile Ala Thr Gln Gly Pro Leu Gln Asn
                965                 970                 975

Thr Cys Gln Asp Phe Trp Gln Met Val Trp Glu Gln Gly Ile Ala Ile
                980                 985                 990

Ile Ala Met Val Thr Ala Glu Glu Gly Gly Arg Glu Lys Ser Phe
                995                 1000                1005

Arg Tyr Trp Pro Arg Leu Gly Ser Arg His Asn Thr Val Thr Tyr Gly
        1010                1015                1020

Arg Phe Lys Ile Thr Thr Arg Phe Arg Thr Asp Ser Gly Cys Tyr Ala
1025                1030                1035                1040

Thr Thr Gly Leu Lys Met Lys His Leu Leu Thr Gly Gln Glu Arg Thr
                1045                1050                1055

Val Trp His Leu Gln Tyr Thr Asp Trp Pro Glu His Gly Cys Pro Glu
        1060                1065                1070

Asp Leu Lys Gly Phe Leu Ser Tyr Leu Glu Glu Ile Gln Ser Val Arg
        1075                1080                1085

Arg His Thr Asn Ser Thr Ser Asp Pro Gln Ser Pro Asn Pro Pro Leu
        1090                1095                1100

Leu Val His Cys Ser Ala Gly Val Gly Arg Thr Gly Val Val Ile Leu
1105                1110                1115                1120

Ser Glu Ile Met Ile Ala Cys Leu Glu His Asn Glu Val Leu Asp Ile
                1125                1130                1135

Pro Arg Val Leu Asp Met Leu Arg Gln Gln Arg Met Met Leu Val Gln
                1140                1145                1150

Thr Leu Cys Gln Tyr Thr Phe Val Tyr Arg Val Leu Ile Gln Phe Leu
                1155                1160                1165
```

```
Lys Ser Ser Arg Leu Ile
    1170
```

(2) INFORMATION FOR SEQ ID NO:37:

(i) SEQUENCE CHARACTERISTICS:
        (A) LENGTH: 231 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:37:

```
Asn Leu Asp Lys Asn Arg Tyr Lys Asp Val Leu Pro Tyr Asp Thr Thr
1               5                   10                  15

Arg Val Leu Leu Gln Gly Asn Glu Asp Tyr Ile Asn Ala Ser Tyr Val
            20                  25                  30

Asn Met Glu Ile Pro Ala Ala Asn Leu Val Asn Lys Tyr Ile Ala Thr
            35                  40                  45

Gln Gly Pro Leu Pro His Thr Cys Ala Gln Phe Trp Gln Val Val Trp
50                  55                  60

Asp Gln Lys Leu Ser Leu Ile Val Met Leu Thr Thr Leu Thr Glu Arg
65                  70                  75                  80

Gly Arg Thr Lys Cys His Gln Tyr Trp Pro Asp Pro Asp Val Met
                85                  90                  95

Asn His Gly Gly Phe His Ile Gln Cys Gln Ser Glu Asp Cys Thr Ile
                100                 105                 110

Ala Tyr Val Ser Arg Glu Met Leu Val Thr Asn Thr Gln Thr Gly Glu
            115                 120                 125

Glu His Thr Val Thr His Leu Gln Tyr Val Ala Trp Pro Asp His Gly
130                 135                 140

Ile Pro Asp Asp Ser Ser Asp Phe Leu Glu Phe Val Asn Tyr Val Arg
145                 150                 155                 160

Ser Leu Arg Val Asp Ser Glu Pro Val Leu Val His Cys Ser Ala Gly
                165                 170                 175

Ile Gly Arg Thr Gly Val Leu Val Thr Met Glu Thr Ala Met Cys Leu
            180                 185                 190

Thr Glu Arg Asn Leu Pro Ile Tyr Pro Leu Asp Ile Val Arg Lys Met
            195                 200                 205

Arg Asp Gln Arg Ala Met Met Val Gln Thr Ser Ser Gln Tyr Lys Phe
210                 215                 220

Val Cys Glu Ala Ile Leu Arg
225                 230
```

(2) INFORMATION FOR SEQ ID NO:38:

(i) SEQUENCE CHARACTERISTICS:
        (A) LENGTH: 232 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:38:

```
Asn Ile Ser Lys Asn Arg Tyr Arg Asp Ile Ser Pro Tyr Asp Ala Thr
1               5                   10                  15

Arg Val Ile Leu Lys Gly Asn Glu Asp Tyr Ile Asn Ala Asn Tyr Ile
            20                  25                  30
```

Asn Met Glu Ile Pro Ser Ser Ile Ile Asn Gln Tyr Ile Ala Cys
          35                  40                  45

Gln Gly Pro Leu Pro His Thr Cys Thr Asp Phe Trp Gln Met Thr Trp
 50                  55                  60

Glu Gln Gly Ser Ser Met Val Val Met Leu Thr Thr Gln Val Glu Arg
65                  70                  75                  80

Gly Arg Val Lys Cys His Gln Tyr Trp Pro Glu Pro Thr Gly Ser Ser
                85                  90                  95

Ser Tyr Gly Cys Tyr Gln Val Thr Cys His Ser Glu Glu Gly Asn Thr
                100                 105                 110

Ala Tyr Ile Phe Arg Lys Met Thr Leu Phe Asn Gln Glu Lys Asn Glu
            115                 120                 125

Ser Arg Pro Leu Thr Gln Ile Gln Tyr Ile Ala Trp Pro Asp His Gly
130                 135                 140

Val Pro Asp Asp Ser Ser Asp Phe Leu Asp Phe Val Cys His Val Arg
145                 150                 155                 160

Asn Lys Arg Ala Gly Lys Glu Glu Pro Val Val Val His Cys Ser Ala
                165                 170                 175

Gly Ile Gly Arg Thr Gly Val Leu Ile Thr Met Glu Thr Ala Met Cys
                180                 185                 190

Leu Ile Glu Cys Asn Gln Pro Val Tyr Pro Leu Asp Ile Val Arg Thr
            195                 200                 205

Met Arg Asp Gln Arg Ala Met Met Ile Gln Thr Pro Ser Gln Tyr Arg
210                 215                 220

Phe Val Cys Glu Ala Ile Leu Lys
225                 230

(2) INFORMATION FOR SEQ ID NO:39:

(i) SEQUENCE CHARACTERISTICS:
        (A) LENGTH: 342 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:39:

Met Thr Ser Arg Leu Arg Ala Leu Gly Gly Arg Ile Asn Asn Ile Arg
1               5                   10                  15

Thr Ser Glu Leu Pro Lys Glu Lys Thr Arg Ser Glu Val Ile Cys Ser
            20                  25                  30

Ile His Phe Leu Asp Gly Val Val Gln Thr Phe Lys Val Thr Lys Gln
        35                  40                  45

Asp Thr Gly Gln Val Leu Leu Asp Met Val His Asn His Leu Gly Val
    50                  55                  60

Thr Glu Lys Glu Tyr Phe Gly Leu Gln His Asp Asp Ser Val Asp
65                  70                  75                  80

Ser Pro Arg Trp Leu Glu Ala Ser Leu Pro Ile Arg Lys Gln Leu Lys
                85                  90                  95

Gly Gly Phe Pro Cys Thr Leu His Phe Arg Val Arg Phe Phe Ile Pro
                100                 105                 110

Asp Pro Asn Thr Leu Gln Gln Glu Gln Thr Arg His Leu Tyr Phe Leu
            115                 120                 125

Gln Leu Lys Met Asp Ile Cys Glu Gly Arg Leu Thr Cys Pro Leu Asn
130                 135                 140

```
Ser Ala Val Val Leu Ala Ser Tyr Ala Val Gln Ser His Phe Gly Asp
145                 150                 155                 160

Tyr Asn Ser Ser Ile His His Pro Gly Tyr Leu Ser Asp Ser His Phe
                165                 170                 175

Ile Pro Asp Gln Asn Glu Asp Phe Leu Thr Lys Val Glu Ser Leu His
            180                 185                 190

Glu Gln His Ser Gly Leu Lys Gln Ser Glu Ala Glu Ser Cys Tyr Ile
        195                 200                 205

Asn Ile Ala Arg Thr Leu Asp Phe Tyr Gly Val Glu Leu His Ser Gly
    210                 215                 220

Arg Asp Leu His Asn Leu Asp Leu Met Ile Gly Ile Ala Ser Ala Gly
225                 230                 235                 240

Val Ala Val Tyr Arg Lys Tyr Ile Cys Thr Ser Phe Tyr Pro Trp Val
                245                 250                 255

Asn Ile Leu Lys Ile Ser Phe Lys Arg Lys Phe Phe Ile His Gln
                260                 265                 270

Arg Gln Lys Gln Ala Glu Ser Arg Glu His Ile Val Ala Phe Asn Met
            275                 280                 285

Leu Asn Tyr Arg Ser Cys Lys Asn Leu Trp Lys Ser Cys Val Glu His
        290                 295                 300

His Thr Phe Phe Gln Ala Lys Lys Leu Leu Pro Gln Glu Lys Asn Val
305                 310                 315                 320

Leu Ser Gln Tyr Trp Thr Met Gly Ser Arg Asn Thr Lys Lys Ser Val
                325                 330                 335

Asn Asn Gln Tyr Cys Lys
                340
```

(2) INFORMATION FOR SEQ ID NO:40:

(i) SEQUENCE CHARACTERISTICS:
        (A) LENGTH: 345 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:40:

```
Met Thr Ser Arg Phe Arg Leu Pro Ala Gly Arg Thr Tyr Asn Val Arg
1               5                   10                  15

Ala Ser Glu Leu Ala Arg Asp Arg Gln His Thr Glu Val Val Cys Asn
            20                  25                  30

Ile Leu Leu Leu Asp Asn Thr Val Gln Ala Phe Lys Val Asn Lys His
        35                  40                  45

Asp Gln Gly Gln Val Leu Leu Asp Val Val Phe Lys His Leu Asp Leu
    50                  55                  60

Thr Glu Gln Asp Tyr Phe Gly Leu Gln Leu Ala Asp Asp Ser Thr Asp
65                  70                  75                  80

Asn Pro Arg Trp Leu Asp Pro Asn Lys Pro Ile Arg Lys Gln Leu Lys
                85                  90                  95

Arg Gly Ser Pro Tyr Ser Leu Asn Phe Arg Val Lys Phe Phe Val Ser
            100                 105                 110

Asp Pro Asn Lys Leu Gln Glu Glu Tyr Thr Arg Tyr Gln Tyr Phe Leu
        115                 120                 125

Gln Ile Lys Gln Asp Ile Leu Thr Gly Arg Leu Pro Cys Pro Ser Asn
    130                 135                 140

Thr Ala Ala Leu Leu Ala Phe Ala Val Gln Ser Glu Leu Gly Asp Tyr
```

```
                   145                 150                 155                 160
Asp Gln Ser Glu Asn Leu Ser Gly Tyr Leu Ser Asp Tyr Ser Phe Ile
                165                 170                 175

Pro Asn Gln Pro Gln Asp Phe Glu Lys Glu Ile Ala Lys Leu His Gln
            180                 185                 190

Gln His Ile Gly Leu Ser Pro Ala Glu Ala Glu Phe Asn Tyr Leu Asn
            195                 200                 205

Thr Ala Arg Thr Leu Glu Leu Tyr Gly Val Glu Phe His Tyr Ala Arg
        210                 215                 220

Asp Gln Ser Asn Asn Glu Ile Met Ile Gly Val Met Ser Gly Gly Ile
225                 230                 235                 240

Leu Ile Tyr Lys Asn Arg Val Arg Met Asn Thr Phe Pro Trp Leu Lys
                245                 250                 255

Ile Val Lys Ile Ser Phe Lys Cys Lys Gln Phe Phe Ile Gln Leu Arg
            260                 265                 270

Lys Glu Leu His Glu Ser Arg Glu Thr Leu Leu Gly Phe Asn Met Val
            275                 280                 285

Asn Tyr Arg Ala Cys Lys Asn Leu Trp Lys Ala Cys Val Glu His His
        290                 295                 300

Thr Phe Phe Arg Leu Asp Arg Pro Leu Pro Pro Gln Lys Asn Phe Phe
305                 310                 315                 320

Ala His Tyr Phe Thr Leu Gly Ser Lys Phe Arg Tyr Cys Gly Arg Thr
                325                 330                 335

Glu Val Gln Ser Val Gln Tyr Gly Lys
            340                 345

(2) INFORMATION FOR SEQ ID NO:41:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:41:

Ile Ala Met Val Thr Ala Glu
1               5

(2) INFORMATION FOR SEQ ID NO:42:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:42:

Gln Glu Val Ser Glu Pro Leu Thr Ala Ala Arg His Ala Gln
1               5                   10

(2) INFORMATION FOR SEQ ID NO:43:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide
```

(xi) SEQUENCE DESCRIPTION: SEQ ID NO:43:

Leu Glu Asp Tyr Phe Thr Ser Thr Glu Pro Gln Tyr Gln Pro Gly Glu
 1               5                  10                  15
Asn Leu (2) INFORMATION FOR SEQ ID NO:44:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:44:

Pro Pro Pro Pro Tyr Pro Pro Pro Arg Pro
 1               5                  10

(2) INFORMATION FOR SEQ ID NO:45:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:45:

Glu Glu Glu Glu Asp Glu Asp Phe Glu Glu Glu
 1               5                  10

(2) INFORMATION FOR SEQ ID NO:46:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:46:

Pro Gln Pro Tyr Val Met Pro Pro Pro Pro
 1               5                  10

(2) INFORMATION FOR SEQ ID NO:47:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:47:

Val His Cys Ser Ala Gly Val Gly Arg Thr Gly
 1               5                  10

(2) INFORMATION FOR SEQ ID NO:48:

(i) SEQUENCE CHARACTERISTICS:
        (A) LENGTH: 7 amino acids
        (B) TYPE: amino acid
        (C) STRANDEDNESS: single
        (D) TOPOLOGY: unknown -continued

```
    (ii) MOLECULE TYPE: peptide (xi) SEQUENCE DESCRIPTION: SEQ ID NO:48:

Lys Cys Xaa Xaa Tyr Trp Pro
1               5
```

NUCLEIC ACID ENCODING NOVEL PROTEIN PHOSPHOTYROSINE PHOSPHATASE PTP-D1

This patent application is a continuation-in-part of U.S. patent application Ser. No. 07/923,740 filed Aug. 5, 1992, abandoned, incorporated by reference herein in its entirety.

TABLE OF CONTENTS

1. Introduction
2. Background of the Invention
   2.1 PTKases
   2.2 PTPases
   2.3 Definitions
3. Summary of the invention
4. Brief description of the drawings
5. Detailed description of the invention
6. EXAMPLE 1: Identification of a New PTPase Subfamily Using the Polymerase Chain Reaction (PCR)
7. EXAMPLE 2: cDNA Cloning of a Member of the PTP-D Subfamily
8. EXAMPLE 3: Northern Blot Analysis of PTP-D1 and PTP-D2
9. EXAMPLE 4: Identification of New Members of the PTP-D
10. EXAMPLE 5: Detection of the Presence of a Nucleic Acid for a PTP-D Protein
11. EXAMPLE 6: Detection of the Presence of and Measurement of the Quantity of a PTP-D Protein or Glycoprotein in a Cell
    11.1 Change of the prokaryotic expression vector PGEX
    11.2 Expression of GST-PTP D1 fusion protein in *E. coli*
    11.3 Production of antibodies with specificity for PTP-D1
    11.4 Detection of the Presence and Measurement of the Quantity of PTP-D1 in a Cell Line
12. EXAMPLE 7: Identification of a Molecule That Stimulates or Inhibits Enzymatic
    12.1 Activity of a PTP-D Protein or Glycoprotein
    12.2 Labeling of Raytide and myelin basic protein with 32p
    12.3 The PTPase activity assay using Raytide or MBP
13. EXAMPLE 8: cDNA Cloning of PTP-D1
    13.1 Methods
    13.2 Results
    13.3 Discussion

BACKGROUND OF THE INVENTION

1. Introduction

The invention pertains to the field of biochemistry and cell and molecular biology. The invention relates to PTP-D proteins or glycoproteins that are members of a novel subfamily (PTP-D) of protein tyrosine phosphatases (PTPases), nucleic acid constructs coding for PTP-D proteins or glycoproteins, recombinant expression vectors carrying the nucleic acid constructs, cells containing the recombinant expression vectors, methods for production and identification of PTP-D proteins and glycoproteins and DNA constructs coding therefor, antibodies specific for PTP-D proteins and glycoproteins, and methods for screening compounds capable of binding to and inhibiting or stimulating protein tyrosine phosphatase enzymatic activity of PTP-D proteins or glycoproteins.

2. Background of the Invention

Phosphorylation of proteins is a fundamental mechanism for regulating diverse cellular processes. While the majority of protein phosphorylation occurs at serine and threonine residues, phosphorylation at tyrosine residues is attracting a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Hunter et al., *Ann. Rev. Biochem.* 54:987–930 (1985), Ullrich et al., *Cell* 61:203–212 (1990), Nurse, *Nature* 344:503–508 (1990), Cantley et al, *Cell* 64:281–302 (1991)).

Biochemical studies have shown that phosphorylation on tyrosine residues of a variety of cellular proteins is a dynamic process involving competing phosphorylation and dephosphorylation reactions. The regulation of protein tyrosine phosphorylation is mediated by the reciprocal actions of protein tyrosine kinases (PTKases) and protein tyrosine phosphatases (PTPases). The tyrosine phosphorylation reactions are catalyzed by PTKases. Tyrosine phosphorylated proteins can be specifically dephosphorylated through the action of PTPases. The level of protein tyrosine phosphorylation of intracellular substances is determined by the balance of PTKase and PTPase activities. (Hunter, T., *Cell* 58:1013–1016 (1989)).

2.1 PTKases

The protein tyrosine kinases (PTKases) are a large family of proteins that includes many growth factor receptors and potential oncogenes. (Hanks et al., *Science* 241:42–52 (1988)). Many PTKases have been linked to initial signals required for induction of the cell cycle (Weaver et al., *Mol. Cell. Biol.* 11, 9:4415–4422 (1991)). PTKases comprise a discrete family of enzymes having common ancestry with, but major differences from, serine/threonine-specific protein kinases (Hanks et al., supra). The mechanisms leading to changes in activity of PTKases are best understood in the case of receptor-type PTKases having a transmembrane topology (Ullrich et al. (1990) supra). The binding of specific ligands to the extracellular domain of members of receptor-type PTKases is thought to induce their oligomerization leading to an increase in tyrosine kinase activity and activation of the signal transduction pathways (Ullrich et al., (1990) supra). Deregulation of kinase activity through mutation or overexpression is a well established mechanism for cell transformation (Hunter et al., (1985) supra; Ullrich et al., (1990) supra).

2.2 PTPases

The protein phosphatases are composed of at least two separate and distinct families (Hunter, T. (1989) supra) the protein serine/threonine phosphatases and the protein tyrosine phosphatases (PTPases).

The protein tyrosine phosphatases (PTPases) are a family of proteins that have been classified into two subgroups. The first subgroup is made up of the low molecular weight, intracellular enzymes that contain a single conserved catalytic phosphatase domain. All known intracellular type PTPases contain a single conserved catalytic phosphatase domain. Examples of the first group of PTPases include (1) placental PTPase 1B (Charbonneau et al., *Proc. Natl. Acad. Sci. USA* 86:5252–5256 (1989); Chernoff et al., *Proc. Natl. Acad. Sci. USA* 87:2735–2789 (1989)), (2) T-cell PTPase (Cool et al., *Proc. Natl. Acad. Sci. USA* 86:5257–5261 (1989)), (3) rat brain PTPase (Guan et al., *Proc. Natl. Acad. Sci. USA* 87:1501–1502 (1990)), (4) neuronal phosphatase (STEP) (Lombroso et al., *Proc. Natl. Acad. Sci. USA* 88:7242–7246 (1991)), and (5) cytoplasmic phosphatases that contain a region of homology to cytoskeletal proteins (Gu et al., *Proc. Natl. Acad. Sci. USA* 88:5867–57871 (1991); Yang et al., *Proc. Natl. Acad. Sci. USA* 88:5949–5953 (1991)).

The second subgroup is made up of the high molecular weight, receptor-linked PTPases, termed R-PTPases. R-PTPases consist of a) an intracellular catalytic region, b) a single transmembrane segment, and c) a putative ligand-binding extracellular domain (Gebbink et al., supra).

The structures and sizes of the c) putative ligand-binding extracellular "receptor" domains of R-PTPases are quite divergent. In contrast, the a) intracellular catalytic regions of R-PTPases are highly homologous. All RPTPases have two tandemly duplicated catalytic phosphatase homology domains, with the prominent exception of an R-PTPase termed HPTPβ, which has "only one catalytic phosphatase domain. (Tsai et al., *J. Biol. Chem.* 266(16):10534–10543 (1991)).

One example of R-PTPases are the leukocyte common antigens (LCA) (Ralph, S. J., *EMBO J.* 6:1251–1257 (1987)). LCA is a family of high molecular weight glycoproteins expressed on the surface of all leukocytes and their hemopoietic progenitors (Thomas, *Ann. Rev. Immunol.* 7:339–369 (1989)). A remarkable degree of similarity is detected with the sequence of LCA from several species (Charbonneau et al., *Proc. Natl. Acad. Sci. USA* 85:7182–7186 (1988)). LCA is referred to in the literature by different names, including T200 (Trowbridge et al., *Eur. J. Immunol.* 6:557–562 (1962)), B220 for the B cell form (Coffman et al., *Nature* 289:681–683 (1981)), the mouse allotypic marker Ly-5 (Komuro et al., *Immunogenetics* 1:452–456 (1975)), and more recently CD45 (Cobbold et al., *Leucocyte Typing III*, ed. A. J. McMichael et al., pp. 788–803 (1987)).

Several studies suggest that CD45 plays a critical role in T cell activation. These studies are reviewed in Weiss A., *Ann. Rev. Genet.* 25:487–510 (1991). In one study, T-cell clones that were mutagenized by NSG and selected for their failure to express CD45 had impaired responses to T-cell receptor stimuli (Weaver et al., (1991) supra). These T-cell clones were functionally defective in their responses to signals transmitted through the T cell antigen receptor, including cytolysis of appropriate targets, proliferation, and lymphokine production (Weaver et al., (1991) supra).

Other studies indicate that the PTPase activity of CD45 plays a role in the activation of pp56$^{lck}$, a lymphocyte-specific PTKase (Mustelin et al., *Proc. Natl. Acad. Sci. USA* 86:6302–6306 (1989); Ostergaard et al., *Proc. Natl. Acad. Sci. USA* 86:8959–8963 (1989)). These authors hypothesized that the phosphatase activity of CD45 activates pp56$^{lck}$ by dephosphorylation of a C-terminal tyrosine residue, which may, in turn, be related to T-cell activation.

Another example of R-PTPases is the leukocyte common antigen related molecule (LAR) (Streuli et al., *J. Exp. Med.* 168:1523–1530 (1988)). LAR was initially identified as a homologue of LCA (Streuli et al., supra). Although the a) intracellular catalytic region of the LAR molecule contains two catalytic phosphatase homology domains (domain I and domain II), mutational analyses suggest that only domain I has catalytic phosphatase activity, whereas domain II is enzymatically inactive (Streuli et al., *EMBO J.* 9(8): 2399–2407 (1990)). Chemically induced LAR mutants having tyrosine at amino acid position 1379 changed to a phenylalanine are temperature-sensitive (Tsai et al., *J. Biol. Chem.* 266(16):10534–10543 (1991)).

A new mouse R-PTP, designated mRPTPμ, has been cloned which has a) an extracellular domain that shares some structural motifs with LAR. (Gebbink et al., (1991) supra). In addition, these authors have cloned the human homologue of RPTPμ and localized the gene on human chromosome 18.

Two Drosophila PTPases, termed DLAR and DPTP, have been predicted based on the sequences of cDNA clones (Streuli et al., *Proc. Natl. Acad. Sci. USA* 86:8698–8702 (1989)). cDNAs coding for another Drosophila R-PTPase, termed DPTP 99A, have been cloned and characterized (Hariharan et al., *Proc. Natl. Acad. Sci. USA* 88:11266–11270 (1991)).

Other examples of R-PTPases include R-PTPase-α, β, γ, and ζ (Krueger et al., *EMBO J.* 9:3241–3252 (1990), Sap et al., *Proc. Natl. Acad. Sci. USA* 87:6112–6116 (1990), Kaplan et al., *Proc. Natl. Acad. Sci. USA* 87:7000–7004 (1990), Jirik et al., *FEBS Lett.* 273:239–242 (1990); Mathews et al., *Proc. Natl. Acad. Sci. USA* 87:4444–4448 (1990), Ohagi et al., *Nucl. Acids Res.* 18:7159 (1990)). Published application WO92/01050 discloses human R-PTPase-α, β and γ, and reports on the nature of the structural homologies found among the conserved domains of these three R-PTPases and other members of this protein family. The murine R-PTPase-α has 794 amino acids, whereas the human R-PTPase-α has 802 amino acids. R-PTPase-α has an intracellular domain homologous to the catalytic domains of other tyrosine phosphatases. The 142 amino acid extracellular domain (including signal peptide of RPTPase-α) has a high serine and threonine content (32%) and 8 potential N-glycosylation sites. cDNA clones have been produced that code for the R-PTPase-α, and R-PTPase-α has been expressed from eukaryotic hosts. Northern analysis has been used to identify the natural expression of R-PTPase-α in various cells and tissues. A polyclonal antibody to R-PTPase-α has been produced by immunization with a synthetic peptide of R-PTPase-α, which identifies a 130 kDa protein in cells transfected with a cDNA clone encoding a portion of R-PTPase-α.

Another example of R-PTPases is HePTP. (Jirik et al, FASEB J. 4:82082 (1990) Abstract 2253). Jirik et al. screened a cDNA library derived from a hepatoblastoma cell line, HepG2, with a probe encoding the two PTPase domains of LCA, and discovered a cDNA clone encoding a new RPTPase, named HePTP. The HePTP gene appeared to be expressed in a variety of human and murine cell lines and tissues.

Since the initial purification, sequencing, and cloning of a PTPase, additional potential PTPases have been identified at a rapid pace. The number of different PTPases that have been identified is increasing steadily, leading to speculations that this family may be as large as the PTKase family (Hunter (1989) supra).

Conserved amino acid sequences in the catalytic domains of known PTPases have been identified and defined (Krueger et al., *EMBO J.* 9:3241–3252 (1990) and Yi et al., *Mol. Cell. Biol.* 12:836–846 (1992), which are incorporated herein by reference.) These amino acid sequences are designated "consensus sequences" herein.

Yi et al. aligned the catalytic phosphatase domain sequences of the following PTPases: LCA, PTP1B, TCPTP, LAR, DLAR, and HPTPα, HPTPβ, and HPTPγ. This alignment includes the following "consensus sequences" (Yi et al., supra, FIG. 2(A), lines 1 and 2):

| | |
|---|---|
| 1. D Y I N A S/N | [SEQ. ID NO: 1] |
| 2. C X X Y W P | [SEQ. ID NO. 2] |
| 3. I/V V M X X X X E | [SEQ. ID NO. 3] |

Krueger et al., aligned the catalytic phosphatase domain sequences of PTP1B, TCPTP, LAR, LCA, HPTPα, β, γ, Γ, δ, ε and ζ and DLAR and DPTP.

This alignment includes the following "consensus sequences: (Krueger et al., supra, FIG. 7, lines 1 and 2):

| | |
|---|---|
| 1. D/N Y I N A S/N | [SEQ. ID NO. 4] |
| 2. C X X Y W P | [SEQ. ID NO. 2] |
| 3. I/V V M X X X X E | [SEQ. ID NO. 3] |

It is becoming clear that dephosphorylation of tyrosine residues can by itself function as an important regulatory mechanism. Dephosphorylation of a C-terminal tyrosine residue has been shown to activate tyrosine kinase activity in the case of the src family of tyrosine kinases (Hunter, *T. Cell* 49:1–4 (1987)). Tyrosine dephosphorylation has been suggested to be an obligatory step in the mitotic activation of the maturation-promoting factor (MPF) kinase (Morla et al., *Cell* 58:193–203 (1989)). These observations point out the need in the art for understanding the mechanisms that regulate tyrosine phosphatase activity.

It is clear that further analysis of structure-function relationships among PTPases are needed to gain important understanding of the mechanisms of signal transduction, cell cycle progression and cell growth, and neoplastic transformation.

2.3 Definitions

Table 1 gives the single-letter abbreviations for amino acids that are in common use among protein chemists and are used herein.

| Amino Acid Name | Symbol |
|---|---|
| Glycine | G |
| Alanine | A |
| Valine | V |
| Leucine | L |
| Isoleucine | I |
| Serine | S |
| Threonine | T |
| Cysteine | C |
| Methionine | M |
| Aspartic Acid | D |
| Asparagine | N |
| Glutamic Acid | E |
| Glutamine | Q |
| Arginine | R |
| Lysine | K |
| Histidine | H |
| Phenylalanine | F |
| Tyrosine | Y |
| Tryptophan | W |
| Proline | P |
| Serine or Asparagine | S/N |
| Aspartic Acid or Asparagine | D/N |
| Isoleucine or Valine | I/V |
| (Amino Acid Not Specified) | X |

3. SUMMARY OF THE INVENTION

The inventors describe herein the identification of a novel subfamily (PTP-D) of protein tyrosine phosphatases, and in particular, PTP-D1 which is a novel member of the subfamily. The novel subfamily, hereinafter "PTP-D subfamily," differs significantly in structure from previously reported PTPases. The present invention thus provides a PTP-D protein or glycoprotein which is a PTPase from the PTP-D subfamily.

Preferably, a PTP-D protein or glycoprotein comprises a PTPase from the PTP-D subfamily of PTPases having catalytic phosphatase domains in which amino acid sequences are selected from:

| | |
|---|---|
| 1. G Y I N A S/N | [SEQ. ID NO. 5] |
| 2. S X X Y W P | [SEQ. ID NO. 6] |
| 3. I A M V X X X X E | [SEQ. ID NO. 7] |

The amino acid sequences selected from:

| | |
|---|---|
| 1. G Y I N A S/N | [SEQ. ID NO. 5] |
| 2. S X X Y W P | [SEQ. ID NO. 6] |
| 3. I A M V X X X X E | [SEQ. ID NO. 7] | have the following amino acid differences in comparison with the previously defined amino acid consensus sequences in the catalytic phosphatase domains of PTPases (differences are underlined):

| | |
|---|---|
| 1. PTP-D: <u>G</u> Y I N A S/N | [SEQ. ID NO. 5] |
| Consensus D Y I N A S/N | [SEQ. ID NO. 1] |
| N Y I N A S/N | [SEQ. ID NO. 8] |
| 2. PTP-D1/D2 <u>S</u> X X Y W P | [SEQ. ID NO. 6] |
| Consensus C X X Y W P | [SEQ. ID NO. 2] |
| 3. PTP-D1/D2 <u>I A M</u> V X X X X E | [SEQ. ID NO. 7] |
| Consensus (I/V/L) V (M/I/L) (V/L/I/M) X X X X E | [SEQ. ID NO. 9] |

When a PTP-D protein or glycoprotein of the invention is one which occurs in nature, it is substantially free of other proteins or glycoproteins with which it is natively associated. A substantially pure PTP-D protein or glycoprotein of the invention may be produced by biochemical purification of the glycoprotein. Alternatively, a PTP-D protein or glycoprotein of the invention may be prepared by chemical means or by recombinant means in the prokaryotic or eukaryotic hosts, and is provided substantially free of other proteins with which it is natively associated and/or has modified amino acids.

The invention is further directed to a fragment of a PTP-D protein or glycoprotein, to a PTP-D protein or glycoprotein having additional amino acids, and to a PTP-D protein or glycoprotein having substituted amino acids, and to a PTP-D protein or glycoprotein having any combination of deleted, additional, or substituted amino acids, such that the PTP-D protein or glycoprotein possesses the desired biological activity.

The invention is further directed to a nucleic acid construct comprising a nucleotide sequence encoding a PTP-D protein or glycoprotein according to the invention in the form of cDNA or genomic DNA. The invention is further directed to a nucleic acid construct in the form of an expression vehicle, as well as prokaryotic and eukaryotic host cells containing the expression vehicle.

Also included in the present invention is a process for preparing a PTP-D protein or glycoprotein of this invention, comprising:

(a) culturing a host capable of expressing a PTP-D protein or glycoprotein under culturing conditions, (b) expressing the PTP-D protein or glycoprotein; and (c) recovering the PTP-D protein or glycoprotein from the culture.

The invention is also directed to an antibody, polyclonal antibody, monoclonal antibody, or chimeric antibody, specific for a PTP-D protein or glycoprotein or for an epitope of a PTP-D protein or glycoprotein.

The invention is further directed to a method for detecting the presence, or measuring the quantity, of a PTP-D protein or glycoprotein in cell or in a subject comprising:

(a) contacting said cell or an extract thereof with an antibody specific for an epitope of a PTP-D protein or glycoprotein; and (b) detecting the binding of the antibody to the cell or extract thereof, or measuring the quantity of antibody bound, thereby detecting the presence or measuring the quantity of the PTP-D protein or glycoprotein.

The invention is also directed to a method for detecting the presence of a nucleic acid construct encoding a normal or mutant PTP-D protein or glycoprotein in a cell or a subject comprising:

(a) contacting a cell or an extract thereof from the subject with a nucleic acid encoding at least a portion of a normal or mutant PTP-D protein or glycoprotein under hybridizing conditions; and (b) measuring the hybridization of the probe to nucleic acid of the cell, thereby detecting the presence of the nucleic acid construct.

The nucleic acid of the cell can be selectively amplified, using the polymerase chain reaction, prior to assay.

The present invention is also directed to a method for identifying and isolating in a chemical or biological preparation a compound capable of binding to a PTP-D protein or glycoprotein, said method comprising:

(a) attaching a PTP-D protein or glycoprotein or the compound-binding portion thereof to a solid phase matrix;

(b) contacting the chemical or biological preparation with the solid phase matrix allowing the compound to bind, and washing away any unbound material;

(c) detecting the presence of the compound bound to the solid phase; and, for purposes of isolation;

(d) eluting the bound compound, thereby isolating the compound.

Finally, the invention includes a method for identifying a molecule capable of stimulating or inhibiting the enzymatic activity of a PTP-D protein or glycoprotein, comprising:

(a) contacting the compound with a PTP-protein or glycoprotein in pure form, in a membrane preparation, or in a whole live or fixed cell;

(b) incubating the mixture in step (a) for a sufficient interval;

(c) measuring the enzymatic activity of the PTP-D protein or glycoprotein;

(d) comparing the enzymatic activity to that of the PTP-D protein or glycoprotein incubated without the compound, thereby determining whether the molecule stimulates or inhibits the activity. A fragment of a PTP-D protein or glycoprotein may be used in this method for identifying a molecule capable of stimulating or inhibiting the activity.

4. BRIEF DESCRIPTION OF THE DRAWINGS

FIG. 1 presents the partial cDNA sequence SEQ ID NO. 23 and the deduced amino acid sequence SEQ ID NO. 24 of PTP-D1, which is a PCR fragment.

FIG. 2 presents the partial cDNA sequence SEQ ID NO. 25 and the deduced amino acid sequence SEQ ID NO. 26 of PTP-D2, which is a PCR fragment.

FIG. 3A shows a comparison of the deduced amino acid sequences of PTP-D1 SEQ ID NO. 28 and PTP-D2 SEQ ID NO. 29 with the amino acid sequence of PTPase 1B SEQ ID NO. 27. The CLUSTAL program is used (Higgins, C., Fuch, R. and Bleasby, D., *Multiple Sequence Alignment, CABIOS* (1991) (in press).

FIG. 3B shows a comparison of the nucleotides between PTP-D1 SEQ ID NO. 30 and PTP-D2 SEQ ID NO. 31.

FIG. 3C shows a comparison of the amino acids between PTP-D1 SEQ ID NO. 32 and PTP-D2 SEQ ID NO. 26.

FIGS. 4A–4B shows the partial cDNA sequence SEQ ID NO. 33 and the deduced amino acid sequence SEQ ID NO. 34 of PTP-D1. This partial cDNA sequence includes the cDNA sequence of the PCR fragment shown in FIG. 1.

FIGS. 5A–5J presents the cDNA sequence SEQ ID NO. 35, the sequence of the complementary strand and the deduced amino acid sequence SEQ ID NO. 36 of the PTP-D1 cDNA clone J 324.

FIG. 6 shows the predicted amino acid sequences SEQ ID NO. 36 of a full-length cDNA clone encoding PTP-D1 SEQ ID NO. 36. The N-terminal ezrin-like domain is boxed. The PTP domain is shaded and boxed. The position of the PCR fragment is in arrow brackets. The putative SH3 binding domain is underlined in bold and the acidic stretch is underlined in hatch. Asterisks indicate PYX-motifs. Putative SH2 binding motifs are doubly underlined.

Figure 7A:
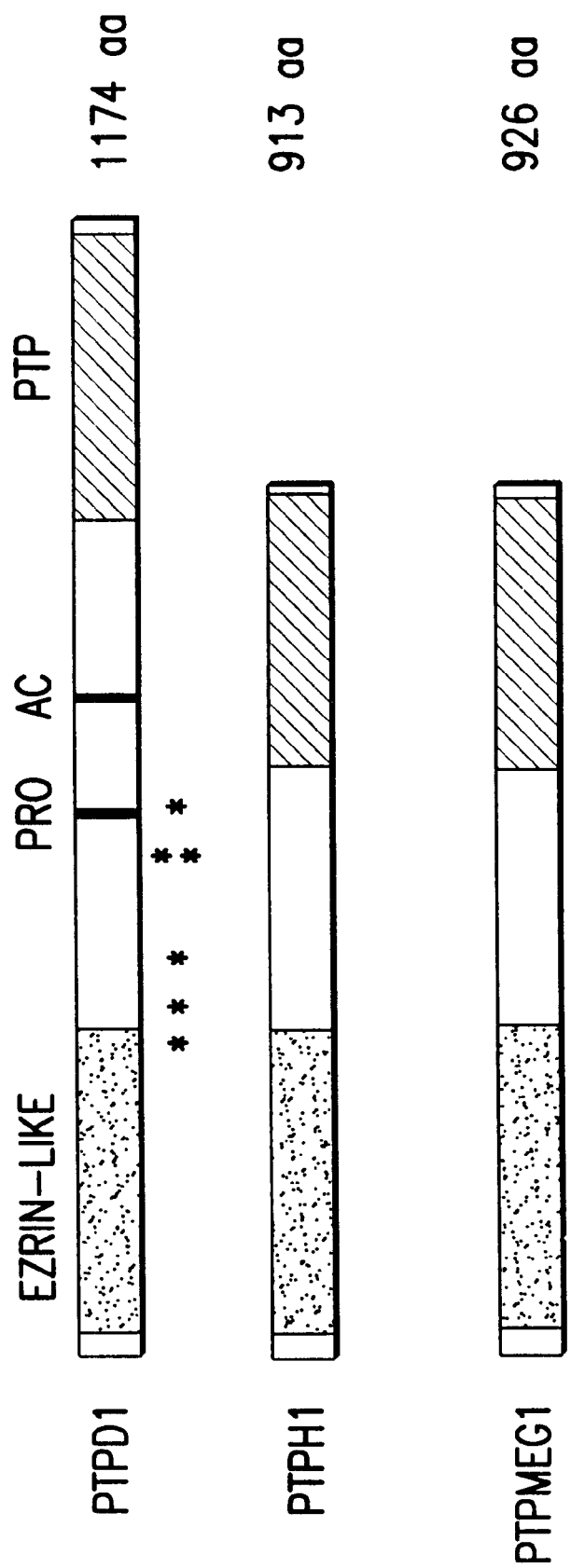

FIGS. 7A–7C show the comparison of PTP-D1, PTPH1 and PTPMEG1. FIG. 7A Schematic representation showing the ezrin-like domains (solid box), the intervening segments (open box), and the PTP domains (hatched box). Asterisks indicate the PYX motif, Pro the putative SH3 binding motif, and Ac the acidic stretch. FIG. 7C Alignment of the ezrin-like domains SEQ ID NOS. 36, 37 and 38, respectively. FIG. 7B Alignment of the PTP domains SEQ ID NOS. 36, 39 and 40, respectively. Both alignments were calculated by the CLUSTAL program. Identical and conserved residues are highlighted in black and gray respectively.

Figure 8A:
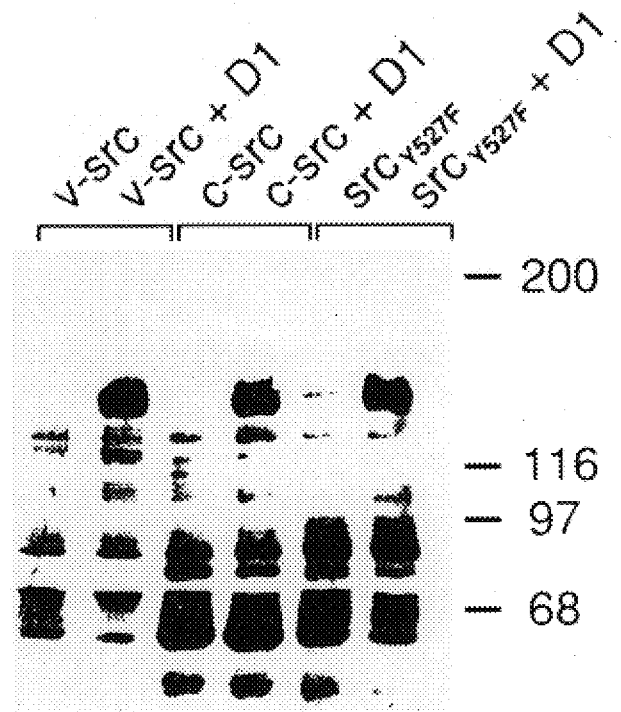
Figure 8B:
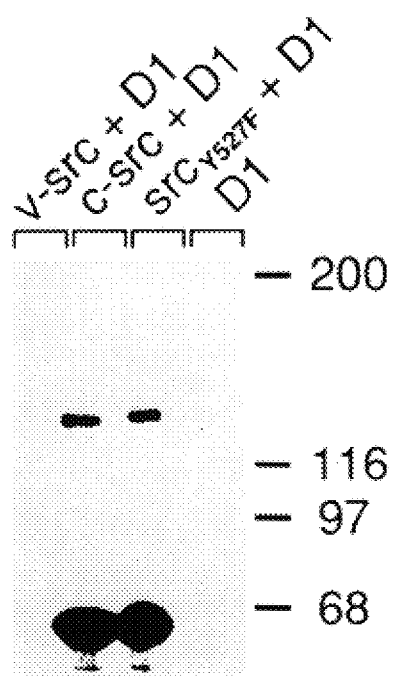

FIGS. 8A–8B shows the transient expression of src kinases and PTP-D1. v-src, c-src, and src$_{Y527F}$ were transiently overexpressed in 293 cells either alone or together with PTP-D1. FIG. 8A. After transfection, cells were incubated in medium containing 0.5% FCS for 24 hours and then lysed. An aliquot of the lysate was analyzed by SDS-PAGE and immunoblotting with an anti-phosphotyrosine antibody. FIG. 8B. Transfected cells were labeled metabolically with $^{35}$S-L-methionine, lysed, the cleared lysates immunoprecipitated with a rabbit antibody directed against the carboxy terminus of c-src and the immunoprecipitates analyzed by SDS-PAGE.

5. DETAILED DESCRIPTION OF THE INVENTION

The inventors have identified a new subfamily ('PTP-D subfamily') of protein tyrosine phosphatases (PTPases) which structurally differs significantly from previously reported PTPases. Members of this PTP-D subfamily are characterized by having, one, two, or three of the following amino acid differences in comparison with the previously defined amino acid consensus sequences in the catalytic phosphatase domains of PTPases (differences are underlined):

| | |
|---|---|
| 1. PTP-D: <u>G</u> Y I N A S/N | [SEQ. ID NO. 5] |
| Consensus D Y I N A S/N | [SEQ. ID NO. 1] |
| N Y I N A S/N | [SEQ. ID NO. 8] |
| 2. PTP-D1/D2 <u>S</u>X X Y W P | [SEQ. ID NO. 6] |
| Consensus C X X Y W P | [SEQ. ID NO. 2] |
| 3. PTP-D1/D2 I <u>A</u>M V X X X X E | [SEQ. ID NO. 7] |
| Consensus (I/V/L) V (M/I/L) (V/L/I/M) X X X X E | [SEQ. ID NO. 9] |

The term "subfamily" is used to indicate a group of PTPases which are structurally related at specific amino acid residues as specified above.

By previously defined amino acid consensus sequences is meant the conserved amino acid sequences in the catalytic phosphatase domains of known PTPases described in Krueger et al., *EMBO J.* 9:3241–3252 (1990) and Yi et al., *Mol. Cell. Biol.* 12:836–846 (1992), which are incorporated herein by reference.

Accordingly, the present invention relates to a PTP-D protein or glycoprotein comprising a PTPase from the PTP-D subfamily of PTPases having a catalytic phosphatase domain having one, two, or three amino acid sequences selected from:

| | |
|---|---|
| 1. G Y I N A S/N | [SEQ. ID NO. 5] |
| 2. S X X Y W P | [SEQ. ID NO. 6] |
| 3. I A M V X X X X E | [SEQ. ID NO. 7] |

At present it is not known whether the PTP-D proteins and glycoproteins of the new PTP-D subfamily of PTPases are receptor-linked PTPases or intracellular PTPases.

In one aspect, the invention is directed to a naturally occurring mammalian PTP-D protein or glycoprotein. In another aspect, the invention is directed to a recombinant mammalian PTP-D protein or glycoprotein. In another aspect, the invention is directed to a chemically synthesized mammalian PTP-D protein or glycoprotein. The preferred PTP-D protein or glycoproteins of the present invention are of human origin.

The invention provides a naturally occurring PTP-D protein or glycoprotein substantially free of other proteins or glycoproteins with which it is natively associated. "Substantially free of other proteins or glycoproteins" indicates that the PTP-D protein or glycoprotein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluids containing the PTP-D protein or glycoprotein to standard protein purification techniques such as immunoadsorbent columns bearing monoclonal antibodies reactive against the protein. Other forms of affinity purification can utilize solid-phase substrates which can bind the catalytic phosphatase domain, or a ligand that will bind to the receptor domain that may be present in a PTP-D protein or glycoprotein. Alternatively, the purification can be achieved by a combination of standard methods, such as ammonium sulfate precipitation, molecular sieve chromatography, and ion exchange chromatography.

It will be understood that a mammalian PTP-D protein or glycoprotein of the present invention can be biochemically purified from a variety of cell or tissue sources. For preparation of a naturally occurring PTP-D protein or glycoprotein, tissues such as skeletal muscle, especially of human origin, are preferred. Cell lines, such as rhabdomyosarcoma cell lines (RD) may be used.

Alternatively, because the gene for a PTP-D protein or glycoprotein can be isolated or synthesized, a PTP-D protein can be synthesized substantially free of other proteins or glycoproteins of mammalian origin in a prokaryotic organism or in a non-mammalian eukaryotic organism, if desired. As intended by the present invention, a recombinant PTP-D protein or glycoprotein produced in mammalian cells, such as transfected COS, NIH3T3, or CHO cells, for example, is either a naturally occurring protein sequence or is a modified protein sequence wherein there are amino acid deletions and/or insertions and/or substitutions. Where a naturally occurring PTP-D protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

In a further aspect, the invention provides a fragment of a PTP-D protein or glycoprotein. The term "fragment" is used to indicate a polypeptide which is derived from a PTP-D protein or glycoprotein having a naturally occurring protein sequence by appropriately modifying the DNA sequence encoding the PTP-D protein or glycoprotein, resulting in deletion of one or more amino acids at one or more sites of the C-terminal, N-terminal, and within the native sequence. Fragments of a PTP-D protein or glycoprotein are useful for screening for compounds that are antagonists or agonists (as defined below). It is understood that such fragments of a PTP-D protein or glycoprotein may retain characterizing portion(s) of the native PTP-D or glycoprotein. In particular, such fragments of PTP-D proteins or glycoproteins should retain one or more biological activities or functions which are characteristic for the intact PTP-D proteins or glycoproteins. Examples, which are not intended to be in any way limiting to the scope of the invention claimed, of PTP-D fragments are: a) the catalytic domain; b) regions of the PTP-D, proteins or glycoproteins which interact with other molecules in the intact cell; c) regulatory parts of PTP-D.

In a further aspect, the invention provides a PTP-D protein or glycoprotein having additional amino acids that is derived from a naturally occurring PTP-D protein or glycoprotein by appropriately modifying the DNA sequence encoding the PTP-D protein or glycoprotein, resulting in addition of one or more amino acids at one or more sites of the C-terminal, N-terminal, and within the native sequence. It is understood that such PTP-D protein or glycoprotein having additional amino acids may retain characterizing portion(s) of the native PTP-D protein or glycoprotein. In particular, such PTP-D proteins or glycoproteins with additional amino acids should retain one or more biological activities or functions which are characteristic for the intact PTP-D proteins or glycoproteins. Examples of such characteristics, of which at least one should be retained: a) the catalytic activity; b) the substrate specificity; c) interaction with other molecules in the intact cell; d) regulatory functions of PTP-D. These examples are not intended to be in any way limiting to the scope of the invention claimed.

In a further aspect, the invention provides a PTP-D protein or glycoprotein having substituted amino acids that is derived from a naturally occurring PTP-D protein or glycoprotein by appropriately modifying or mutating the DNA sequence encoding the PTP-D protein or glycoprotein, resulting in substitution of one or more amino acids at one or more sites of the C-terminal, N-terminal, and within the native amino acid sequence. It is understood that such PTP-D protein or glycoprotein having substituted amino acids may retain characterizing portion(s) of, the PTP-D protein or glycoprotein. In particular, such PTP-D proteins or glycoproteins having substituted amino acids should retain one or more biological activities or functions which are characteristic for the intact PTP-D proteins or glycoproteins. Examples of such characteristics, of which at least one should be retained: a) the catalytic activity; b) the substrate specificity; c) interaction with other molecules in the intact cell; d) regulatory functions of PTP-D. These examples are not intended to be in any way limiting to the scope of the invention claimed.

Any combination of deletion, insertion, and substitution may also be made to arrive at the final construct of a PTP-D protein or glycoprotein, provided that the final construct possesses the desired activity or function present in the intact PTP-D proteins or glycoproteins. Examples of such activities and functions are: a) the catalytic activity; b) substrate specificity; c) interaction with other molecules in vitro and in vivo; d) regulatory functions. Only one of such activities or functions needs to be retained after any combination of deletion, insertion, and substitution. These examples are not intended to be in any way limiting to the scope of the invention claimed. Obviously, the modifications or mutations that will be made in the DNA encoding the PTP-D protein or glycoprotein must not alter the reading frame and preferably will not create complementary regions that could produce secondary mRNA structure (see European Patent Publication No. EP 75,444).

At the genetic level, these PTP-D proteins or glycoproteins having deletions from, and/or insertions to, and/or substitutions of amino acids, ordinarily are prepared by site-directed mutagenesis (as exemplified by Adelman et al., DNA 2:183 (1983)) of nucleotides in the DNA encoding the peptide molecule, thereby producing DNA encoding the PTP-D protein or glycoprotein, and thereafter expressing the DNA in recombinant cell culture (see below). The PTP-D protein or glycoproteins having amino acid deletions and/or insertions and/or additions typically exhibit the same qualitative biological activity as a native PTP-D protein or glycoprotein.

Alternatively, a PTP-D protein or glycoprotein having amino acid deletions and/or insertions and/or substitutions may be conveniently prepared by direct chemical synthesis, using methods well-known in the art.

In a further aspect, the invention provides so-called chimeric molecules which are made up of other PTPases in which one or more specific amino acid sequences are replaced with homologous sequence,(s) from a PTP-D protein or glycoprotein. Chimeric molecules include, for example, a PTP-D protein or glycoprotein having a ligand-binding extracellular domain from another PTPase that is grafted onto a portion of the PTP-D protein or glycoprotein. Other chimeric molecules: a) other PTPases in which the catalytic phosphatase domain has been replaced with the phosphatase domain from a PTP-D protein. In this case, the preferred number of amino acids is between 220 and 260. b) A PTP-D protein or glycoprotein in which part or parts of the catalytic domain has been replaced with homologous part(s) from other PTPases. c) chimeric molecules consisting of one member of the PTP-D subfamily in which a part or parts have been replaced with homologous parts, from one (or more) other member(s) from the PTP-D subfamily.

"Homologous sequences" are defined as sequences in two or more PTPases which are similarly positioned in the primary sequence and which may exhibit sequence homology. It should be emphasized that "homologous sequences" should not be limited to cases with high degree of homology. Chimeric molecules are important tools for elucidating structure-function relationships and for identifying specific compounds (drugs). Therefore, the most useful chimeras are often, but not always, molecules in which a certain portion of one molecule has been replaced with the similarly positioned, but divergent, sequence from another, otherwise homologous, molecule. Thus, the exchanged portions will quite often represent the parts of the molecules where they differ the most.

A PTP-D protein or glycoprotein may contain additional chemical moieties not normally a part of the PTP-D protein or glycoprotein. Covalent modifications are included within the scope of this invention. Such modifications may be introduced into the PTP-D protein or glycoprotein by reacting targeted amino acid residues of the PTP-D protein or glycoprotein with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic dizonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by carbodiimides (R'-N-C-N-R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimideesters, for example, esters with 4-azidosalicyclic acid, homobifunctional imidoesters, including dissuccinimidyl esters such as 3,3'-dithiobis(succinimidylpropionate), and bifunctional maleimides such as bis-N-maleimido-1,8-octane. Derivatizing agents such as methyl-3-[p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of preline and lysine, phosphorylation of hydroxyl groups of seryl or threonyl residues, methylation of the alpha-amino groups of lysine, arginine, and histidine side chains (Creighton, T. E., *Proteins: Structure and Molecule Properties*, W. H. Freeman & Co., San Francisco, pp. 79–86 (1983)), acetylation of the Terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

In a further aspect, the present invention relates to a PTP-D protein or glycoprotein as defined above having domains which show 70% or more identity to the amino acid sequences of PTP-D1 or PTP-D2, as provided in FIGS. 1 and 2, respectively. PTP-D1 and PTP-D2 are PTP-D proteins that are members of the PTP-D subfamily that are expressed in human skeletal muscle.

In another aspect, the present invention relates to a PTP-D protein or glycoprotein comprising PTP-D1 or PTP-D2.

Members of the PTP-D subfamily, PTP-D1 and PTP-D2, have been shown to be expressed in human skeletal muscle. Thus, the present invention relates to but is not in any way limited to such members of the PTP-D1 and PTP-D2 PTP-D subfamily expressed in this tissue.

In another aspect, the present invention relates to a nucleic acid construct which comprises a nucleotide sequence encoding a PTP-D protein or glycoprotein, or encoding a PTP-D protein or glycoprotein having amino acid deletions and/or insertions and/or substitutions. The invention is further directed to the nucleic acid sequence in the form of an expression vector such as a recombinant expression vector, as well as prokaryotic and eukaryotic host cells containing the expression vector.

In additional aspects of the present invention, methods for expressing a nucleic acid construct encoding a PTP-D protein or glycoprotein are provided. PTP-D protein or glycoproteins may be produced by culturing cells in a suitable nutrient medium under conditions which are conducive to the expression of such PTP-D protein or glycoproteins. One of ordinary skill in the art will know how to identify and clone additional PTP-D protein or glycoproteins, of human or other mammalian species, which have sequence homology to the PTP-D protein or glycoproteins described herein, using the nucleic acid construct and oligonucleotides of the present invention without undue experimentation. Furthermore, manipulation of the nucleic acid of the present invention allow the grafting of a particular ligand-binding extracellular domain from a particular PTPase onto portions of a PTP-D protein or glycoprotein resulting in chimeric PTP-D proteins or glycoproteins. Non-limiting examples of such chimeric molecules include the PTP-D protein or glycoprotein having a ligand-binding extracellular domain that is an epidermal growth factor receptor, a fibroblast growth factor receptor, and the like. Genetically engineered chimeric receptors are known in the art (see, for example, Riedel et al., *Nature* 324:628–670 (1986)).

Nucleic acid constructs encoding a PTP-D protein or glycoprotein, and encoding a PTP-D protein or glycoprotein having amino acid deletions and/or insertions and/or substitutions, and encoding chimeric PTP-D proteins or glycoproteins such as those described above, can be used in gene therapy. An abnormal or dysfunctional PTP-D protein or glycoprotein which results in disease, may be replaced by infusion of cells of the desired lineage (such as hemopoietic cells, for example) transfected with a normal PTP-D protein or glycoprotein. Alternatively, or additionally, cells carrying a chimeric PTP-D protein or glycoprotein having a receptor to a ligand of choice (e.g. EGF) can be used for such gene therapy.

The nucleic acid constructs that are recombinant DNA molecules of the present invention can be produced through any of a variety of means, such as, for example, DNA or RNA synthesis, or more preferably, by recombinant DNA techniques. Techniques for synthesizing such molecules are disclosed by, for example, Wu et al. (*Prog. Nucl. Acid. Res. Molec. Biol.* 21:101–141 (1978)). Procedures for constructing recombinant molecules in accordance with the above-described method are disclosed by Sambrook et al., *Molecular Cloning: A Laboratory Manual*, Second Edition, Cold Spring Harbor Press, Cold Spring Harbor, N.Y. (1989).

The 3' terminus of the recombinant DNA molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form, (for example, a sheet, rod, sphere, ovoid, etc. Procedures for such immobilization are well known to those of ordinary skill. In the most preferred embodiment, the 3' end of the recombinant DNA molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant DNA molecules to the support.

Oligonucleotides representing a portion of a PTP-D protein or glycoprotein are useful for screening for the presence of genes encoding such PTP-D proteins and glycoproteins and for the cloning of PTP-D genes. Techniques for synthesizing such oligonucleotides are disclosed by, for example, Wu et al. (supra).

Protein molecules are fragmented as with cyanogen bromide, or with proteases such as papain, chymotrypsin, trypsin, etc. (Oike et al., *J. Biol. Chem.* 257—9751–9758 (1982); Liu et al., *Int. J. Pept. Protein Res.* 21:209–215 (1983)). Because the genetic code is degenerate, more than one codon may be used to encode a particular amino acid (Watson, J. D., In: *Molecular Biology of the Gene,* 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the PTP-D sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the PTP-D fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate a PTP-D gene (Sambrook et al., supra).

A suitable oligonucleotide, or set of oligonucleotides, which is capable of encoding a fragment of a PTP-D gene (or which is complementary to such an oligonucleotide, or set of oligonucleotides) is identified (using the above described procedure), synthesized, and hybridized by means well known in the art, against a DNA or, more preferably, a cDNA preparation derived from cells which are capable of expressing a PTP-D gene. Single stranded oligonucleotide molecules complementary to the "most probable" PTP-D peptide encoding sequences can be synthesized using procedures which are well known to those of ordinary skill in the art (Belagaje et al.,*J. Biol. Chem.* 2545765–5780 (1979); Maniatis et al., *In: Molecular Mechanisms in the Control of Gene Expression,* Nierlich et al. Ed., Acad. Press, N.Y. (1976); Wu et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al., (supra), and by Haymes et al., (*In: Nucleic Acid Hybridization, A Practical Approach,* IRL Press, Washington, D.C. (1985)), which references are herein incorporated by reference. Techniques such as, or similar to, those described above have successfully enabled the cloning of genes for human aldehyde dehydrogenases (Hsu et al., *Proc. Natl. Acad. Sci. USA* 82:3771–3775 (1985)), fibronectin (Suzuki et al.,*EMBO J.* 4:2519–2524 (1985)), the human estrogen receptor gene (Walter et al., *Proc. Natl. Acad. Sci. USA* 82:7889–7893 (1985)), tissue type plasminogen activator (Pennica et al., *Nature* 301:214–221 (1983)) and human term placental alkaline phosphatase complementary DNA (Kam et al., *Proc. Natl. Acad. Sci. USA* 82:(715–8719 (1985)).

In an alternative way of cloning a PTP-D gene, a library of expression vectors is prepared by cloning DNA or, more preferably, cDNA (from a cell capable of expressing PTP-D) into an expression vector. The library is then screened for members capable of expressing a protein which binds to anti-PTP-D antibody, and which has a nucleotide sequence that is capable of encoding polypeptides that have the same amino acid sequence as PTP-D, or fragments thereof. In this embodiment, DNA, or more preferably cDNA, is extracted and purified from a cell which is capable of expressing PTP-D protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or DNA fragment.

An "expression vector" is a vector which (due to the presence of appropriate transcriptional and/or translational control sequences) is capable of expressing a DNA (or cDNA) molecule which, has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing PTP-D in order to produce a prokaryotic genomic expression vector library. Procedures for preparing cDNA and for producing a genomic library are disclosed by Sambrook et al. (supra).

A DNA sequence encoding a PTP-D protein or glycoprotein of the invention, or encoding a PTP-D protein or glycoprotein having amino acid deletions and/or insertions and/or substitutions of the invention, or encoding a chimeric molecule of the invention, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al. (supra), and are well known in the art.

A nucleic acid construct, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a PTPase-encoding sequence) are said to be operably, linked if the nature of the linkage between the two DNA sequences does not (1) result in the introduction of a frame-shift mutation, (2) interfere with the ability of the promoter region sequence to direct the transcription of the PTP-D gene sequence, or (3) interfere with the ability of the PTP-D gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement, of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

Thus, as indicated above, in order to function as a promoter, a promoter sequence must be present as a double-stranded molecule. For the purposes of the present invention, the two strands of a functional promoter sequence are, referred to as a "transcript" strand and a "complementary strand." The "transcript" strand is that strand of the duplex which will be transcribed by the RNA polymerase (i.e. which serves as the template for transcription). The "complementary" strand is, the strand which has a sequence complementary to the "transcript" strand, and which must be present, and hybridized to the "transcript" strand, in order for transcription to occur. Thus, when the "transcript" strand of a promoter sequence is operably linked to a second sequence, hybridization of the "transcript" strand with the "complement" strand, will, in the presence of a polymerase, result in the transcription of the "transcript" strand, and will produce an RNA transcript using the sequence of the "transcript" strand as a template.

The promoter sequences of the present invention may be either prokaryotic, eukaryotic or viral. Suitable promoters are repressible, or, more preferably, constitutive. Examples of suitable prokaryotic promoters include promoters capable or recognizing the T4 (Malik et al., *J. Biol. Chem.* 263:1174–1181 (1984); Rosenberg et al., *Gene* 59:191–200 (1987); Shinedling et al., *J. Molec. Biol.* 195:471–480 (1987); Hu et al., *Gene* 42:21–30 (1986)), T3, SP6, and T7 (Chamberlin et al., *Nature* 228:227–231 (1970); Bailey et al., *Proc. Natl. Acad. Sci. (U.S.A.)* 80:2814–2818 (1983); Davanlook et al., *Proc. Natl. Acad. Sci. (U.S.A.)* 81:2035–2039 (1984)) polymerases; the $P_R$ and $P_L$ promoters of bacteriophage lambda (ne *Bacteriophage Lambda,* Hershey, A. D., Ed., Cold Spring Harbor Press, Cold Spring Harbor, N.Y. (1973); *Lambda H,* Hendrix, R. W., Ed., Cold Spring Harbor Press, Cold Spring Harbor, N.Y. (1980)); the trp, recA, heat shock, and lacZ promoters of *E. coli*; the α-amylase (Ulmanen et al., *J. Batetiol.* 162:176–182 (1985)) and the δ-28 specific promoters of *B. subthis* (Gilman et al., *Gene* 32:11–20 (1984)); the promoters of the bacteriophages of Bacillus (Gryczan, T. J., In: *The Molecular Biology of the Bacilli,* Academic Press, Inc., N.Y. (1982)); Streptomyces promoters (Ward et al., *Mol. Gen. Genet.* 203:468–478 (1986)); the int promoter of bacteriophage lambda; the bla promoter of the β-lactamase gene of pBR322, and the CAT promoter of the chloramphenicol acetyltransferase gene of βR325, etc. Prokaryotic promoters are reviewed by Glick, B. R. *J. Ind. Microbiol.* 1:277–282 (1987)); Cenatiempo, Y. (*Biochimie* 68:505–516 (1986)); Watson et al. (*In: Molecular Biology of the Gene,* Fourth Edition, Benjamin Cummins, Menlo Park, Calif. (1987)); and Gottesman, S. (*Ann. Rev. Genet.* 18:415–442) (1984)). Preferred eukaryotic promoters include the promoter of the mouse metallothionein I gene (Hamer et al., *J. Mol. Appl. Gen.* 1:273–288 (1982)); the SV40 early promoter (Benoist et al., *Nature*

(London) 290:304–310 (1981)); and the yeast gal4 gene promoter (Johnston et al., *Proc. Natl. Acad. Sci. (USA)* 79:6971–6975 (1982); Silver et al., *Proc. Natl. Acad. Sci. (USA)* 81:5951–5955 (1984)). All of the above listed references are incorporated by reference herein.

Strong promoters are preferred. Examples of such preferred promoters are those which recognize the T3, SP6 and T7 polymerases, the PL promoter of the mouse metallothionein I gene. A most preferred promoter for eukaryotic expression of PTP-D is SV40 promoter such as that driving transcription in the pLSV vector (Livneh et al., (1986) *J. Biol. Chem.* 261, 12490–12497). The sequences of such polymerase recognition sites are disclosed by Watson et al. (*In: Molecular Biology of the Gene,* Fourth Edition, Benjamin/Cummings Publishing Co., Inc., Menlo Park, Calif., (1987)).

In a further aspect, the present invention relates to an antibody which is capable of specifically recognizing a PTP-D protein or glycoprotein or of specifically recognizing an epitope of a PTP-D protein or glycoprotein.

The recombinantly expressed or naturally occurring PTP-D protein or glycoprotein, and/or the antibodies recognizing the PTP-D protein or glycoprotein may be used in a method of diagnosing diseases or conditions with abnormal expression or activation of PTP-D protein or glycoproteins. The present invention provides methods for evaluating the presence and the level of normal or mutant PTP-D protein or glycoprotein in a subject. Absence, or more typically, low expression of the PTP-D protein or glycoprotein, or presence of a mutant PTP-D protein or glycoprotein, in an individual may serve as an important predictor of susceptibility to oncogenic transformation and the development of cancer. Alternatively, over-expression of DPTP-D protein or glycoprotein, possibly due to a mutant receptor/enzyme system insensitive to negative regulation, or due to overabundance of a stimulatory ligand in the body, may serve as an important predictor of susceptibility to diabetes.

The invention is also directed to the use of such antibodies to detect the presence of, or measure the quantity or concentration of, a PTP-D protein or glycoprotein in a cell, a cell or tissue extract, or a biological fluid.

In one aspect, the present invention relates to a method for detecting the presence of or measuring the quantity of a PTP-D protein or glycoprotein in a cell, comprising:

(a) contacting said cell or an extract thereof with an antibody specific for an epitope of a PTP-D protein or glycoprotein; and (b) detecting the binding of said antibody to said cell or extract thereof, or measuring the quantity of antibody bound, thereby determining the presence of or measuring the quantity of said PTP-D protein or glycoprotein.

The term "antibody" is meant to include polyclonal antibodies, monoclonal antibodies (mAbs), chimeric antibodies, and anti-idiotypic (anti-ld) antibodies.

Polyclonal antibodies are heterogeneous populations of antibody molecules derived from the sera of animals immunized with an antigen.

Monoclonal antibodies (mabs) are a substantially homogeneous population of antibodies to specific antigens. MAbs may be obtained by methods known to those skilled in the art. See, for example, Kohler et al., *Nature* 256:495–497 (1975) and U.S. Pat. No. 4,376,110. Such antibodies may be of any immunoglobulin class including IgG, IgM, IgE, IgA, IgD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/C mice to produce ascites fluid containing high concentrations of the desired mabs. MAbs of isotype IgM or IgG may be purified from such ascites fluids, or from culture supernatants, using column chromatography methods well known to those of skill in the art.

Chimeric antibodies are molecules in which different portions are derived from different animal species, such as those having variable region derived from a murine MAb and a human immunoglobulin constant region. Chimeric antibodies and methods for their production are known in the art (Cabilly et al., *Proc. Natl. Acad. Sci. USA* 71:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Sahagan et al., *J. Immunol.* 137:1066–1074 (1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 140:1041–1043 (1988)). These documents are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against a PTP-D protein or glycoprotein of the present invention may be used to induce anti-Id antibodies in suitable animals, such as BALB/C mice. Spleen cells from such immunized mice are used to produce anti-Id hybridomas secreting anti-Id mabs. Further, the anti-Id mabs can be coupled to a carrier such as keyhole limpet hemocyanin (KLH) and used to immunize additional BALB/C mice. Sera from these mice will contain anti-anti-Id antibodies that have the binding properties of the original mAb specific for a PTP-D epitope.

The anti-Id mAbs thus have their own idiotypic epitopes, or "idiotopes" structurally similar to the epitope being evaluated, such as a PTP-D protein or glycoprotein.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of a PTP-D protein or glycoprotein according to the methods disclosed herein for intact antibody molecules. Such fragments are typically produced by proteolytic cleavage, using enzymes such as papain (to produce Fab fragments) or pepsin (to produce F(ab')$_2$ fragments).

The antibodies, or fragments of antibodies, useful in the present invention may be used to quantitatively or qualitatively detect the presence of cells which express a PTP-D protein or glycoprotein. This can be accomplished by immunofluorescence techniques employing a fluorescently labeled antibody (see below) coupled with light microscopic, flow cytometric, or fluorimetric detection.

The antibodies (or fragments thereof) useful in the present invention may be employed histologically, as in immunofluorescence or immunoelectron microscopy, for in situ detection of a PTP-D protein or glycoprotein. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of a PTP-D protein or glycoprotein but also its distribution on the examined tissue. Using the present invention, those of ordinary skill will readily perceive that any of a wide variety of histological methods (such as staining procedures) can be modified in order to achieve such in situ detection. Such assays for a PTP-D protein or glycoprotein typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying a PTP-D protein or glycoprotein, and detecting the antibody by any of a number of techniques well-known in the art.

The biological sample may be treated with a solid phase support such as nitrocellulose, or other solid support which is capable of immobilizing cells, cell particles or soluble proteins. The support may then be washed with suitable buffers followed by treatment with the detectably labeled PTP-D specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetitite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-PTP-D antibody may be determined according to well known methods. Those skilled in the art will be able to determine operative and optimal assay conditions for each determination by employing routine experimentation.

Other steps as washing, stirring, shaking, filtering and the like may be added to the assays as is customary or necessary for the particular situation.

One of the ways in which the PTP-D-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect a PTP-D protein or glycoprotein through the use of a radioimmunoassay (RIA) (see, for example, Work et al., *Laboratory Techniques and Biochemistry in Molecular Biology*, North Holland Publishing Company, New York, (1978), which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aeluorin.

The present invention also relates to a method for detecting the presence of a nucleic acid construct encoding a PTP-D protein or glycoprotein, or a nucleic acid construct encoding a mutant PTP-D protein or glycoprotein, in a subject, comprising:

(a) contacting a cell or an extract thereof from said subject with a nucleic acide probe encoding at least a portion of said normal or mutant PTP-D protein or glycoprotein under hybridizing conditions; and (b) measuring the hybridization of said probe to the nucleic acid of said cell, thereby detecting the presence of said nucleic acid construct. The method may comprise an additional step (c) before step (a). Step (c) provides selectively amplifying the amount of nucleic acid of said cell encoding said PTP-D protein or glycoprotein, which may be by the polymerase chain reaction.

Oligonucleotide probes encoding various portions of PTP-D protein or glycoproteins (see above) are used to test cells from a subject for the presence of DNA or RNA sequence encoding a PTP-D protein or glycoprotein. Techniques for synthesizing such probes are disclosed by for example, Wu et al., *Prog. Nucl. Acid. Res. Molec. Biol.* 21:101–141 (1978). A preferred probe would be one directed to the nucleic acid sequence encoding at least four amino acid residues, and preferably at least five amino acid residues, of a PTP-D protein or glycoprotein of the present invention (see Example 4 below). Qualitative or quantitative assays can be performed using such probes. For example, Northern analysis (see Example 3 below) is used to measure expression of a PTP-D MRNA, such as PTP-D1 MRNA and PTP-D2 mRNA, in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224); and Sambrook et al., (supra), which documents are herein incorporated by reference.)

Recently, an in vitro, enzymatic method has been described which is capable of increasing the concentration of such desired nucleic acid molecules. This method has been referred to as the "polymerase chain reaction" or "PCR" (Mullis et al., *Cold Spring Harbor Symp. Quant. Biol.* 51:263–273 (1986); Erlich, EP 50,424; EP 84,796, EP 258,017, EP 237,362; Mullis, K., EP 201,184; Mullis et al., U.S. Pat. No. 4,683,202; Erlich, H., U.S. Pat. No. 4,582,788; and Saiki et al., U.S. Pat. No. 4,683,194).

The present invention also relates to a method for identifying in a chemical or biological preparation a compound capable of binding to a PTP-D protein or glycoprotein, said method comprising:

(a) attaching said PTP-D protein or glycoprotein or a compound-binding portion thereof to a solid phase matrix;

(b) contacting said chemical or biological preparation with said solid phase matrix allowing said compound to bind, and washing away any unbound material; and (c) detecting the presence of said compound bound to said solid phase.

The present invention also relates to a method for isolating from a complex mixture a compound capable of binding to a PTP-D protein or glycoprotein, comprising:

(a) attaching said PTP-D protein or glycoprotein, or a compound-binding portion thereof, to a solid phase matrix;

(b) contacting said complex mixture with said solid phase matrix allowing said compound to bind, and washing away any unbound material;

(c) eluting said bound compound, thereby isolating said compound.

By "compound capable of binding to a PTP-D protein or glycoprotein" is meant a naturally occurring or synthetically produced molecule which interacts with PTP-D outside of the catalytic site of the phosphatase domain. By the "catalytic site" is meant the smallest, contiguous part of PTP-D which contains phosphatase activity. Such compounds may directly or indirectly modulate the enzymatic activity of the PTP-D protein or glycoprotein. Examples of such compounds are (i) intracellular proteins which interact with and may be dephosphorylated by a PTP-D protein or glycoprotein; (ii) naturally occurring molecules produced by other cell types.

By a "compound-binding portion" of a PTP-D protein or glycoprotein is meant a part of the molecule which is outside of the catalytic site. Any part of the PTP-D proteins or glycoproteins which are not part of the catalytic site may be a compound-binding portion. A "compound-binding portion" may be prepared from naturally occurring or recombinantly expressed PTP-D proteins or glycoproteins by proteolytical cleavage followed by conventional purification procedures known to those of skill in the art. Alternatively, the compound-binding portion of a PTP-D protein or glycoprotein may be produced by recombinant technology known to those of skill in the art by expressing only these parts of PTP-D in suitable cells.

In a still further aspect, the present invention relates to a method of screening for antagonists which are defined as molecules which directly or indirectly inhibit the enzymatic activity or activation of a PTP-D protein or glycoprotein. In a further aspect, the present invention relates to a method of screening for agonists which are defined as molecules which directly or indirectly increase the enzymatic activity or activation of a PTP-D protein or glycoprotein.

PTP-D proteins or glycoproteins of the present invention are useful in methods for screening drugs and other agents which are capable of activating or inhibiting the phosphatase activity, and thereby affecting major pathways of cellular metabolism. By attaching an intact PTP-D protein or glycoprotein or a fragment of a PTP-D protein or glycoprotein, to a solid phase matrix, an affinity probe is created which can be used to screen biological products or chemical agents for their capacity to interact with a PTP-D protein or glycoprotein on the basis of their binding activity. Bound material can then be eluted from the affinity probe in purified form.

A PTP-D protein or glycoprotein, or a PTP-D protein or glycoprotein having amino acid deletions and/or insertions and/or substitutions and having enzymatic activity can be used for testing of compounds capable of enhancing or inhibiting the phosphatase activity. The ability of a compound under test to modify phosphatase activity can be tested in an in vitro system wherein the test compound is added to a purified PTP-D protein or glycoprotein, or to a PTP-D protein or glycoprotein having amino acid deletions and/or insertions and/or substitutions and having enzymatic activity, and the effects on enzyme activity measured using standard enzymological procedures well known to those of skill in the art.

A suitable fragment of a PTP-D protein or glycoprotein for use in screening may be prepared by limited proteolytic treatment of the naturally occurring or recombinantly expressed PTP-D protein or glycoprotein. Alternatively, suitable fragment(s) of PTP-D may be produced by recombinant technology. As an example, which is not intended to be in any way limiting to the scope of the invention claimed, it may be preferable to use only the catalytic domains for screening purposes. Such catalytic domains, which consist only of the minimum number of amino acids needed for enzymatic activity, could be produced either alone or as part of a fusion protein in suitable hosts (e.g., E. coli) by recombinant technology well known to those of skill in the art.

Alternatively, the action of a compound on PTPase activity can be measured in a whole cell preparation using live or fixed cells, or a membrane fraction derived from live or fixed cells. This method is useful for screening compounds acting directly on the enzymatic portion of a PTP-D protein or glycoprotein. If a PTP-D molecule or glycoprotein has an extracellular receptor portion, then this method is useful for screening compounds acting via the extracellular receptor portion. A test compound is incubated with cells, or with a membrane preparation derived therefrom, which express high amounts of a PTP-D protein or glycoprotein of this invention, such as transfected COS or NIH-3T3 cells. The amount of cellular phosphotyrosine is then measured, using methods well-known in the art (Nonegger, et al., Cell 51:199–209 (1987); Margolis et al., Cell 57.1101–1107 (1989)). The results are compared to results obtained in the absence of the test compound, or in the absence or presence of a known activator of a PTP-D protein or glycoprotein. In such studies, the action of the test compound in the presence of an activator of tyrosine kinase can also be measured.

A compound which stimulates PTPase activity will result in a net decrease in the amount of phosphotyrosine, whereas a compound which inhibits PTPase activity will result in a net increase in the amount of phosphotyrosine.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPases, leading to dephosphorylation, would serve as a counterregulatory mechanism to prevent or inhibit growth, and might serve as an endogenous regulatory mechanism against cancer. Thus, mutation or dysregulation of this receptor-enzyme system may promote susceptibility to cancer.

The insulin receptor is also a tyrosine kinase, and phosphorylation of tyrosine in cells bearing insulin receptors would be associated with normal physiological function. In contrast to the case of cell growth and cancer, activation of a PTPase would counteract insulin effects. Subnormal PTPase levels or enzymatic activity would act to remove a normal counterregulatory mechanism. Perhaps more important, though, over-activity, or inappropriate activation, of a PTPase would be expected to inhibit or totally prevent the action of insulin on cells, leading to diabetes (of an insulin-resistant variety). Thus, susceptibility to diabetes may be associated with PTPase dysregulation.

Therefore, the methods of the present invention for identifying normal or mutant PTP-D genes, or for measuring the amount or activity of PTP-D protein or glycoprotein associated with a cell or tissue, can serve as methods for identifying susceptibility to cancer, diabetes, or other diseases associated with alterations in cellular phosphotyrosine metabolism.

The invention also relates to the use of such identified antagonists or agonists in pharmaceutical compositions intended for treatment of diseases or conditions with either normal or abnormal expression of a PTP-D protein or glycoprotein. The composition may typically be in a form for systemic or topical injection or infusion and may, as such, be formulated with a suitable carrier for injection or infusion.

The present invention also relates to a method for preventing or treating diseases or conditions involving the activation of a PTP-D protein or glycoprotein, the method comprising administering, to a patient in need thereof, an effective dosage of a PTP-D protein or glycoprotein of the invention or an antibody of the invention or a molecule that stimulates or inhibits enzymatic activity of a PTP-D protein or glycoprotein of the invention.

The present invention is further illustrated in the examples shown below which are not intended to be in any way limiting to the scope of the invention as claimed.

6. EXAMPLE 1

Identification of a New PTPase Subfamily Using the Polymerase Chain Reaction (PCR)

Total RNA was isolated from human skeletal muscle by the guanidinium thiocyanate/CsCl procedure (Chirgwin et al., Biochem. 18:5293–5299 (1979)). Poly(A)+ RNA was isolated on an oligo(dT) cellulose column (Aviv et al., Proc. Natl. Acad. Sci. USA 58:1408–1412 (1972)). First strand cDNA was synthesized from 2 μg poly(A)+ RNA using oligo(dT) priming and Moloney Murine Leukemia Virus RNase H-Reverse Transcriptase (Gibco BRL Gaithersburg, Md. 20877, U.S.A.) in accordance with the manufacturer's recommendations.

cDNA corresponding to PTPases expressed in skeletal muscle were isolated by the polymerase chain reaction (Saiki et al., Science 239:487–491 (1988)). In short, human muscle first strand cDNA from above (corresponding to about 50 ng) was amplified with the following set of degenerative oligonucleotide primers using the Gene Amp kit (Perkin Elmer Cetus, Norwalk, Conn., U.S.A.).

Sense prime (oligonucleotide no. 58)

5'A(CT)TT(CT)TGG(ACG)(AG)(AG)ATG
  (AG)T(TCGA)TGG 3'        [SEQ. ID NO. 10]

Anti-sense primer (oligonucleotide no. 57)

5'CC(TCGA)A(CT)(AGT)CC(ATC)GC(AG)CT(SEQ. ID NO. 11]

The primers correspond to the following amino acid consensus sequences:

Sense primer (oligonucleotide #58)

F W X M X W        [SEQ. ID NO. 12]

Antisense primer (oligonucleotide #57)

H C S A G (S/I/V) G.        [SEQ. ID NO. 13]

Each PCR cycle comprises a denaturation step at 94° C. for 1 minute, an annealing step at 37° C. for 2 minutes, and an extension step at 72° C. for 2 minutes. Thirty to 40 cycles were carried out. The reaction products were subjected to agarose gel electrophoresis. The fragments of the expected size (based on the structure of already described PTPases) were isolated, subcloned using the TA cloning system (Invitrogen, San Diego, Calif.) and sequenced by the enzymatic chain termination method described by Sanger et al., *Proc. Natl. Acad. Sci. USA* 74:5463–5467 (1977)), (Sequenase, U.S. Biochemicals) using standard techniques (as described in *Current Protocols in Molecular Biology*, eds. F. M. Ausubel et al., John Wiley & Sons, New York, 1988). The partial DNA sequence and the deduced amino acid sequence of two PCR fragments, termed PTP-D1 and PTP-D2, are shown in FIG. 1 and FIG. 2, respectively. The deduced amino acid sequences were compared with PTPase 1B in FIG. 3A using the CLUSTAL program (Higgins, C., Fuch, R., and Bleasby, D., *Multiple Sequence Alignment, CABIOS* (1991) (in press)).

It appears that both fragments are clearly homologous to other known PTPases, but, surprisingly, have features not yet described for this class of enzymes (analysis by the University of Wisconsin, Genetics Computer Group program).

These unique features of PTP-D1 and PTP-D2 are shown below in comparison with the consensus sequences of the previously described known PTPases (differences are underlined):

| | |
|---|---|
| 1. PTP-D1/D2 S X X Y W P | [SEQ. ID NO. 6] |
| Consensus C X X Y W P | [SEQ. ID NO. 2] |
| 2. PTP-D1/D2 I A M V X X X X E | [SEQ. ID NO. 7] |
| Consensus (I/V/L) V (M/I/L) (V/L/I/M) X X X X E | [SEQ. ID NO. 9] |

7. EXAMPLE 2 cDNA Cloning of a Member of the PTP-D Subfamily

Messenger RNA was prepared from human skeletal muscle as described in EXAMPLE 1. A cDNA library was constructed using the methods described by Okayama and Berg, *Mol. Cell. Biol.* 2:161–170 (1982); Okayama and Berg, *Mol. Cell. Biol.* 3:280–289 (1983). The pCDVI-PL vector was used for preparation of the primer fragment (Noma et al., *Nature* 319:640–646 (1986). A short synthetic adapter was used as second strand primer as recently described (Boel et al., *BioTechniques* 11:26 (1991)). *E. coli* DH5α (Gibco BRL, Gaithersburg, Md. 20877, U.S.A.) was used for transformation according to the protocols by H. Inuoue et al., *Gene* 96:23–28 (1990). After transformation, the cells were plated onto LB plates (containing 50 µg ampicillin/ml) at a density of 15,000–20,000 colonies per plate.

Nitrocellulose replica filters (Schleicher & Schuell, BA85) were screened with standard colony hybridization technique (Maniatis et al., *Molecular Cloning (A Laboratory Manual)*, Cold Spring Harbor Laboratory, second edition (1988). The following oligonucleotide was synthesized, labeled at the 5' end using T4, polynucleotide kinase and [α-$^{32}$p]ATP (Amersham) and used for screening of the cDNA library:

5' ATA GCA ATG GTG ACA GCA GAA 3'     [SEQ. ID NO. 14]

This oligonucleotide corresponds to the amino acid sequence Ile-Ala-Met-Val-Thr-Ala-Glu (SEQ. ID NO. 41) of the PCR fragment no. 1 from EXAMPLE 1. Ten pmoles of the labeled oligonucleotide in 50 ml of hybridization solution (6×SSC, 5× Denhardt's solution, 0.05% SDS (*Current Protocols in Molecular Biology*, eds. F. M. Ausubel et al., John Wiley & Sons, New York, (1988)) were added to replica nitrocellulose filters and allowed to hybridize at 42° C. for 3 hours. Then the filters were washed in 6×SSC, 0.05 % SDS three times at room temperature, once at 42° C. and finally once at 48° C. Positive colonies identified by autoradiography were isolated by standard techniques (Maniatis et al., *Molecular Cloning (A Laboratory Manual)*, Cold Spring Harbor, Laboratory, second edition (1988). The partial sequence of one positive clone, denoted PTP-D1, and the deduced amino acid sequence is shown in FIGS. 4A–4B. This partial sequence includes the sequence of the PCR fragment no. 1 from above and thus confirms the identity of the isolated cDNA clone. Further, comparison with previously described PTPases indicates at least one additional unique feature of PTP-D1 (the difference is underlined):

| | |
|---|---|
| 3. PTP-D1 G Y I N A S | [SEQ. ID NO. 5] |
| Consensus N/D Y I N A S/N | [SEQ. ID NO. 4] |

8. EXAMPLE 3

Northern Blot Analysis of PTP-D1 and PTP-D2

Total RNA was isolated from human skeletal muscle by the acid guanidium thiocyanate-phenol-chloroform extraction procedure as described by Puissant et al., *BioTechniques* 8:148–149 (1990). Poly(A)+ RNA was isolated on an oligo (dT) column (Aviv et al., *Proc. Natl. Acad. Sci. USA*. 69:1408–1412 (1972)). Fifteen µg poly(A)+ RNA were loaded in the lane probed for PTP-D1 expression, and 7.5 µg were loaded in the lane analyzed for PTP-D2 expression, the RNA was separated in an agarose-formaldehyde gel and blotted to nitrocellulose filters using standard techniques (*Current Protocols in Molecular Biology*, eds. F. M. Ausubel et al., John Wiley & Sons, New York (1988)). The filters were hybridized with $^{32}$P-labeled cDNA fragments corresponding to the sequences shown for PTP-D1 and PTP-D2. The $^{32}$P-labeling was done with the Random Primers DNA Labeling System (Cat. no. 8187SA, Bethesda Research Laboratories, Gaithersburg, Md. 20877, U.S.A.) according to the manufacturer's instructions. Subsequently, the filters were applied to X-ray films. The expression pattern of PTP-D1 and PTP-D2 in various human tissues and cell lines was analyzed by Northern blots. Both PTP mRNAs are relatively abundant in human placenta, lung, kidney, and in normal and diabetic skeletal muscle. The major transcripts of PTP-D1 and PTP-D2 in skeletal muscle were 6.5 kb and 11 kb respectively. PTP-D1 mRNA was additionally found expressed in colon, where only very low expression of PTP-D2 was observed. Spleen, stomach, and liver do not seem to express appreciable amounts of either PTP as judged by northern blots. Expression levels of both PTP-D1 and PTP-D2 were high in the rhabdomyosarcoma cell lines RD and A673. The PTP-D1 mRNA level is considerably higher in the embryonic cell RD than in A673, whereas the opposite is the case of PTP-D2.

9. EXAMPLE 4

Identification of New Members of the PTP-D

Total RNA is isolated from each of the following tissues and cell lines: skeletal muscle, liver, placenta, Hep G2 (American Type Culture Collection (ATCC) HB8065), RD (ATCC CCL 136) (Puissant et al., *BioTechniques* 8:148–149

(1990)). Poly(A)+ RNA is isolated on an oligo (dT) column (Aviv et al., *Proc. Natl. Acad. Sci. USA* 69:1408–1412 (1972)). First strand cDNA synthesis is performed as described in Example 1. The cDNA preparations from the above-mentioned tissues and cell lines are individually subjected to the polymerase chain reaction using standard conditions (*PCR Technology Principles and Applications for DNA Amplification*, Erlich, H. E., ed., Stockton Press, New York, (1989)). The following primers are used for the amplifications:

Sense primer:

(oligonucleotide no. 58, see Example 1 of the present invention) in combination with either of the two anti-sense primers:

Oligonucleotide no. 250 (corresponding to the amino acid sequence CYATTG [SEQ. ID NO. 15] of PTP-D1 and PTP-D2):

5'AG(TCGA)CC(TCGA)GT(TCGA)GT(TCGA)GC
  (AG)TA(AG)CA                          [SEQ.ID NO. 16]

Oligonucleotide no. 251 (corresponding to the amino acid sequence QERTVW [SEQ. ID NO. 17] of PTP-D1):

5' GGT(TCGA)AC(TCGA)GT(TCGA)C
   (TG)(TC)TC(TC)T                      [SEQ.ID NO. 18]

Thirty to 40 PCR cycles are carried out. The reaction products are subjected to agarose gel electrophoresis. The fragments of the expected size (around 190 bp for the combination of oligonucleotides nos. 58 and 250; around 235 bp for the combination of oligonucleotides nos. 58 and 251) are isolated, blunt-ended and subcloned into the pGEM3 vector (Promega) using standard techniques (Ausubel et al., *Current Protocols in Molecular Biology*, John Wiley & Sons, New York, (1988)). The subcloned PCR products are sequenced by the enzymatic chain termination method (Sanger et al., *Proc. Natl. Acad. Sci. USA* 74:5463–5467 (1977)) using Sequenase (United States Biochemical, Cleveland, Ohio 44122, U.S.A.). The nucleotide sequences and the corresponding amino acid sequences are compared to the sequences of PTP-D1 and PTP-D2. Clones which exhibit 70% or more identity to the PTP-D1 and/or the PTP-D2 sequences shown in Examples 1 and 2 are identified as members of the PTP-D subfamily according to the present invention.

10. EXAMPLE 5

Detection of the Presence of a Nucleic Acid for a PTP-D Protein

Total RNA is isolated from the cell lines Hep G2 (American Type Culture Collection (ATCC) HB8065) and Rd (ATCC CCL 136). Puissant et al., Biotechinques 8:148–149 (1990)). Poly(A)+ RNA is isolated on an oligo (dT) column (Aviv & Leder, *Proc. Natl. Acad. Sci USA* 69:1408–1412 (1972)). First strand cDNA synthesis is performed as described in Example 1. The cDNA is subjected to the polymerase chain reaction using standard conditions (*PCR Technology—Principles and Applications for DNA Amplification*, Airlock, H. E. ed., Stockton Press, New York (1989)). The following primers are used for the amplifications:

Sense primer:

5' ATAGCAATGGTGACAGCAGAA 3'            [SEQ. ID NO. 19]

Anti-sense primer:

5° CGCCC(AG)A(CT)(TCGA)CC(TCGA)GC(TCGA)CT-
   (GA)CAGTG                            [SEQ. ID NO. 20] 3'

Thirty-five cycles are carried out. The reaction products are subjected to agarose gel electrophoresis. The fragments of the expected size (360 bp) are isolated, blunt-ended and subcloned into the pGEM3 vector (Promega) using standard techniques (Ausubel et al., *Current Protocols in Molecular Biology*, John Wiley & Sons, New York (1988)). The PTP-D identity of the subcloned PCR fragments is verified by sequencing using the enzymatic chain termination method (Sanger et al., *Proc. Natl. Acad. Sci. USA* 74:5463–5467 (1977)) using Sequenase (United States Biochemical, Cleveland, Ohio 44122, U.S.A.)

11. EXAMPLE 6

Detection of the Presence of and Measurement of the Quantity of a PTP-D Protein or Glycoprotein in a Cell 11.1 Change of the prokaryotic expression vector PGEX To accommodate a cDNA fragment from PTP-D1 (see below) the cloning sites of the pGEX2T vector (Pharmacia, Uppsala, Sweden) is changed using standard techniques (*Current Protocols in Molecular Biology*, eds. F. M. Ausubel et al., John Wiley & Sons, New York, 1988). The pGEX2T vector is digested with the restriction enzymes BamHI and EcoRI and isolated. The following oligonucleotides are ligated into the digested pGEX2T vector.

5' GATCTCCGAATTCCATGGATCCAGGC-
   CTCTAGAAGCTTAC 3'                    [SEQ. ID NO. 21]

3' AGGCTTAAGGTACCTAGGTCCG-
   GAGATCTTCGAATGTTAA 5'                [SEQ. ID NO. 22]

thereby giving rise to the vector pGEX-AK2 with the following cloning sites:

5' EcoRI, NcoI, BamHI, StuI, XbaI, HindIII 3'

11.2 Expression of GST-PTP D1 fusion protein in *E. coli*

The cDNA encoding PTP-D1 (EXAMPLE 2) is digested with the restriction enzymes EcoRI and BglII. After digestion, a fragment of about 1600 bp is isolated and ligated into the pGEX-AK2 (digested with EcoRI and BamHI) using standard techniques (*Current Protocols in Molecular Biology*, eds. F. M. Ausubel et al., John Wiley & Sons, New York, 1988). The inserted fragment corresponds to the coding region of PTP-D1 shown in FIG. 4 of the present invention (i.e., it is coding for 272 amino acids) and about 800 bp of the 3' untranslated region. The pGEX-AK2/PTP-D1 vector construct, which encodes a fusion protein of glutathione S-transferase and PTP D1 (Smith et al., *Proc. Natl. Acad. Sci. USA* 83:8703–8707 (1988)), is introduced into the *E. coli* strains DH5α (Cat. No. 8263SA, Bethesda Research Laboratories, Gaithersburg, Md.) and SURE™ (Cat. No. 200294, Stratagene, La Jolla, Calif. 92037).

Overnight cultures of the transformed *E. coli* are grown in LB medium and diluted 1:10 in fresh medium and grown for 1 hour. Isopropyl-1-thio-β-D-galactopyranoside (IPTG) is added to a final concentration of 0.5 mM (DH5α) and 5 mM (SURE) and the cultures are incubated for a further 4 hours. Controls: 1) pGEX-AK2 with and without IPTG; 2) pGEX- AK2/PTP-D1 without addition of IPTG. The GST-PTP D1 fusion protein is isolated either as an insoluble product from inclusion bodies (using 3 washes in 50 mM N-2-Hydroxyethylpiperazine-N'-2-ethanesulphonic acid (HEPES) buffer pH 7.5 containing 1.0 percent (vol/vol) Triton X100) or as a soluble protein using glutathione-Sepharose 4B affinity chromatography (Cat. No. 17-0756-01, Pharmacia, Uppsala, Sweden) according to the manufacturer's instructions.

11.3 Production of antibodies with specificity for PTP-D1

Antiserum with specificity for PTP-D1 is produced by standard techniques (*Practical Immunology* 3rd Edition, L. Hudson & F. C. Hay, Blackwell, Oxford (1989)). In brief, 200 μg of the GST-PTP-D1 fusion protein in 200 μl phosphate buffered saline are combined with an equal volume of Freund's complete adjuvant (Sigma, Cat. No. F5881) and injected intramuscularly into the thigh muscle of two New Zealand rabbits. Each rabbit receives 100 μg of the fusion protein. Two weeks after the first injection, boost injections are performed (same procedure as the initial immunization but without Freund's adjuvant). After further two weeks 20 ml of blood are obtained from each rabbit. The blood is allowed to clot at room temperature for 1 hour in glass tubes, which are centrifuged after loosening the clot from the wall of the tubes. The serum is transferred to a new tube and stored in aliquots at −20° C. until use.

To remove the antibodies which react with the glutathione S-transferase (GST) the serum is passed over a glutathione-Sepharose 4B column which has been saturated with glutathione S-transferase using the procedure described above ("Expression of GST-PTP D1 fusion protein in *E. coli*). The pGEXAK2 construct is used to produce the GST protein. The serum is passed three times over the column to ensure complete removal of the anti-GST antibodies. The efficiency of the removal is assessed by Western blotting as described below ("Detection of the Presence and Measurement of the Quantity of PTP-D1 in a Cell Line").

11.4 Detection of the Presence and Measurement of the Quantity of PTP-D1 in a Cell Line The anti-PTP-D1 antibody can be used to detect the expression of PTP-D1 in mammalian cells. Immunofluorescence according to standard procedures will provide information about expression in specific cell lines and tissues. Even more importantly, this antibody preparation can be used to determine the quantity in cell lines and tissues. As an example of the latter application of the anti-PTP D1 antibody, the detection of PTP-D1 in the RD cell line (American Type Culture Collection CCL 136) is described below. It should be emphasized that this EXAMPLE should not in any way limit the use of the antibody which can be used for detection of PTP-D1 in other cells and tissues as well. Likewise, the antibody preparation can be useful in purification of PTP-D1 and for establishing other types of detection assays.

Using standard techniques, the RD (embryonal rhabdomyosarcoma; human) cell line is cultured in minimum essential medium (Eagle; Cat. No. 041-022570, Gibco, Life Technologies Ltd., Paisley, Scotland) with twice the normal concentrations of amino acids and vitamins with Hanks' balanced salt solution and 10 percent (v/v) fetal calf serum (Gibco-BRL).

The cells are washed twice in phosphate buffered saline and the supernatant removed. The cells from one 10 cm tissue culture plate are lysed in 800 μl of Triton X1OO lysis buffer (20 mM HEPES pH 7.5, 50 mM NaCl, 10 percent glycerol, 1.0 percent Triton X1OO, 1.5 mM $MgCl_2$, 4 mM Ethylene Glycol-bis(β-aminoethylethyl ether) N,N,N',N'-tetraacetate (EGTA; Sigma ED2SS), 10 μg/ml aprotinin, 1 mM phenylmethylsulfonyl fluoride (PMSF)), centrifuged and the supernatant is stored in aliquots at −80° C. until use. One to fifty μl of this lysate is mixed with 25 μl SDS sample buffer (62.5 mM Tris-Cl pH 7.0, 3.0 percent (w/v) SDS, 10 percent (v/v) glycerol, 10 percent 2-mercaptoethanol, and 0.05 percent (w/v) bromophenol blue), boiled for 5 minutes, separated by SDS-polyacrylamide gel electrophoresis (7.5 percent) and blotted onto nitrocellulose using standard techniques (Burnetts, W. N. (1981) *Anlyt. Biochem.* 112:195–201). A standard curve for quantitative determination of PTP-D1 is produced by using defined amounts of the *E. coli* produced GST-PTP-D1 fusion protein from above in parallel with the RD cell lysates. The nitrocellulose filters are incubated for 30 minutes with 2 grams milk powder (Carnation, Non fat dry milk, Carnation, Los Angeles) per liter phosphate buffered saline (PBS) to block unspecific binding, washed once in PBS containing 0.02 percent (v/v) Tween 20 (Sigma P1379) (PBS-Tween) and 0.2 percent (w/v) gelatin (BioRad Cat. No. 170-6537, Richmond, Calif.), washed 3 times in PBS-Tween and finally incubated for 4 hours with a 1:200 dilution (in PBS-Tween) of the anti-PTP-D1 antibody preparation from above. After three washings in PBS-Tween, the filters are incubated with horseradish peroxidase-conjugated goat anti-rabbit IgG (Cat. No. 170-6525, BioRad). The filters are washed three times in PBS-Tween and the amount of rabbit antibody, and thereby the amount of PTP-D1, is determined by the enhanced chemiluminescence (ECL) technique according to the manufacturer's instructions (Cat. No. RPN 2106, Amersham, UK). By comparing the signals obtained from the RD cell line with the standard curve obtained with the *E. coli* produced GST-PTP-D1 fusion protein it is possible to determine the amount of PTP D1 produced by the RD cell line.

12. EXAMPLE 7

Identification of a Molecule That Stimulates or Inhibits Enzymatic 12.1 Activity of a PTP-D Protein or Glycoprotein The cDNA containing the entire coding region of PTP-D1 or a functional portion thereof is inserted into the mammalian expression vector pcDNA I (Cat. No. V490-20, Invitrogen, San Diego) using standard techniques (Ausubel et al., *Current Protocols in Molecular Biology,* John Wiley & Sons, New York (1988)). The 293 cell transient expression system described by Gorman et al., Virology 171:377–385 (1989) is used for production of enzymatically active PTP D1. Using standard techniques, the 293 cells are cultured in 5% C02 at 37° C. in Dulbecco's Modified Eagle Medium (Cat. No. a041-02430, Gibco, Life Technologies Ltd., Paisley, Scotland) supplemented with 10 percent (v/v) fetal calf serum (Gibco).

Ten μg of the plasmid construct PTP-D1/pcDNA I are mixed with 0.5 ml 0.25M $CaCl_2$ and 0.5 ml 2×BBS (50 mM N,N-bis(2-hydroxyethyl)-2 aminoethane-sulfonic acid (BES), 280 mM NaCl, 1.5 mM $Na_2HPO_4$) and used for transfection of $1.5×10^6$ 293 cells in a 10 cm Petri dish as, described by Chen & Okayama (*Mol. Cell. Biol.* 7:2745–2752 (1987)). The cells are incubated 24 hours at 37° C. under 3% $CO_2$ after the addition of the Ca-phosphate-DNA precipitate, then washed once in DMEM supplemented with 10 percent fetal calf serum and incubated in fresh medium for additional 24 hours at 37° C. under 5% $CO_2$. The medium is removed and the cells lysed in 1.0 ml of lysis buffer (20 mM HEPES pH 7.5, 150 mM NaCl, 10 percent glycerol, 1.0 percent Triton X100, 1.5 mM $MgCl_2$, 4 mM Ethylene Glycol-bis(β-aminoethylethyl ether) N,N, N',N'-tetraacetate (EGTA; Sigma ED2SS), 10 μg/ml aprotinin, 1 mM PMSF). The cell lysates are centrifuged at 2500×g for 2 minutes at 4° C. The supernatant is removed and 100 itl aliquots are quick-frozen in liquid nitrogen and stored at −70° C. until use.

Three different substrates are used for the evaluation of potential inhibitors or stimulators of PTP-D1 phosphatase activity: 1) p-nitrophenyl phosphate (pNP-P; Sigma 104-0); 2) $^{32}$P-labeled Raytide (Oncogene Science Inc., Manhasset, N.Y.); 3) $^{32}$P-labeled bovine myelin basic protein (MBP). Substances which either decrease or increase the activity of PTP-D1 against one or more of these substrates are analyzed further.

The activity of PTP-D1 towards pNP-P is measured essentially as described by N. K. Tonks et al., *J. Biol. Chem.* 263:6731–6737 (1988)). Using microtiter plates, ten μl of the 293 lysate from above are incubated with 100 μl of pNP-P (30 and 100 mM, respectively) at room temperature. The absorbance is read with one minute intervals in Dynatech MR5000 reader. The substances to be analyzed for stimulatory or inhibitory activities are added to the PTP-D1/293 cell lysate 5 minutes prior to the addition of pNP-P.

12.2 Labeling of Raytide and myelin basic protein with 32p

The activity of PTP-D1 towards $^{32}$P-labeled Raytide™ is measured essentially as described by Krueger et al. (*EMBO J.* 9:3241–3252 (1990)). The synthetic peptide Raytide is labeled with $^{32}$P using the tyrosine kinase p6O$^{c-src}$ according to the manufacturer's instructions (Oncogene Science) with minor modifications. In brief, 2 μl of p6O$^{c-src}$ are mixed with 20 μl Raytide (1 mg/ml) and 108 μl of kinase buffer (50 mM HEPES pH 7.5 containing 10 MM $MgCl_2$, 0.2% (v/v) β-mercaptoethanol, 30 μM ATP and 50 μCi [γ-$^{32}$P]ATP). The mixture is incubated at 37° C. for 16 hours, and the reaction is stopped by addition of 500 μl of 20 percent (w/v) trichloroacetic acid (TCA) in 20 mM $NaH_2PO_4$ and 100 μl of 5 mg/ml of acetylated bovine serum albumin. The mixture is centrifuged, the precipitate is washed three times in 20 percent TCA/20 mM $NaH_2PO_4$ and finally redissolved in 0.2M Tris-Cl pH 8.0.

Myelin basic protein (Sigma) is labeled with a procedure similar to that used for labeling of Raytide as described by Guan et al., *Nature* 350:359–362 (1991). Thirty μg of MBP is labeled in a 60 μl reaction containing the following components: 50 mM HEPES buffer pH 7.5, 10 mM $MgCl_2$, 0.067% β-mercaptoethanol, 0.05 mM ATP including 150 μCi [γ-$^{32}$P]ATP and 4 U p43$^{v-abl}$ kinase (Oncogene Science). The mixture is incubated for 60 minutes at 30° C., and the reaction is stopped by addition of ice-cold trichloroacetic acid to a final concentration of 20 percent. After 30 minutes on ice, the precipitate is washed three times in 20 percent TCA and redissolved in 100 μl $H_2O$.

12.3 The PTPase activity assay using Raytide or MBP

Five μl 10x PTPase buffer (25 mM HEPES pH 7.3, 5 mM EDTA, 10 mM dithiothreitol) are mixed with a) 5 μl $^{32}$P-labeled Raytide or MBP (corresponding to 10–20×10$^4$ counts per minutes), b) 5, 10 and 25 μl, respectively, of the PTP-D1/293 cell lysate, and c) $H_2O$ to a final volume of 50 μl. The reaction is stopped after incubation for 30 minutes at 37° C. In the case of Raytide, the reaction is stopped by addition of 0.75 ml acidic charcoal mixture (Krueger et al., *EMBO J.* 9:3241–3252 (1990)): 0.9M HCl, 90 mM sodium pyrophosphate, 2 mM $NaH_2PO_4$, 4% (v/v) Norit A (Sigma)). After mixing and centrifugation, 400 μl of the supernatant are removed and the amount of radioactivity measured. When using MBP as a substrate, the reaction is stopped by 20 percent TCA (final volume). The amount of $^{32}$P in the supernatant is then measured.

The substances to be analyzed for stimulatory or inhibitory activities are added to the PTP-D1/293 cell lysate 5 minutes prior to initiation of the assays.

13. EXAMPLE 8 cDNA Cloning of PTP-D1

13.1 Methods

RNA was isolated from human skeletal muscle by the guanidinium thiocyanate/CsCl procedure (Chirgwin et al., 1979, *Biochem.* 18:5293–5299) and poly(A)$^+$ RNA was selected on an oligo(dT) cellulose column (Aviv et al., 1972, *Proc. Natl. Acad. Sci. USA* 58:1408–1412). A Lambda ZAP II cDNA library was prepared using 5 μg of poly (A)$^+$ RNA according to the manufacturer's instructions (Stratagene, La Jolla, Calif.) Two million independent plaques were screened from the library using standard filter hybridization techniques (*Current Protocols in Molecular Biology,* eds. F. M. Ausubel et al., John Wiley & Sons, New York (1988)). A fragment of the partial PTP-D1 cDNA clone labelled with $^{32}$P by the Random Primers DNA Labeling System (Cat. no. 8187SA, Bethesda Research Laboratories, Gaithersburg, Md. 20877, U.S.A.) was hybridized to duplicate Hybond N+ (Amersham) filters. The filters were washed at 42° C. in 0.1×SSC, 0.05% SDS, and exposed to X-ray films. Fourteen positive clones (denoted A to N) were identified, plaque purified, and subjected to in vivo excision before restriction analysis. The coding region of the longest clone was sequenced by the dideoxy chain termination method described by Sanger et al., 1977, *Proc. Natl. Acad. Sci. USA* 74:5463–5467), (Sequenase, U.S. Biochemicals).

The fibroblast cell line 293 (American Type Culture Collection CRL 1573) was used for transient expression experiments as described in detail previously (Lammers et al., 1993, J. Biol. Chem. 268:22456–62; Lammers et al., 1990, J. Biol. Chem. 265:16886–90). Two micrograms of plasmid DNA were transfected into 3×10$^5$ cells in 10 cm$^2$ wells according to the procedure described by Chen and Okayama (1987, Mol. Cell Biol. 7:2745–52). Transfections were performed with pCMV expression plasmids containing the following cDNAs PTP-D1, v-src, chicken c-src, and v-src in which Tyr$_{527}$ has been mutated to Phe (src$_{Y527F}$). The expression plasmids were transfected either individually or in combinations. Eighteen hours later the medium was changed, and after further 24 hours the cells were lysed directly in SDS-sample buffer and analyzed for phosphotyrosine content by immunoblotting with the anti-phosphotyrosine antibody 5E2 (Fendly et al., 1990, Cancer Res. 50:1550–8). For immunoprecipitation experiments, the culture medium of the transfected cells was changed to $^{35}$S-L-Met containing medium the night before. The cells were lysed in 0.2 ml of lysis buffer and the expression levels of PTP-D1 and c-src were analyzed by immunoblotting using rabbit polyclonal anti-peptide antibodies directed either against the PTPD1 peptide sequence QEVSEPLTAARHAQ (SEQ. ID NO. 42) (residues 618–631) or the carboxyterminus of the src protein (LEDYFTSTEPQYQPGENL) (SEQ. ID NO. 43). With the residual lysate an immunoprecipitation was performed with the rabbit polyclonal antiserum directed against the carboxyterminus of the src protein (Lammers et al., 1993, J. Biol. Chem. 268:22456–62, Lammers et al., 1990, J. Biol. Chem.

265:16886–90). The samples were subjected to SDS-PAGE and the dried gel autoradiographed.

13.2 Results

A full-length cDNA clone of PTP-D1 (6.2 kb) was isolated from a human skeletal muscle cDNA library and characterized. The nucleotide sequence (SEQ. ID NO. 35) and the predicted amino acid sequence (SEQ. ID NO. 36) of the PTP-D1 cDNA clone are presented in FIGS. 5A–5J. A recombinant plasmid vector containing the full length cDNA clone (J324) of PTP-D1 was deposited on Nov. 17, 1993 with the American Type Culture Collection, 12301 Parklawn Drive, Rockville, Md. 20852, and assigned accession number 75621.

Downstream of two in-frame stop codons, an ATG codon is found at nucleotides 333–335 which conforms to a consensus translation initiation sequence (Kozak, 1984, Nucleic Acids Res. 15:8125–48). The predicted PTP-D1 protein, which neither contains a signal sequence nor a transmembrane domain, consists of 1174 amino acids with a calculated molecular weight of 133 kDa. There is only one PTP domain which is located in the extreme C-terminal part of the molecule. The predicted amino acid sequence contains many of the hallmarks of classical PTPs and are highlighted in FIG. 6. In Table 2, PTP-D1 and PTP-D2 were compared with the most related PTPs using the ALIGN and GAP programs. (Needleman et al., 1970, J. Mol. Biol. 48: 443–53; Dayhoff et al., 1983 Methods Enzymol., 91:524–45.) They are identical to other PTPs in the 30–40percent range, with PTPH1 and PTP1C exhibiting the highest degree of identity. However, their striking homology to each other clearly indicates that they define a novel subgroup to PTPs, which we have denoted the PTP D subfamily.

6:1251–7), and 40–276 in PTP1B (Charbonneau et al., 1989, Proc. Natl. Acad. Sci. USA. 86:5252–6.

The N-terminal part shows similarity to the ezrin-radixin-band 4.1 protein family (Gould et al., 1989, EMBO J 8:4133–42; Conboy et al., 1986, Proc. Natl. Acad. Sci. USA 83:9512–6; Funayama et al., 1991, J. Cell. Biol. 115:1039–48), suggesting that PTP-D1 belongs to the class of intracellular PTPs with an overall structure similar to that of PTPH1 (Yang et al., 1991, Proc. Natl. Acad. Sci. USA 88:5949–53) and PTPMEG1 (Gu et al., 1991, Proc. Natl. Acad. Sci. USA 88:5867–71) as shown schematically in FIG. 7A.

The N-terminal portion of PTP-D1 (about 310 residues) shows similarity to homologous regions of proteins which are thought to act as links between the cytoskeleton and the cell membrane: band 4.1 (Conboy et al., 1986, Proc. Natl. Acad. Sci. USA 83:9512–6); ezrin (Gould et al., 1989, EMBO J 8:4133–42); moesin (Lankes et al., 1991, Proc. Natl. Acad. Sci. USA, 88:8297–301; merlin (Trofatter et al., 1993, Cell 72:791–800). Interestingly, similar regions have been described in two PTPs, PTPH1, and PTPMEG1. A comparison of the predicted amino acid sequence of the N-terminal part of PTP-D1 with the homologous regions of PTPH1 and PTPMEG1 is shown in FIG. 7C. Although many features have been conserved among the three PTPs, it is apparent that PTPH1 and PTPMEG1 are more closely related to each other than to PTP-D1. The ezrin-like domain of PTP-D1 shows 31 and 33 percent identity to the homologous domains of PTPH1 and PTPMEG1, respectively, whereas PTPH1 and PTPMEG1 share 57 percent identity in this region. In addition, three putative src SH2 binding sites may be assigned in the ezrin-like domain of PT-PD1: $Y_{158}ESQ$, $Y_{207}MQE$ and $Y_{217}GEE$ (Songyang et al., 1993, Cell, 72:769–8).

TABLE 2

Alignment of the predicted amino acid sequences of the PTP-D1 and PTP-D2 PCR fragments with similar regions of the most related PTPs.

|        | PTP-D1 | PTP-D2 | PTPH1 | PTP1C | MEG1 | LAR  | PTPδ | CD45 | PTP1B |
|--------|--------|--------|-------|-------|------|------|------|------|-------|
| PTP-D1 |        | 46.6   | 17.1  | 17.1  | 15.2 | 14.9 | 14.4 | 12.4 | 10.4  |
| PTP-D2 | 76     |        | 20.3  | 19.2  | 13.8 | 16.5 | 14.1 | 12.2 | 11.4  |
| PTPH1  | 35     | 35     |       | 15.7  | 33.4 | 20.4 | 17.9 | 13.9 | 15.1  |
| PTP1C  | 35     | 39     | 32    |       | 22.7 | 19.2 | 20.1 | 16.1 | 21.0  |
| MEG1   | 28     | 32     | 50    | 34    |      | 20.6 | 23.1 | 16.2 | 18.9  |
| LAR    | 32     | 33     | 33    | 36    | 36   |      | 53.1 | 15.8 | 20.0  |
| PTPδ   | 32     | 33     | 33    | 34    | 37   | 96   |      | 17.5 | 15.7  |
| CD45   | 38     | 38     | 30    | 36    | 35   | 33   | 33   |      | 16.7  |
| PTP1B  | 28     | 30     | 36    | 36    | 37   | 28   | 29   | 38   |       |

The numbers in the top-right part are the alignment scores using the ALIGN program (expressed as the number of standard deviations of real score above the score from 100 random runs). The gap penalty is 10. A score greater than 5 is considered indicative of homology. The numbers in the bottom-left part are the identities expressed as percentage using GAP program in the UWGCG package. The gap weight is 3.0 and the length weight 0.1. The PTP-D1 and PTP-D2 sequences corresponding to residues 921–1166 in the full-length clone of PTP-D1 and PTP-D2 are compared with residues 670–900 in PTPH1 (Yang et al., 1991, Proc. Natl. Acad. Sci. USA 88:5949–53), 272–516 in PTP1C (Shen et al., 1991, Nature 352:736–9), 679–910 in PTP-MEG1 (Gu et al., 1991, Proc. Natl. Acad. Sci. USA 88:5867–71), 1664–1897 in LAR domain 2 (Streuli et al., 1988, J. Exp. Med. 168:1523–30), 1280–1513 in PTPδ domain 2 (Krueger et al., 1990, EMBO J 9:3241–52), 516–750 in CD45 domain 1 (Ralph et al., 1987, EMBO J, Despite the close relationship between the two PTP subfamilies they differ significantly in the intervening sequence that separates the ezrin-like and PTP domains which in PTP-D1 is about 150 amino acids longer than that in PTPH1 and PTPMEG1 (FIG. 7A). PTPH1 and PTPMEG1 are about 47 percent identical in this region and a homology analysis with the ALIGN program gives a score of 37.0 (gap penalty: 10; random runs: 100; where a score of more than 5 is indicative of homology). The scores for PTP-D1 are 0.0 and 0.36 when compared with PTPH1 and PTPMEG1. There are several consensus sites for casein II kinase phosphorylation and many tyrosine residues throughout the molecule which might serve as targets for tyrosine kinases. The sequence motif PYX, where X is a nonpolar amino acid (A, L, V or P), is found 5 times in the intervening region and once at the boundary to the ezrin-like domain. Further, there are two relatively short stretches which might promote the binding of specific molecules to PTP-D1. One is PPPPYPPPRP (SEQ. ID. NO. 44) (residues 565–574) which resembles the consensus sequence for SH3 domain binding proteins (Ren et al., 1993, Science 259:1157–61). The other is the very acidic region EEEEDEDFEEE (SEQ. ID NO. 45) (residues 712–722) which could bind to positively charged target sequences on other proteins. Additionally, the sequence PQPYVMPPPP (SEQ. ID NO. 46) (residues 334–343) at the boundary between the ezrin-like domain and the intervening part might have SH3 domain binding capacity.

As already indicated above, PTP-D1 contains most of the hallmarks of PTPs. The catalytically essential cysteine and its flanking residues, VHC$_{1108}$SAGVGRTG (SEQ. ID NO. 47), are completely conserved (FIG. 6 and FIG. 7B). Surprisingly, another cysteine residue conserved in the consensus KCXXYWP (SEQ. ID NO. 48) in classical PTPs is replaced with a serine residue in both PTP-D1 (position 1007) and PTP-D2.

An alignment of the PTP domains of PTP-D1, PTPH1, and PTPMEG1 is given in FIG. 7B. PTP-D1 is 41 and 38 percent identical to PTPH1 and PTPMEG1 in the PTP domain, respectively. In contrast, PTPH1 and PTPMEG1 are found to be 64 percent identical in the PTP domain, directly indicating a very close relationship between these two PTPs. As shown in FIG. 7B, the enzyme domain of PTP-D1 contains three insertions in comparison with PTPH1 and PTPMEG1, two of which are also found in the PTP-D2 sequence. The most C-terminal of these show no homology between PTP-D1 and PTP-D2 which raise the possibility that these insertions determine in part the interaction with substrates and thereby the functional specificity of the enzymes.

It can be concluded that PTP-D1 shows most of the general features of the catalytic domain of PTPs but not the specific features of the PTPH1/MEG1 subfamily. This suggests that PTP-D1 and PTP-D2 have separated early in evolution from the PTPH1/PTPMEG1 branch or, alternatively, that these subfamilies of PTPs have evolved separately.

In order to study the functional aspects of PTP-D1, we transiently expressed PTP-D1 in human 293 embryonic fibroblasts using a CMV-based mammalian expression vector. PTP-D1 was coexpressed with either v-src, c-src, or a constitutively activated c-src mutant with a phenylalanine replacing tyrosine-527. Cell lysates were analyzed by SDS-PAGE and Western blotting. FIG. 8A shows that all three versions of the src-kinase when transfected alone phosphorylate a broad range of proteins. In cells cotransfected with PTP-D1, an additional band of 130 kDa corresponding approximately to the predicted size of PTP-D1 becomes heavily tyrosine phosphorylated. Transfected cell lysates were analyzed by SDS-PAGE after immunoprecipitated with an antibody directed against the C-terminus of the src kinase which is deleted from the v-src protein. The coimmunoprecipitation shown in FIG. 8B demonstrated that PTP-D1 is tightly bound to pp60$^{src}$ and pp60$^{srcY527F}$.

13.3 Discussion

PTP-D1 consists of three domains. The C-terminal portion is a classical PTP domain with the hallmarks of a bona fide PTP. The N-terminal region is similar to a domain found in ezrin and several other proteins, including two recently identified PTPs, PTPH1 and PTPMEG1. The intervening sequence does not show strong homology to any known protein.

In classical PTPs, the cysteine residue in the consensus sequence KCXXYWP (SEQ. ID NO. 48) is highly conserved. Surprisingly, this cysteine is replaced with a serine residue in PTP-D1 and PTP-D2. However, it is unlikely that this cysteine to serine substitution has significant impact on the intrinsic enzyme activity, since this motif is not found in several non-classical protein tyrosine phosphatases such as VH1 and cdc25 for which enzyme activity is well documented (Guan et al., 1991, Nature 350:359–62; Gautier et al., 1991, Cell 67:197–211). Also, mutational analysis of this residue in the N-terminal PTP domain of LAR indicates that its contribution to the intrinsic activity is rather small (Pot et al., 1991, J. Biol. Chem., 266:19688–96). On the other hand, since cysteine residues are normally well conserved among related proteins for structural reasons, it is likely that the substitution is significant with regard to the overall folding of PTP-D1 and the specific interactions with protein substrates. The foregoing indicates that PTP-D1 has a distinct substrate specificity.

Even though PTP-D1, PTPH1 and PTPMEG1 all have the same overall structure, the sequence alignment analyses indicate that PTPH1 and PTPMEG1 belong to one subfamily, PTP-D1 and PTP-D2 to another. We have named the latter the PTP-D subfamily. First, PTPH1 and PTPMEG1 are 64 percent identical in the PTP domain, whereas PTP-D1 only shows 41 and 38 percent identity respectively to PTPH1 and PTPMEG1 in this region. The PCR fragments encompassing portions of the catalytic domains of PTP-D1 and PTP-D2 are 76 percent identical. Second, similar relationships are found in the N-terminal, ezrin-like domain. Third, the intervening sequence of PTP-D1 is about 150 amino acids longer and does not show any significant structural similarity to the corresponding regions in PTPH1 and PTPMEG1, which are about 45 percent identical.

PTP-D1 has several structural features which point to specific protein-protein interactions and a defined subcellular localization. As already pointed out for PTPH1 and PTPMEG1, the N-terminal, ezrin-like domain is likely to localize PTP-D1 to the cell membrane since it belongs to a class of proteins which seem to anchor the cytoskeleton to the plasma membrane: ezrin, band 4.1, moesin, radixin, merlin and talin (Rees et al., 1990, Nature 347:685–9). Our coexpression studies further show that there is a strong association between tyrosine phosphorylated PTP-D1 and pp60$^{src}$. This interaction could be mediated by binding of the src SH2 domain to three putative binding motifs found in the ezrin-like domain of PTP-D1. Likewise, the PYX motif which appears several times in the intervening segment may represent a specific phosphorylation site and could promote binding to SH2 domains. Alternatively, this association could also be mediated by the proline-rich region which is similar to defined SH3 domain binding structures in other proteins. In this context it is of interest that several cytoskeletal proteins have been found to contain SH3 domains (Mussachio et al., 1992, FEBS Lett. 307:55–61), and at least one, tensin, to contain an SH2 domain (Davis et al., 1991, Science 252:712–5).

At least three different types of stimuli lead to the phosphorylation of cellular proteins in the molecular weight range of 110–130 kDa: 1) clustering of $\beta_1$ integrins by antibodies or cell adhesion; 2) activation of the receptors for bombesin, vasopressin, and endothelin; 3) transformation by pp60$^{v-src}$ (Kornberg et al., 1991, Proc. Natl. Acad. Sci. USA, 88:8392–6; Guan et al., 1991, Cell. Regul. 2:951–64; Zachary et al., 1992, J. Biol. Chem. 267:19031–4). The focal adhesion kinase (pp125$^{FAK}$) has been found to be a major component of this complex of phosphorylated proteins (Schaller et al., Proc. Natl. Acad. Sci. USA, 89:5192–6; Hanks et al., 1991, Proc. Natl. Acad. Sci. USA, 89:8487–8491; Kornberg et al., 1992, J. Biol. Chem. 267:23439–42). Furthermore, in the case of cell adhesion and of cell transformation by pp60$^{src}$, the changes in phosphorylation correlate with increased pp125$^{FAK}$ tyrosine kinase activity (Guan et al., 1992, Nature 358:690–2). However, other proteins in this size range which are phosphorylated by the src kinase have not yet been characterized. Of the two proteins that contain phosphotyrosine, pp110 and pp130, they were found to associate stably with activated pp60$^{src}$ (Reynolds et al., 1989, Mol. Cell. Biol. 9:3951–8; Kanner et al., 1991, EMBO J. 10:1689–98).

In summary, the molecular weight of PTP-D1, its primary structure with an ezrin-like domain and a putative SH3 domain binding sequence, and its phosphorylation by and interaction with the src-kinase indicate that this PTP-D subfamily of protein tyrosine phosphatases may be involved in the control of tyrosine phosphorylation events in focal adhesions.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising (a) a nucleotide sequence that encodes a polypeptide having the amino acid sequence SEQ ID NO:36; or (b) the complement of the nucleotide sequence of (a).

2. An isolated nucleic acid molecule comprising a nucleotide sequence that hybridizes to the complement of a nucleic acid sequence encoding a polypeptide having the amino acid sequence of SEQ ID NO:36, under conditions including a wash at least as stringent as 0.1×SSC, 0.05% SDS at 42° C., wherein the nucleic acid molecule encodes a full length naturally occurring protein tyrosine phosphatase.

3. The nucleic acid molecule of claim 1 or 2 which is a cDNA molecule.

4. The nucleic acid molecule of claim 1 or 2 which is a genomic DNA molecule.

5. An isolated nucleic acid molecule comprising the nucleotide sequence SEQ ID No: 35.

6. An isolated nucleic acid molecule comprising: (a) a nucleotide sequence that encodes a polypeptide having an amino acid sequence of SEQ. ID NO:36 from amino acids 1–23 of N-terminal region, amino acids 24–339 of ezrin-like domain, amino acids 340–920 of intervening segment, or amino acids 921–1166 of phosphatase domain; or (b) the complement of the nucleotide sequence of (a).

7. An isolated nucleic acid molecule comprising: (a) nucleotide sequence 2025–2054, 2466–2498 or 1332–1361 of SEQ ID NO: 35; or (b) the complement of the nucleotide sequence of (a).

* * * * *